(12) United States Patent
Freer et al.

(10) Patent No.: US 11,000,835 B2
(45) Date of Patent: May 11, 2021

(54) CATALYSTS FOR NATURAL GAS PROCESSES

(71) Applicant: Lummus Technology LLC, Houston, TX (US)

(72) Inventors: Erik M. Freer, Mountain View, CA (US); Wayne P. Schammel, Brisbane, CA (US); Fabio R. Zurcher, Brisbane, CA (US); Joel M. Cizeron, Redwood City, CA (US); Jin Ki Hong, Moraga, CA (US); Anja Rumplecker, San Francisco, CA (US); Sam Maurer, San Francisco, CA (US); Joel Gamoras, Vallejo, CA (US); Daniel Rosenberg, San Francisco, CA (US); Erik C. Scher, San Francisco, CA (US)

(73) Assignee: Lummus Technology LLC, Houston, TX (US)

( * ) Notice: Subject to any disclaimer, the term of this patent is extended or adjusted under 35 U.S.C. 154(b) by 0 days.

(21) Appl. No.: 16/359,786

(22) Filed: Mar. 20, 2019

(65) Prior Publication Data

US 2020/0016580 A1    Jan. 16, 2020

Related U.S. Application Data

(63) Continuation of application No. 15/667,089, filed on Aug. 2, 2017, now Pat. No. 10,300,465, which is a
(Continued)

(51) Int. Cl.
*B01J 27/25* (2006.01)
*B01J 27/232* (2006.01)
(Continued)

(52) U.S. Cl.
CPC .............. *B01J 27/25* (2013.01); *B01J 23/002* (2013.01); *B01J 23/10* (2013.01); *B01J 23/30* (2013.01);
(Continued)

(58) Field of Classification Search
CPC . B01J 23/002; B01J 23/02; B01J 23/10; B01J 23/30; B01J 23/24; B01J 35/02;
(Continued)

(56) References Cited

U.S. PATENT DOCUMENTS 3,413,817 A    12/1968   Kniel
3,596,473 A    8/1971    Streich
(Continued)

FOREIGN PATENT DOCUMENTS

CN    86104014 A    12/1986
CN    1073891 A    7/1993
(Continued)

OTHER PUBLICATIONS

"Autothermal Partial Oxidative Coupling of Methane," An IP.com Prior Art Database Technical Disclosure, IP.com No. IPCOM000173290D, Jul. 29, 2008.
(Continued)

*Primary Examiner* — Patricia L. Hailey
(74) *Attorney, Agent, or Firm* — Seed IP Law Group LLP

(57) ABSTRACT

Catalysts, catalytic forms and formulations, and catalytic methods are provided. The catalysts and catalytic forms and formulations are useful in a variety of catalytic reactions, for example, the oxidative coupling of methane. Related methods for use and manufacture of the same are also disclosed.

25 Claims, 16 Drawing Sheets

Related U.S. Application Data continuation of application No. 14/856,177, filed on Sep. 16, 2015, now Pat. No. 9,751,079.

(60) Provisional application No. 62/051,779, filed on Sep. 17, 2014.

(51) Int. Cl.

| | | |
|---|---|---|
| *B01J 23/10* | (2006.01) | |
| *B01J 23/30* | (2006.01) | |
| *B01J 37/08* | (2006.01) | |
| *B01J 37/00* | (2006.01) | |
| *C07C 5/48* | (2006.01) | |
| *C07C 2/84* | (2006.01) | |
| *B01J 37/04* | (2006.01) | |
| *B01J 35/00* | (2006.01) | |
| *B01J 35/12* | (2006.01) | |
| *B01J 23/00* | (2006.01) | |
| *B01J 35/06* | (2006.01) | |
| *B01J 35/02* | (2006.01) | |

(52) U.S. Cl.
CPC ......... *B01J 27/232* (2013.01); *B01J 35/0006* (2013.01); *B01J 35/026* (2013.01); *B01J 35/06* (2013.01); *B01J 35/12* (2013.01); *B01J 37/0009* (2013.01); *B01J 37/04* (2013.01); *B01J 37/08* (2013.01); *C07C 2/84* (2013.01); *C07C 5/48* (2013.01); *B01J 37/0036* (2013.01); *C07C 2521/06* (2013.01); *C07C 2523/02* (2013.01); *C07C 2523/10* (2013.01); *C07C 2523/30* (2013.01); *C07C 2527/25* (2013.01); *Y02P 20/52* (2015.11)

(58) Field of Classification Search
CPC ................ B01J 2523/20; B01J 2523/35; B01J 2523/36; B01J 2523/37; B01J 2523/47; B01J 2523/48; B01J 2523/49; B01J 2523/67; B01J 2523/68; B01J 2523/69
USPC .......................... 502/302–304, 525, 527.24
See application file for complete search history.

(56) References Cited

U.S. PATENT DOCUMENTS

| | | |
|---|---|---|
| 4,105,641 A | 8/1978 | Buysch et al. |
| 4,126,580 A | 11/1978 | Lauder |
| 4,140,504 A | 2/1979 | Campbell et al. |
| 4,375,566 A | 3/1983 | Kawamata et al. |
| 4,554,395 A | 11/1985 | Jones et al. |
| 4,629,718 A | 12/1986 | Jones et al. |
| 4,636,378 A | 1/1987 | Pastor et al. |
| 4,695,668 A | 9/1987 | Velenyi |
| 4,751,336 A | 6/1988 | Jezl et al. |
| 4,754,091 A | 6/1988 | Jezl et al. |
| 4,754,093 A | 6/1988 | Jezl et al. |
| 4,777,313 A | 10/1988 | Sofranko et al. |
| 4,780,449 A | 10/1988 | Hicks |
| 4,814,539 A | 3/1989 | Jezl et al. |
| 4,826,796 A | 5/1989 | Erekson et al. |
| 4,844,803 A | 7/1989 | Urech et al. |
| 4,849,571 A | 7/1989 | Gaffney |
| 4,895,823 A | 1/1990 | Kolts et al. |
| 4,900,347 A | 2/1990 | McCue et al. |
| 4,939,311 A | 7/1990 | Washecheck et al. |
| 4,939,312 A | 7/1990 | Baerns et al. |
| 4,962,252 A | 10/1990 | Wade |
| 5,012,028 A | 4/1991 | Gupta et al. |
| 5,024,984 A | 6/1991 | Kaminsky et al. |
| 5,041,405 A | 8/1991 | Lunsford et al. |
| 5,057,478 A | 10/1991 | Abe et al. |
| 5,073,662 A | 12/1991 | Olbrich |
| 5,080,872 A | 1/1992 | Jezl et al. |
| 5,118,898 A | 6/1992 | Tyler et al. |
| 5,132,472 A | 7/1992 | Durante et al. |
| 5,134,103 A | 7/1992 | Lowery |
| 5,137,862 A | 8/1992 | Mackrodt et al. |
| 5,149,516 A | 9/1992 | Han et al. |
| 5,179,056 A | 1/1993 | Bartley |
| 5,196,634 A | 3/1993 | Washecheck et al. |
| 5,198,596 A | 3/1993 | Kaminsky et al. |
| 5,263,998 A | 11/1993 | Mackrodt et al. |
| 5,276,237 A | 1/1994 | Mieville |
| 5,306,854 A | 4/1994 | Choudhary et al. |
| 5,312,795 A | 5/1994 | Kaminsky et al. |
| 5,316,995 A | 5/1994 | Kaminsky et al. |
| 5,328,883 A | 7/1994 | Washecheck et al. |
| 5,336,825 A | 8/1994 | Choudhary et al. |
| 5,336,826 A | 8/1994 | Brophy et al. |
| 5,371,306 A | 12/1994 | Woo et al. |
| 5,414,157 A | 5/1995 | Durante et al. |
| 5,500,149 A | 3/1996 | Green et al. |
| 5,523,493 A | 6/1996 | Cameron et al. |
| 5,599,510 A | 2/1997 | Kaminsky et al. |
| 5,659,090 A | 8/1997 | Cameron et al. |
| 5,670,442 A | 9/1997 | Fornasari et al. |
| RE35,632 E | 10/1997 | Leyshon |
| RE35,633 E | 10/1997 | Leyshon |
| 5,712,217 A | 1/1998 | Choudhary et al. |
| 5,714,657 A | 2/1998 | deVries |
| 5,736,107 A | 4/1998 | Inomata et al. |
| 5,744,015 A | 4/1998 | Mazanec et al. |
| 5,749,937 A | 5/1998 | Detering et al. |
| 5,750,821 A | 5/1998 | Inomata et al. |
| 5,763,722 A | 6/1998 | Vic et al. |
| 5,789,339 A | 8/1998 | Ziebarth et al. |
| 5,817,904 A | 10/1998 | Vic et al. |
| 5,830,822 A | 11/1998 | Euzen |
| 5,849,973 A | 12/1998 | Van Der Vaart |
| 5,866,737 A | 2/1999 | Hagemeyer et al. |
| 5,897,945 A | 4/1999 | Lieber et al. |
| 5,917,136 A | 6/1999 | Gaffney et al. |
| 5,935,293 A | 8/1999 | Detering et al. |
| 5,935,897 A | 8/1999 | Trubenbach et al. |
| 5,935,898 A | 8/1999 | Trubenbach et al. |
| 5,936,135 A | 8/1999 | Choudhary et al. |
| 5,959,170 A | 9/1999 | Withers |
| 5,968,866 A | 10/1999 | Wu |
| 6,020,533 A | 2/2000 | Lewis et al. |
| 6,037,298 A | 3/2000 | Hagen et al. |
| 6,087,545 A | 7/2000 | Choudhary et al. |
| 6,096,934 A | 8/2000 | Rekoske |
| 6,110,979 A | 8/2000 | Nataraj et al. |
| 6,114,400 A | 9/2000 | Nataraj et al. |
| 6,143,203 A | 11/2000 | Zeng et al. |
| 6,146,549 A | 11/2000 | Mackay et al. |
| 6,153,149 A | 11/2000 | Rabitz et al. |
| 6,262,325 B1 | 7/2001 | Narbeshuber et al. |
| 6,316,377 B1 | 11/2001 | Fulton et al. |
| 6,355,093 B1 | 3/2002 | Schwartz et al. |
| 6,403,523 B1 | 6/2002 | Cantrell et al. |
| RE37,853 E | 9/2002 | Detering et al. |
| 6,447,745 B1 | 9/2002 | Feeley et al. |
| 6,518,218 B1 | 2/2003 | Sun et al. |
| 6,518,476 B1 | 2/2003 | Culp et al. |
| 6,521,806 B1 | 2/2003 | Tamura et al. |
| 6,521,808 B1 | 2/2003 | Ozkan et al. |
| 6,576,200 B1 | 6/2003 | Yamamoto et al. |
| 6,576,803 B2 | 6/2003 | Cantrell et al. |
| 6,596,912 B1 | 7/2003 | Lunsford et al. |
| 6,610,124 B1 | 8/2003 | Dolan et al. |
| 6,696,388 B2 | 2/2004 | Kourtakis et al. |
| 6,726,850 B1 | 4/2004 | Reyes et al. |
| 6,730,808 B2 | 5/2004 | Bitterlich et al. |
| 6,747,066 B2 | 6/2004 | Wang et al. |
| 6,761,838 B2 | 7/2004 | Zeng et al. |
| 6,764,602 B2 | 7/2004 | Shutt et al. |
| 6,800,702 B2 | 10/2004 | Wass |
| 6,821,500 B2 | 11/2004 | Fincke et al. |
| 6,821,656 B2 | 11/2004 | Dietrich et al. |
| 7,116,546 B2 | 10/2006 | Chow et al. |
| 7,166,267 B2 | 1/2007 | Villa |

(56) References Cited

U.S. PATENT DOCUMENTS

| | | |
|---|---|---|
| 7,176,342 B2 | 2/2007 | Bellussi et al. |
| 7,183,451 B2 | 2/2007 | Gattis et al. |
| 7,199,273 B2 | 4/2007 | Molinier et al. |
| 7,208,647 B2 | 4/2007 | Peterson et al. |
| 7,250,543 B2 | 7/2007 | Bagherzadeh et al. |
| 7,291,321 B2 | 11/2007 | Bagherzadeh et al. |
| 7,332,108 B2 | 2/2008 | Chartier et al. |
| 7,361,622 B2 | 4/2008 | Benderly et al. |
| 7,396,798 B2 | 7/2008 | Ma et al. |
| 7,414,006 B2 | 8/2008 | McConville et al. |
| 7,438,887 B2 | 10/2008 | Suib et al. |
| 7,452,844 B2 | 11/2008 | Hu et al. |
| 7,473,814 B2 | 1/2009 | Basset et al. |
| 7,566,440 B2 | 7/2009 | Lim et al. |
| 7,576,030 B2 | 8/2009 | Benderly |
| 7,576,296 B2 | 8/2009 | Fincke et al. |
| 7,585,812 B2 | 9/2009 | Hu et al. |
| 7,589,246 B2 | 9/2009 | Iaccino et al. |
| 7,619,290 B2 | 11/2009 | Lieber et al. |
| 7,659,437 B2 | 2/2010 | Iaccino et al. |
| 7,667,085 B2 | 2/2010 | Gattis et al. |
| 7,683,227 B2 | 3/2010 | Iaccino et al. |
| 7,687,041 B2 | 3/2010 | Singh |
| 7,700,816 B2 | 4/2010 | Xu |
| 7,728,186 B2 | 6/2010 | Iaccino et al. |
| 7,781,636 B2 | 8/2010 | Iaccino et al. |
| 7,795,490 B2 | 9/2010 | Iaccino et al. |
| 7,829,749 B2 | 11/2010 | Gao et al. |
| 7,867,938 B2 | 1/2011 | De et al. |
| 7,868,243 B2 | 1/2011 | Plissonnier et al. |
| 7,879,119 B2 | 2/2011 | Abughazaleh et al. |
| 7,902,113 B2 | 3/2011 | Zarrinpashne et al. |
| 7,902,639 B2 | 3/2011 | Garrou et al. |
| 7,910,670 B2 | 3/2011 | Knudsen et al. |
| 7,915,461 B2 | 3/2011 | Gattis et al. |
| 7,915,462 B2 | 3/2011 | Gattis et al. |
| 7,915,463 B2 | 3/2011 | Gattis et al. |
| 7,915,464 B2 | 3/2011 | Gattis et al. |
| 7,915,465 B2 | 3/2011 | Gattis et al. |
| 7,915,466 B2 | 3/2011 | Gattis et al. |
| 7,932,296 B2 | 4/2011 | Malhotra et al. |
| 7,932,311 B2 | 4/2011 | Aymonier et al. |
| 7,943,106 B2 | 5/2011 | Robinson |
| 7,968,020 B2 | 6/2011 | Behelfer et al. |
| 7,968,759 B2 | 6/2011 | Iaccino et al. |
| 7,977,519 B2 | 7/2011 | Iaccino et al. |
| 8,039,681 B2 | 10/2011 | Krusic et al. |
| 8,071,498 B2 | 12/2011 | Aono et al. |
| 8,071,836 B2 | 12/2011 | Butler |
| 8,129,305 B2 | 3/2012 | Bagherzadeh et al. |
| 8,277,525 B2 | 10/2012 | Dalton |
| 8,293,805 B2 | 10/2012 | Khan et al. |
| 8,349,758 B2 * | 1/2013 | Gabriel .................. B01J 23/755 264/630 |
| 8,361,925 B2 | 1/2013 | Matsueda et al. |
| 8,399,527 B1 | 3/2013 | Brown et al. |
| 8,399,726 B2 | 3/2013 | Chinga et al. |
| 8,414,798 B2 | 4/2013 | Costello et al. |
| 8,435,920 B2 | 5/2013 | White et al. |
| 8,450,546 B2 | 5/2013 | Chinta et al. |
| 8,552,236 B2 | 10/2013 | Iaccino |
| 8,647,999 B2 | 2/2014 | Hayashi et al. |
| 8,669,171 B2 | 3/2014 | Perraud et al. |
| 8,710,286 B2 | 4/2014 | Butler |
| 8,729,328 B2 | 5/2014 | Chinta et al. |
| 8,759,598 B2 | 6/2014 | Hayashi et al. |
| 8,796,497 B2 | 8/2014 | Chinta et al. |
| 8,865,347 B2 | 10/2014 | Hu et al. |
| 8,911,834 B2 | 12/2014 | Aktas et al. |
| 8,912,381 B2 | 12/2014 | Chinta et al. |
| 8,921,256 B2 | 12/2014 | Cizeron et al. |
| 8,932,781 B2 | 1/2015 | Yang et al. |
| 8,962,517 B2 | 2/2015 | Zurcher et al. |
| 9,040,762 B2 | 5/2015 | Cizeron et al. |
| 9,101,890 B2 | 8/2015 | Tonkovich et al. |
| 9,133,079 B2 | 9/2015 | Weinberger et al. |
| 9,446,387 B2 | 9/2016 | Cizeron et al. |
| 9,446,397 B2 | 9/2016 | Gamoras et al. |
| 9,469,577 B2 | 10/2016 | Schammel et al. |
| 9,527,784 B2 | 12/2016 | Weinberger et al. |
| 9,556,086 B2 | 1/2017 | Schammel et al. |
| 9,598,328 B2 | 3/2017 | Nyce et al. |
| 9,718,054 B2 | 8/2017 | Scher et al. |
| 9,738,571 B2 | 8/2017 | Schammel et al. |
| 9,751,079 B2 | 9/2017 | Freer et al. |
| 9,751,818 B2 | 9/2017 | Zurcher et al. |
| 9,956,544 B2 | 5/2018 | Schammel et al. |
| 9,963,402 B2 | 5/2018 | Cizeron et al. |
| 10,183,900 B2 | 1/2019 | Nyce et al. |
| 10,195,603 B2 | 2/2019 | Scher et al. |
| 10,300,465 B2 | 5/2019 | Freer et al. |
| 10,308,565 B2 | 6/2019 | Schammel et al. |
| 10,654,769 B2 | 5/2020 | Cizeron et al. |
| 2001/0044520 A1 | 11/2001 | Suzuki et al. |
| 2002/0150522 A1 | 10/2002 | Heim et al. |
| 2003/0135971 A1 | 7/2003 | Liberman et al. |
| 2003/0189202 A1 | 10/2003 | Li et al. |
| 2003/0207984 A1 | 11/2003 | Ding et al. |
| 2003/0233019 A1 | 12/2003 | Sherwood |
| 2004/0005723 A1 | 1/2004 | Empedocles et al. |
| 2004/0098914 A1 | 5/2004 | Balachandran et al. |
| 2004/0187963 A1 | 9/2004 | Tayu et al. |
| 2004/0220053 A1 | 11/2004 | Bagherzadeh et al. |
| 2005/0009686 A1 | 1/2005 | Julsrud et al. |
| 2005/0065391 A1 | 3/2005 | Gattis et al. |
| 2005/0199559 A1 | 9/2005 | Duby |
| 2005/0221083 A1 | 10/2005 | Belcher et al. |
| 2005/0255993 A1 | 11/2005 | Tanaka et al. |
| 2006/0018821 A1 | 1/2006 | Suzuki et al. |
| 2006/0083970 A1 | 4/2006 | Shibutani et al. |
| 2006/0125025 A1 | 6/2006 | Kawashima et al. |
| 2006/0135838 A1 | 6/2006 | Bagherzadeh et al. |
| 2006/0141268 A1 | 6/2006 | Kalkan et al. |
| 2006/0155157 A1 | 7/2006 | Zarrinpashne et al. |
| 2006/0177629 A1 | 8/2006 | Kunieda |
| 2006/0283780 A1 | 12/2006 | Spivey et al. |
| 2006/0284162 A1 | 12/2006 | Kurt et al. |
| 2007/0027030 A1 | 2/2007 | Cheung et al. |
| 2007/0043181 A1 | 2/2007 | Knudsen et al. |
| 2007/0073083 A1 | 3/2007 | Sunley |
| 2007/0083073 A1 | 4/2007 | Bagherzadeh et al. |
| 2007/0095445 A1 | 5/2007 | Gangopadhyay et al. |
| 2007/0106089 A1 | 5/2007 | Benderly et al. |
| 2007/0138082 A1 | 6/2007 | Conners, Jr. et al. |
| 2007/0138459 A1 | 6/2007 | Wong et al. |
| 2007/0158611 A1 | 7/2007 | Oldenburg |
| 2008/0051279 A1 | 2/2008 | Klett et al. |
| 2008/0141713 A1 | 6/2008 | Verma |
| 2008/0262114 A1 | 10/2008 | Reynhout |
| 2008/0267852 A1 | 10/2008 | Schumacher et al. |
| 2008/0275143 A1 | 11/2008 | Malhotra et al. |
| 2008/0279744 A1 | 11/2008 | Robinson |
| 2008/0281136 A1 | 11/2008 | Bagherzadeh et al. |
| 2008/0293980 A1 | 11/2008 | Kiesslich et al. |
| 2008/0318044 A1 | 12/2008 | Tian et al. |
| 2009/0043141 A1 | 2/2009 | Mazanec et al. |
| 2009/0087496 A1 | 4/2009 | Katusic et al. |
| 2009/0202427 A1 | 8/2009 | Katusic et al. |
| 2009/0259076 A1 | 10/2009 | Simmons et al. |
| 2009/0267852 A1 | 10/2009 | Tahmisian et al. |
| 2009/0324470 A1 | 12/2009 | Alamdari et al. |
| 2010/0000153 A1 | 1/2010 | Kurkjian et al. |
| 2010/0003179 A1 | 1/2010 | Katusic et al. |
| 2010/0173070 A1 | 7/2010 | Niu |
| 2010/0183937 A1 | 7/2010 | Halloran et al. |
| 2010/0185034 A1 | 7/2010 | Nishimura et al. |
| 2010/0191031 A1 | 7/2010 | Sundaram |
| 2010/0197482 A1 | 8/2010 | Basset et al. |
| 2010/0200501 A1 | 8/2010 | Hoag et al. |
| 2010/0249473 A1 | 9/2010 | Butler |
| 2010/0331174 A1 | 12/2010 | Chinta et al. |
| 2010/0331593 A1 | 12/2010 | Chinta et al. |
| 2010/0331595 A1 | 12/2010 | Chinta et al. |
| 2011/0049132 A1 | 3/2011 | Lee |

(56) References Cited

U.S. PATENT DOCUMENTS

| | | |
|---|---|---|
| 2011/0070139 A1 | 3/2011 | Kim et al. |
| 2011/0104588 A1 | 5/2011 | Kwon et al. |
| 2011/0124488 A1 | 5/2011 | Neltner et al. |
| 2011/0160508 A1 | 6/2011 | Ma et al. |
| 2011/0171629 A1 | 7/2011 | Swager et al. |
| 2011/0189559 A1 | 8/2011 | De Miranda et al. |
| 2011/0217544 A1 | 9/2011 | Young et al. |
| 2011/0240926 A1 | 10/2011 | Schellen et al. |
| 2011/0257453 A1 | 10/2011 | Chinta et al. |
| 2011/0275011 A1 | 11/2011 | Zhu et al. |
| 2012/0029218 A1 | 2/2012 | Kim et al. |
| 2012/0041246 A1 | 2/2012 | Scher et al. |
| 2012/0065412 A1 | 3/2012 | Abdallah et al. |
| 2012/0116094 A1 | 5/2012 | Swager et al. |
| 2012/0129690 A1 | 5/2012 | Larcher et al. |
| 2012/0136164 A1 | 5/2012 | Ying et al. |
| 2012/0153860 A1 | 6/2012 | Wang |
| 2012/0164470 A1 | 6/2012 | Leschkies et al. |
| 2012/0172648 A1 | 7/2012 | Seebauer |
| 2012/0198769 A1 | 8/2012 | Schirrmeister et al. |
| 2012/0204716 A1 | 8/2012 | Schirrmeister et al. |
| 2012/0215045 A1 | 8/2012 | Butler |
| 2012/0222422 A1 | 9/2012 | Nunley et al. |
| 2012/0264598 A1 | 10/2012 | Carpenter et al. |
| 2013/0023709 A1 | 1/2013 | Cizeron et al. |
| 2013/0025201 A1 | 1/2013 | Dalton |
| 2013/0039806 A1 | 2/2013 | Blinn et al. |
| 2013/0040806 A1 | 2/2013 | Dismukes et al. |
| 2013/0089739 A1 | 4/2013 | Polshettiwar et al. |
| 2013/0105305 A1 | 5/2013 | Yang et al. |
| 2013/0142707 A1 | 6/2013 | Chinta et al. |
| 2013/0158322 A1 | 6/2013 | Nyce et al. |
| 2013/0165728 A1 | 6/2013 | Zurcher et al. |
| 2013/0178680 A1 | 7/2013 | Ha et al. |
| 2013/0225884 A1 | 8/2013 | Weinberger et al. |
| 2013/0252808 A1 | 9/2013 | Yamazaki et al. |
| 2013/0253248 A1 | 9/2013 | Gamoras et al. |
| 2013/0266809 A1 | 10/2013 | Nueraji et al. |
| 2013/0270180 A1 | 10/2013 | Zhang et al. |
| 2014/0050629 A1 | 2/2014 | Masuda et al. |
| 2014/0054516 A1 | 2/2014 | Moon et al. |
| 2014/0080699 A1 | 3/2014 | Ghose et al. |
| 2014/0107385 A1 | 4/2014 | Schammel et al. |
| 2014/0121433 A1 | 5/2014 | Cizeron et al. |
| 2014/0128484 A1 | 5/2014 | Hassan et al. |
| 2014/0128485 A1 | 5/2014 | Hassan et al. |
| 2014/0171707 A1 | 6/2014 | Nyce et al. |
| 2014/0178788 A1 | 6/2014 | Ha et al. |
| 2014/0194663 A1 | 7/2014 | Butler |
| 2014/0249339 A1 | 9/2014 | Simanzhenkov et al. |
| 2014/0274671 A1 | 9/2014 | Schammel et al. |
| 2014/0332733 A1 | 11/2014 | Joo et al. |
| 2014/0378728 A1 | 12/2014 | Davis et al. |
| 2015/0010467 A1 | 1/2015 | Ito et al. |
| 2015/0073192 A1 | 3/2015 | Cizeron et al. |
| 2015/0087875 A1 | 3/2015 | Zurcher et al. |
| 2015/0125383 A1 | 5/2015 | Yamazaki et al. |
| 2015/0224482 A1 | 8/2015 | Cizeron et al. |
| 2015/0314267 A1 | 11/2015 | Schammel et al. |
| 2016/0074844 A1 | 3/2016 | Freer et al. |
| 2016/0107143 A1 | 4/2016 | Schammel et al. |
| 2016/0122261 A1 | 5/2016 | Schammel et al. |
| 2016/0340272 A1 | 11/2016 | Cizeron et al. |
| 2017/0267605 A1 | 9/2017 | Tanur et al. |
| 2017/0275217 A1 | 9/2017 | Weinberger et al. |
| 2017/0283345 A1 | 10/2017 | Schammel et al. |
| 2017/0341997 A1 | 11/2017 | Nyce et al. |
| 2018/0093931 A1 | 4/2018 | Schammel et al. |
| 2018/0117570 A1 | 5/2018 | Freer et al. |
| 2018/0117579 A1 | 5/2018 | Scher et al. |
| 2018/0118637 A1 | 5/2018 | Zurcher et al. |
| 2018/0311658 A1 | 11/2018 | Liang et al. |
| 2019/0010096 A1 | 1/2019 | Schammel et al. |
| 2019/0022626 A1 | 1/2019 | Schammel et al. |
| 2019/0077728 A1 | 3/2019 | Cizeron et al. |
| 2020/0016580 A1 | 1/2020 | Freer et al. |
| 2020/0017423 A1* | 1/2020 | Tanur ............... B01J 35/02 |
| 2020/0024214 A1 | 1/2020 | Cizeron et al. |
| 2020/0070136 A1 | 3/2020 | Scher et al. |
| 2020/0109094 A1 | 4/2020 | Nyce et al. |
| 2020/0238256 A1 | 7/2020 | Zurcher et al. |

FOREIGN PATENT DOCUMENTS

| | | |
|---|---|---|
| CN | 1087291 A | 6/1994 |
| CN | 1100669 A | 3/1995 |
| CN | 1321728 A | 11/2001 |
| CN | 1389293 A | 1/2003 |
| CN | 1403375 A | 3/2003 |
| CN | 101 224 432 A | 7/2008 |
| CN | 101 387 019 A | 3/2009 |
| CN | 101495429 A | 7/2009 |
| CN | 102 125 825 A | 7/2011 |
| CN | 103118777 A | 5/2013 |
| DE | 3406751 A1 | 8/1985 |
| EP | 0 189 079 A1 | 7/1986 |
| EP | 0 253 522 A2 | 1/1988 |
| EP | 0 595 425 A1 | 5/1994 |
| EP | 0 761 307 B1 | 2/2003 |
| EP | 0 764 467 B1 | 2/2003 |
| EP | 1 632 467 A1 | 3/2006 |
| EP | 1 749 807 A1 | 2/2007 |
| EP | 2 287 142 A1 | 2/2011 |
| EP | 2 374 526 A1 | 10/2011 |
| FR | 649 429 A | 12/1928 |
| GB | 2 191 212 A | 12/1987 |
| GB | 2485461 A | 5/2012 |
| JP | 63-63626 A | 3/1988 |
| JP | 2-218623 A | 8/1990 |
| JP | 3-262535 A | 11/1991 |
| JP | 5-238961 A | 9/1993 |
| JP | 2005 161225 A | 6/2005 |
| JP | 2011-32257 A | 2/2011 |
| RU | 2 134 675 C1 | 8/1999 |
| WO | 86/007351 A1 | 12/1986 |
| WO | 98/14322 A1 | 4/1998 |
| WO | 00/016901 A1 | 3/2000 |
| WO | 02/080280 A1 | 10/2002 |
| WO | 2004/033488 A2 | 4/2004 |
| WO | 2005/067683 A2 | 7/2005 |
| WO | 2007/130515 A2 | 11/2007 |
| WO | 2008/005055 A2 | 1/2008 |
| WO | 2008/014841 A1 | 2/2008 |
| WO | 2008/022147 A1 | 2/2008 |
| WO | 2008/073143 A2 | 6/2008 |
| WO | 2009/071463 A2 | 6/2009 |
| WO | 2009/115805 A1 | 9/2009 |
| WO | 2010/005453 A2 | 1/2010 |
| WO | 2011/050359 A1 | 4/2011 |
| WO | 2011/149996 A2 | 12/2011 |
| WO | 2012/162526 A2 | 11/2012 |
| WO | 2013/082318 A2 | 6/2013 |
| WO | 2013/177433 A2 | 11/2013 |
| WO | 2013/186789 A1 | 12/2013 |
| WO | 2014/043603 A1 | 3/2014 |
| WO | 2014/049445 A2 | 4/2014 |

OTHER PUBLICATIONS

Agapie, "Selective ethylene oligomerization: recent advances in chromium catalysis and mechanistic investigations" *Coord Chem Rev* 255:861-880, 2011.

Au et al., "A Comparison of $BaF_2/La_2O_3$ and $BaBr_2/La_2O_3$ Catalysts for the Oxidative Coupling of Methane," *Journal of Catalysis* 159:280-287, 1996.

Bergh et al. "Combinatorial heterogeneous catalysis: oxidative dehydrogenation of ethane to ethylene, selective oxidation of ethane to acetic acid, and selective ammoxidation of propane to acrylonitrile" *Topics in Catalysis* 23:65-79, 2003.

Carter et al. "High activity ethylene trimerisation catalysts based on diphosphine ligands." *Chem Commun.*, pp. 858-859, 2002.

(56) References Cited

OTHER PUBLICATIONS

Cavani et al., "Oxidative dehydrogenation of ethane and propane: How far from commercial implementation?" *Catalysis Today* 127:113-131, 2007.
Choudhary et al., "Oxidative Coupling of Methane and Oxidative Dehydrogenation of Ethane over Strontium-Promoted Rare Earth Oxide Catalysts," *J. Chem. Technol. Biotechnol.* 71:167-172, 1998.
Choudhary et al., "Oxidative Coupling of Methane over SrO Deposited on Different Commercial Supports Precoated with $La_2O_3$," *Ind Eng Chem Res* 37:2142-2147, 1998.
Choudhary et al., "Oxidative conversion of methane/natural gas into higher hydrocarbons," *Catalysis Surveys from Asia* 8:15-25, 2004.
Choudhary et al., "Surface Basicity and Acidity of Alkaline Earth-Promoted $La_2O_3$ Catalysts and Their Performance in Oxidative Coupling of Methane," *J. Chem. Technol. Biotechnol.* 72:125-130, 1998.
Choudhary, et al., "Aromatization of dilute ethylene over Ga-modified ZSM-5 type zeolite catalysts," *Microporous and Mesoporous Materials* 47:253-267, 2001.
Christopher et al., "Engineering Selectivity in Heterogeneous Catalysis: Ag Nanowires as Selective Ethylene Epoxidation Catalysts," *J. Am. Chem. Soc.* 130:11264-11265, 2008.
Cizeron et al., "Catalysts for Petrochemical Catalysis," filed May 24, 2011, for U.S. Appl. No. 61/489,651, 86 pages.
Cizeron et al., "Catalysts for Petrochemical Catalysis," filed Nov. 29, 2011, for U.S. Appl. No. 61/564,832, 178 pgs.
Cizeron et al., "Catalytic Forms and Formulations," filed May 23, 2013, for U.S. Appl. No. 13/901,319, 132 pages.
Cizeron et al., "Catalysts for Petrochemical Catalysis," U.S. Appl. No. 14/692,495, filed Apr. 21, 2015, 211 pages.
Dai, "Study on low temperature catalytic activation of methane," Thesis of graduate student for Master's Degree in Physical Chemistry, East China Normal University, May 2005, 8 pages.
Débart et al., "$\alpha$-$MnO_2$ Nanowires: A Catalyst for the $O_2$ Electrode in Rechargeable Lithium Batteries," *Angew. Chem. Int. Ed.* 47:4521-4524, 2008.
Dedov et al., "Oxidative coupling of methane catalyzed by rare earth oxides Unexpected synergistic effect of the oxide mixtures," *Applied Catalysis* 245:209-220, 2003.
Devi et al., "College Inorganic Chemistry," Devi, K.V.S. Laxmi, Patel, N.C., and Venkatachalam, A.. College Inorganic Chemistry. Mumbai, IND: Himalaya Publishing House, 2010. Jan. 1, 2010 , XP055242276, Retrieved fron the Internet: URL:http://site.ebrary.com/lib/epo/reader.action?docID=10415159 [retried on Jan. 18, 2016] the whole document.
Dixon et al. "Advances in selective ethylene trimerisation—a critical overview" *J. Organometallic Chem.* 689:3641-3668, 2004.
Dulai et al. "N,N"-Bisdiaminophenylphosphine Ligands for Chromium-Catalyzed Selective Ethylene Oligomerization Reactions" *Organometallics* 30:935-941, 2011.
Enger et al., "A review of catalytic partial oxidation of methane to synthesis gas with emphasis on reaction mechanisms over transition metal catalysts," *Applied Catalysis A: General* 346:1-27, 2008.
Eskendirov et al., "Methane oxidative coupling on the $Au/La_2O_3/CaO$ catalyst in the presence of hydrogen peroxide," *Catalysis Letters* 35:33-37, 1995.
Fallah et al., "A New Nano-($2Li_2O/MgO$) Catalyst/Porous Alpha-Alumina Composite for the Oxidative Coupling of Methane Reaction" *AIChE Journal* 56:717-728, 2010.
Ferreira et al., "Effect of Mg, Ca and Sr on $CeO_2$ Based Catalysts for the Oxidative Coupling of Methane: Investigation on the Oxygen Species Responsible for Catalytic Performance," *Industrial & Engineering Chemistry Research* 51:10535-10541, 2012.
Freer et al., "Catalysts for Natural Gas Processes" U.S. Appl. No. 14/856,177, filed Sep. 16, 2015, 183 pages.
Galadima et al. "Revisiting the oxidative coupling of methane to ethylene in the golden period of shale gas: A review" *J Ind Eng Chem* . http://dx.doi.org/10.1016/j.jiec.2016.03.027.

Gao et al., "A study on methanol steam reforming to $CO_2$ and $H_2$ over the $La_2CuO_4$ nanofiber catalyst," *Journal of Solid State Chemistry* 181:7-13, 2008.
Gao et al., "The direct decomposition of NO over the $La_2CuO_4$ nanofiber catalyst," *Journal of Solid State Chemistry* 181:2804-2807, 2008.
Gong et al., "Preparation of Carbon Nanotubes—Cordierite Monoliths of Catalytic Chemical Vapor Deposition as Catalyst Supports for Ammonia Synthesis," *Catalysis Letters* 122:287-294, 2008.
Guo et al., "Direct, Nonoxidative Conversion of Methane to Ethylene, Aromatics, and Hydrogen" *Science* 344:616-619, 2014.
Hess et al. , "Kirk-Othmer encyclopedia of chemical technology." New York, John Wiley & Sons Ltd., 1998, p. 171.
Hinson et al., "The Oxidative Coupling of Methane on Chlorinated Lithium-Doped Magnesium Oxide" *J Chem Soc, Chem Comm* 20:1430-1432, 1991.
Huang et al., "Exploiting Shape Effects of $La_2O_3$ Nanocatalysts for Oxidative Coupling of Methane Reaction," *The Royal Society of Chemistry*, 2013. (5 pages).
Huang et al., "Exploiting Shape Effects of La2O3 Nanocatalysts for Oxidative Coupling of Methane Reaction," *The Royal Society of Chemistry*, 2013. (7 pages).
Istadi et al., "Synergistic effect of catalyst basicity and reducibility on performance of ternary CeO2-based catalyst for CO2 OCM to C2 hydrocarbons," *Journal of Molecular Catalysis A: Chemical* 259:61-66, 2006.
Jaramillo et al., "Comparative Analysis of the Production Costs and Life-Cycle GHG Emissions of FT Liquid Fuels from Coal and Natural Gas" *Env. Sci. Tech* 42:7559-7565, 2008.
Jiangrong et al., "Preparation and Characterization of $La_2O_2CO_3$ Nanowires with High Surface Areas," *Journal of The Chinese Rare Earth Society* 23:33-36, 2005.
Kaminsky et al. "Deactivation of Li-Based Catalysts for Methane Oxidative Coupling" Symposium on Natural Gas Upgrading II, Presented before The Division of Petroleum Chemistry, Inc., The American Chemical Society, San Francisco, CA, Apr. 5-10, 1992.
Kaminsky et al., "Oxygen X-Ray Absorption Near-Edge Structure Characterization of the Ba-Doped Yttria Oxidative Coupling Catalyst" *J Catalysis* 136:16-23, 1992.
Keller et al., "Synthesis of Ethylene via Oxidative Coupling of Methane," *Journal of Catalysis* 73:9-19, 1982.
Krishnadas et al., "Pristine and Hybrid Nickel Nanowires: Template-, Magnetic Field-, and Surfactant-Free Wet Chemical Synthesis and Raman Studies," *The Journal of Physical Chemistry* 115:4483-4490, 2011.
Kuang et al., "Grafting of PEG onto lanthanum hydroxide nanowires," *Materials Letters* 62:4078-4080, 2008.
Labinger, "Oxidative Coupling of Methane: An Inherent Limit to Selectivity?" *Catalysis Letters* 1:371-376, 1988.
Li et al., "Color control and white light generation of upconversion luminescence by operating dopant concentrations and pump densities in $YB^{3+}$, $Er^{3+}$ and $Tm^{3+}$ tri-doped $Lu_2O_3$ nanocrystals," *J. Mater. Chem.* 21:2895-2900, 2011.
Ling et al., "Preparation of $Ag_{core}Au_{shell}$ Nanowires and Their Surface Enhanced Raman Spectroscopic Studies," *Acta Chimica Sinica* 65:779-784, 2007.
Liu et al., "A novel $Na_2WO_4$—Mn/SiC monolithic foam catalyst with improved thermal properties for the oxidative coupling of methane," *Catalysis Communications* 9:1302-1306, 2007.
Lunsford, "The Catalytic Oxidative Coupling of Methane," *Angew. Chem. Int. Ed. Engl.* 34:970-980, 1995.
Ma et al., "Processing and properties of carbon nanotubes-nano-SiC ceramic," *Journal of Materials Science* 33:5243-5246, 1998.
Matskevich et al., "Synthesis and thermochemistry of new phase $BaCe_{0.7}Nd_{0.2}In_{0.1}O_{2.85}$," *Journal of Alloys and Compounds* 577:148-151, 2013.
Miller et al., "Oxidation reactions of ethane over Ba—Ce—O based perovskites," *Applied Catalysis A* 201:45-54, 2000.
Mleczko et al., "Catalytic oxidative coupling of methane—reaction engineering aspects and process schemes," *Fuel Processing Technology* 42:217-248, 1995.

(56) References Cited

OTHER PUBLICATIONS

Nagamoto et al., "Methane Oxidation over Perovskite-type Oxide Containing Alkaline-earth Metal," *Chemistry Letters*, 237-240, 1988.

Nam et al., "Virus-Enabled Synthesis and Assembly of Nanowires for Lithium Ion Battery Electrodes," *Science* 312:885-888, 2006.

Natural Gas Spec Sheet, prepared by Florida Power and Light Company, 2003.

Neltner et al., "Production of Hydrogen Using Nanocrystalline Protein-Templated Catalysts on M13 Phage," *ACSNano* 4:3227-3235, 2010.

Neltner, "Hybrid Bio-templated Catalysts," Doctoral Thesis, Massachusetts Institute of Technology, Jun. 2010, 156 pages.

Nyce et al., "Polymer Templated Nanowire Catalysts," filed Nov. 29, 2011 for U.S. Appl. No. 61/564,836, 317 pgs.

O'Connor et al. "Alkene Oligomerization" *Catalysis Today* 6:329-349, 1990.

Pak et al., "Elementary Reactions in the Oxidative Coupling of Methane over $Mn/Na_2WO_4/SiO_2$ and $Mn/Na_2WO_4/MgO$ Catalysts," *Journal of Catalysis* 179:222-230, 1998.

Park et al., "Fabrication of metallic nanowires and nanoribbions using laser interference lithography and shadow lithography," *Nanotechnology* 21:1-6, 2010.

Peitz et al., "An Alternative Mechanistic Concept for Homogeneous Selective Ethylene Oligomerization of Chromium-Based Catalysts: Binuclear Metallacycles as a Reason for 1-Octene Selectivity?" *Chemistry—A European Journal* 16:7670-7676, 2010.

Qiu et al., "Steady-state conversion of methane to aromatics in high yields using an integrated recycle reaction system," *Catalysis Letters* 48:11-15, 1997.

Ren et al., "Basic petrochemicals from natural gas, coal and biomass: Energy use and $CO_2$ emissions" *Res Conserv Recycl* 53:513-528, 2009.

Ryu et al., "Preparation of Porous $LaFeO_3$ Nanowires using AAO Template and Their Catalytic Properties," *Bull. Korean Chem Soc.* 32:2457-2460, 2011.

Schaarschmidt et al., "Ferrocenyl phosphane nickel carbonyls: Synthesis, solid state structure, and their use as catalysts in the oligomerization of ethylene" *J. Organometallic Chem.* 695:1541-1549, 2010.

Schammel et al., "Catalysts for Petrochemical Catalysis," U.S. Appl. No. 14/777,333, filed Sep. 15, 2015, 259 pages.

Schammel et al., "Heterogeneous Catalysts," U.S. Appl. No. 14/701,963, filed May 1, 2015, 335 pages.

Schammel et al., "Catalysts for Petrochemical Catalysis," U.S. Appl. No. 61/794,486, filed Mar. 15, 2013, 217 pages.

Schammel et al., "Oxidative Coupling of Methane Systems and Methods," U.S. Appl. No. 13/900,898, filed May 23, 2013, 201 pages.

Schweer et al., "OCM in a fixed-bed reactor: limits and perspectives," *Catalysis Today* 21:357-369, 1994.

Somorjai et al., "High technology catalysts towards 100% selectivity Fabrication, characterization and reaction studies," *Catalysis Today* 100:201-215, 2005.

Song et al., "Synthesis, characterization and ethylene oligomerization behaviour of 8-quinaldinylnickel dihalides" *Catal. Sci. Technol.* 1:69-75, 2011.

Spinicci et al., "Oxidative coupling of methane on $LaAlO_3$ perovskites partially substituted with alkali or alkali-earth ions," *Journal of Molecular Catalysis A; Chemical* 176:253-265, 2001.

Takanabe et al., "Mechanistic Aspects and eaction Pathways for Oxidative Coupling of Methane on $Mn/Na_2WO_4/SiO_2$ Catalysts," *J. Phys. Chem. C* 113:10131-10145, 2009.

Takanabe et al., "Rate and Selectivity Enhancements Mediated by OH Radicals in the Oxidative Coupling of Methane Catalyzed by $Mn/Na_2WO_4/SiO_2$," *Angew. Chem. Int. Ed.* 47:7689-7693, 2008.

Tana et al., "Morphology-dependent redox and catalytic properties of $CeO_2$ nanostructures: Nanowires, nanorods and nanoparticles," *Catalysis Today* 148:179-183, 2009.

Tanaka et al., "Oxidative Coupling of Methane over Ba_incorporated $LaInO_3$ Perovskite Catalyst," *Journal of the Japan Petroleum Institute* 55:71-72, 2012.

Taylor et al., "Lanthanum Catalysts for $CH_4$ Oxidative Coupling: A Comparison of the Reactivity of Phases," *Ind. Eng. Chem. Res.* 30:1016-1023, 1991.

Teymouri et al., "Reactivity of perovskites on oxidative coupling of methane," *Journal of Materials Science* 30:3005-3009, 1995.

Theuerkauf et al., "Analysis of particle porosity distribution in fixed beds using the discrete element method," *Powder Technology* 165:92-99, 2006.

Tian et al., "Catalytic reduction of $No_x$ with $NH_3$ over different-shaped $MnO_2$ at low temperature," *Journal of Hazardous Materials* 188:105-109, 2011.

Tomishige et al., "Reactivity and characterization of absorbed oxygen on $SrTi_{1-x}Mg_xO_{3-\delta}$ scatalysts for oxidative coupling of methane," *Phys. Chem. Chem. Phys.* 1:3039-3045, 1999.

Tong et al., "Development Strategy Research of Downstream Products of Ethene in Tianjin," *Tianjin Economy*, pp. 37-40, 1996.

Trautmann et al., "Cyrogenic Technology for Nitrogen Rejection from Variable Content Natural Gas," *XIV Convencion Internacional de Gas*, Caracas, Venezuela May 10-12, 2000.

Tullo, "Ethylene from Methane," *Chemical and Engineering News* 89:20-21, 2011.

Valenzuela et al., "Nanostructured ceria-based catalysts for oxydehydrogenation of ethane with $CO_2$, " *Topics in Catalysis* 15:181-188, 2001.

Van Santen et al., "An Introduction to Molecular Heterogeneous Catalysis" *New Trends in Material Chemistry*, pp. 345-362, 1997.

Wang et al., "Autothermal oxidative coupling of methane on the $SrCO3/Sm2O3$ catalysts," *Catalysis Communications* 10:807-810, 2009.

Wang et al., "Low-temperature selective oxidation of methane to ethane and ethylene over $BaCO3/La2O3$ catalysts prepared by urea combustion method," *Catalysis Communications* 7:59-63, 2006.

Wang et al., "Nanostructured Sheets of Ti—O Nanobelts for Gas Sensing and Antibacterial Applications, " *Advanced Functional Materials* 18:1131-1137, 2008.

Wang et al., "Synthesis and Characterization of Lanthanide Hydroxide Single-Crystal Nanowires" *Angew Chem Int Ed* 41:4790-4793, 2002.

Wang et al., "Comparative study on oxidation of methane to ethane and ethylene over $Na_2WO_4$—$Mn/SiO_2$ catalysts prepared by different methods," *Journal of Molecular Catalysis A: Chemical* 245:272-277, 2006.

Wong et al., "Oxidative Coupling of Methane Over Alkali Metal Oxide Promoted $LA_2O_3/BACO_3$ Catalysts," *Journal of Chemical Technology and Biotechnology* 65:351-354, 1996.

Yang et al., "Anisotropic syntheses of boat-shaped core-shell Au—Ag nanocrystals and nanowires," *Nanotechnology* 17:2304-2310, 2006.

Yu et al., "Oxidative Coupling of Methane over Acceptor-doped $SrTiO_3$: Correlation between p-type Conductivity and $C_2$ Yield," *Journal of Catalysis* 13:338-344, 1992.

Yun et al., "Current Status and Some Perspectives of Rare Earth Catalytic Materials," *Journal of The Chinese Rare Earth Society* 25:1-15, 2007.

Zhang et al., "Relationship between packing structure and porosity in fixed beds of equilateral cylindrical particles," *Chemical Engineering Science* 61:8060-8074, 2006.

Zhang et al., "Single-Walled Carbon Nanotube-Based Coaxial Nanowires: Synthesis, Characterization, and Electrical properties," *J Phys Chem* 109(3):1101-1107, 2005.

Zhang et al., "Recent Progress in Direct Partial Oxidation of Methane to Methanol," *Journal of Natural Gas Chemistry* 12:81-89, 2003.

Zhao, "Technologies and Catalysts for Catalytic Preparation of Ethene," *Industrial Catalysis* 12:285-289, 2004.

Zhou et al., "Functionalization of lanthanum hydroxide nanowires by atom transfer radical polymerization," *Nanotechnology* 18:405704, 2007.

(56) References Cited

OTHER PUBLICATIONS

Zhu et al. "Recent Research Progress in Preparation of Ethylene Oligomers with Chromium-Based Catalytic Systems" *Designed Monomers & Polymers* 14:1-23, 2011.

Zimmermann et al., "Ethylene," *Ullmann's Encyclopedia of Industrial Chemistry*, Wiley-VCH Verlag GmbH & Co. KGaA, Weinheim, Germany, 2009. (66 pages).

Zurcher et al., "Nanowire Catalysts," filed May 24, 2012, for U.S. Appl. No. 61/651,399, 406 pages.

Zurcher et al., "Nanowire Catalysts," filed Nov. 29, 2011, for U.S. Appl. No. 61/564,834, 367 pages.

U.S. Appl. No. 16/986,065, filed Aug. 5, 2020.

Norby et al., "Protons in Ca-doped $La_2O_3$, $Nd_2O_3$ and $LaNdO_3$," *Solid State Ionics* 53-56:446-452, 1992.

Choudhary et al., "Oxidative coupling of methane over alkaline earth oxides deposited on commercial support precoated with rare earth oxides," *Fuel* 78:427-437, 1999.

Yun et al., "Current Status and Some Perspectives of Rare Earth Catalytic Materials," *Journal of the Chinese Rare Earth Society* 25:1-15, 2007. (with English Abstract).

U.S. Appl. No. 16/777,352, filed Jan. 30, 2020.

U.S. Appl. No. 16/834,972, filed Mar. 30, 2020.

Noon et al., "Oxidative coupling of methane with $La_2O_3$—$CeO_2$ nanofiber fabrics: A reaction engineering study," *Journal of Natural Gas Science and Engineering* 18:406-411, 2014.

Ekstrom et al., "Effect of Pressure on the Oxidative Coupling Reaction of Methane," *Applied Catalysis* 62:253-269, 1990.

\* cited by examiner

CATALYSTS FOR NATURAL GAS PROCESSES

BACKGROUND

Technical Field

This invention is generally related to catalysts and catalytic forms and formulations for use in natural gas processes, such as the oxidative coupling of methane.

Description of the Related Art

Catalysis is the process in which the rate of a chemical reaction is either increased or decreased by means of a catalyst. Positive catalysts lower the rate-limiting free energy change to the transition state, and thus increase the speed of a chemical reaction at a given temperature. Negative catalysts have the opposite effect. Catalysts are generally characterized as either heterogeneous or homogeneous. Heterogeneous catalysts exist in a different phase than the reactants (e.g., a solid metal catalyst and gas phase reactants), and the catalytic reaction generally occurs on the surface of the heterogeneous catalyst. Thus, for the catalytic reaction to occur, the reactants must diffuse to and/or adsorb onto the catalyst surface. This transport and adsorption of reactants is often the rate limiting step in a heterogeneous catalysis reaction. Heterogeneous catalysts are also generally easily separable from the reaction mixture by common techniques such as filtration or distillation.

One heterogeneous catalytic reaction with commercial potential is the oxidative coupling of methane ("OCM") to ethylene: $2CH_4 + O_2 \rightarrow C_2H_4 + 2H_2O$. See, e.g., Zhang, Q., *Journal of Natural Gas Chem.*, 12:81, 2003; Olah, G. "Hydrocarbon Chemistry", Ed. 2, John Wiley & Sons (2003). This reaction is exothermic ($\Delta H = -67$ kcals/mole) and has typically been shown to occur at very high temperatures (>700° C.). Although the detailed reaction mechanism is not fully characterized, experimental evidence suggests that free radical chemistry is involved. (Lunsford, *J. Chem. Soc., Chem. Comm.,* 1991; H. Lunsford, *Angew. Chem., Int. Ed. Engl.,* 34:970, 1995). In the reaction, methane ($CH_4$) is activated on the catalyst surface, forming methyl radicals which then couple in the gas phase to form ethane ($C_2H_6$), followed by dehydrogenation to ethylene ($C_2H_4$). To date, the OCM reaction has not been commercialized, due in large part to the lack of effective catalysts and catalytic forms.

Another catalytic reaction with commercial potential is the oxidative dehydrydrogenation (ODH) of ethane to ethylene. Oxidative dehydrogenation of ethane to ethylene has been proposed to replace thermal cracking of ethane. The lower temperature operation and exothermic nature of ODH has the potential to significantly reduce the external heat input required for thermal cracking and lessen the coke formation. However, over oxidation of ethylene can reduce the ethylene selectivity, and better catalysts and processes are needed before the full potential of this reaction can be realized.

Many heterogeneous catalysts are employed in combination with a binder, carrier, diluent, support material and/or are provided in specific shapes or sizes. The use of these materials provides certain advantages. For example, supports provide a surface on which the catalyst is spread to increase the effective surface area of the catalyst and reduce the catalyst load required. The support or diluent may also interact synergistically with the catalyst to enhance the catalytic properties of the catalyst. Further, catalytic supports may be tailored to specific reactions and/or reactor types in order to optimize the flow (e.g., reduce back pressure) of gaseous reactants.

While some progress has been made, there remains a need in the art for improved catalysts, catalyst forms and formulations and catalytic processes for use in catalytic reactions, such as OCM and ODH. The present invention fulfills these needs and provides further related advantages.

BRIEF SUMMARY

In brief, catalysts, catalytic forms and formulations and related methods are disclosed. In one embodiment, the disclosure provides a catalytic material comprising a plurality of catalysts in combination with a diluent or support, for example in some embodiments the catalysts are catalytic nanowires. The catalytic materials find utility in various catalytic reactions. In one particular embodiment, the catalytic materials are useful for petrochemical catalysis, such as the oxidative coupling of methane or the oxidative dehydrogenation of alkanes to olefins (e.g., ethane to ethylene, propane to propene, butane to butene and the like).

In one embodiment, the disclosure provides a formed catalytic material comprising:
(a) a perovskite; and
(b) a catalyst having the following formula:

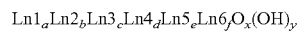
$Ln1_a Ln2_b Ln3_c Ln4_d Ln5_e Ln6_f O_x(OH)_y$ wherein:
Ln1, Ln2, Ln3, Ln4, Ln5 and Ln6 are each independently different lanthanide elements;
O is oxygen;
OH is hydroxy;
a is a number greater than 0; and
b, c, d, e, f, x and y are each independently numbers of 0 or greater, provided that at least one of x or y is greater than 0,
wherein the catalytic material further comprises a methane conversion of greater than 20% and a C2 selectivity of greater than 50% when the catalyst is employed as a heterogeneous catalyst in the oxidative coupling of methane at a temperatures ranging from about 550° C. to about 750° C.

In a different embodiment, the disclosure is directed to a catalytic material comprising:
(a) an OCM active catalyst; and
(b) a second catalyst comprising the following formula:

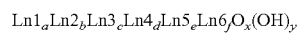
$Ln1_a Ln2_b Ln3_c Ln4_d Ln5_e Ln6_f O_x(OH)_y$ wherein:
Ln1, Ln2, Ln3, Ln4, Ln5 and Ln6 are each independently different lanthanide elements;
O is oxygen;
OH is hydroxy;
a is a number greater than 0; and
b, c, d, e, f, x and y are each independently numbers of 0 or greater, provided that at least one of x or y is greater than 0
wherein the OCM active catalyst comprises a methane conversion of greater than 20% and a C2 selectivity of greater than 50% when the catalyst is employed as a heterogeneous catalyst in the oxidative coupling of methane at a temperatures ranging from about 550° C. to about 750° C., and wherein the OCM activity of the catalytic material is greater than either (a) or (b) alone.

In other embodiments is provided a catalytic material comprising:
(a) an alkaline earth metal aluminate, tungstate, titanate, zirconate or hafnate; and
(b) a catalyst having the following formula:

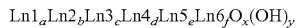

wherein:
Ln1, Ln2, Ln3, Ln4, Ln5 and Ln6 are each independently different lanthanide elements;
O is oxygen;
OH is hydroxy;
a is a number greater than 0; and
b, c, d, e, f, x and y are each independently numbers of 0 or greater, provided that at least one of x or y is greater than 0.

Still more embodiments are directed to a catalytic material comprising:
(a) an OCM active catalyst; and
(b) a second catalyst comprising the following formula:

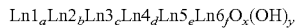

wherein:
Ln1, Ln2, Ln3, Ln4, Ln5 and Ln6 are each independently different lanthanide elements;
O is oxygen;
OH is hydroxy;
a is a number greater than 0; and
b, c, d, e, f, x and y are each independently numbers of 0 or greater, provided that at least one of x or y is greater than 0
wherein the catalytic material has a volume loss of less than 5% when heated to 900° C. in air for 100 hours.

In other more embodiments, a formed catalyst is provided, the formed catalyst comprising a nanostructured catalyst base material and a dopant, wherein the catalyst has a crush strength of greater than about 2 N/mm after exposure to air comprising water at temperatures between about 20° C. and 30° C. for greater than 50 hours.

In different embodiments, the disclosure is directed to a formed catalytic material for performing oxidative coupling of methane at linear velocities ranging from about 0.1 m/s to about 10 m/s, the catalytic material comprising:
a) a catalyst
b) a non-tessellating shape;
c) a binder or diluent;
d) a crush strength of greater than about 2 N/mm after exposure to air comprising water at temperatures between about 20° C. and 30° C. for greater than 50 hours; and
d) a bed void fraction of greater than 0.3. 114.

A catalyst bed comprising a plurality of the foregoing catalytic materials is also provided in different embodiments.

Other embodiments provide a catalytic material comprising a first and second catalyst, wherein the first catalyst has activity for oxidative coupling of methane, and the second catalyst has activity for oxidation of carbon monoxide.

Other embodiments are directed to a formed catalytic material comprising a plurality of nanostructured catalysts tableted or extruded into a form, the catalytic material having a density ranging from about 2.0 g/mL to about 5.0 g/mL, a porosity ranging from about 0.7 to about 0.2 and a surface area ranging from about 30 m²/g to about 0.2 m²/g.

In still more embodiments, a formed catalytic material comprising an OCM active catalyst is provided, wherein the catalytic material is in the shape of a ring having an outer diameter ranging from about 3 mm to about 50 mm and an inner diameter ranging from about 1 mm to about 25 mm, wherein the outer diameter is larger than the inner diameter.

A formed catalytic material comprising an OCM active catalyst is provided in various other embodiments, wherein the catalytic material comprises a non-tessellating shape having a plurality of penetrating holes therethrough.

In more embodiments, the disclosure is directed to a formed catalytic material comprising a plurality of OCM active catalysts, wherein the catalytic material has a C2+ selectivity of greater than 50% when the catalytic material is employed as a catalytic material in a method for the oxidative coupling of methane to C2+ hydrocarbons, wherein the method comprises passing a feed gas comprising methane though the catalytic material at linear velocities ranging from about 0.1 m/s to about 10 m/s.

In some other different embodiments, the disclosure provides a formed catalytic material for performing oxidative coupling of methane at linear velocities ranging from about 0.1 m/s to about 10 m/s, the catalytic material comprising (a) a catalyst and a binder or diluent; (b) a non-tessellating shape; and (c) at least one rounded or chamfered edge, at least one convex surface or both, wherein the catalytic material comprises a methane conversion of greater than 20% and a C2 selectivity of greater than 50% when the catalytic material is employed as a heterogeneous catalyst in the oxidative coupling of methane at a temperatures ranging from about 550° C. to about 750° C.

Methods for preparing catalysts and catalytic materials are also provided. Accordingly, in one embodiment a method for preparing a catalyst comprising a dopant is provided, the method comprising: (a) preparing a mixture comprising a nanostructured catalyst base material and a salt of the dopant, wherein the salt comprises at least 95% w/w of a carbonate salt of the dopant; and (b) calcining the mixture above about 300° C., and (c) forming the formed catalyst by tableting or extrusion, wherein the catalyst has a crush strength of greater than about 2 N/mm after exposure to air comprising water at temperatures between about 20° C. and 30° C. for greater than 50 hours. Catalyst prepared by the foregoing method are also provided.

In still different embodiments, a method for preparation of a formed catalytic material for the oxidative coupling of methane is provided, the method comprising:
a) admixing a nanostructured catalytic base material;
b) extruding or tableting the mixture of (a) to prepare a formed catalytic material; and
c) calcining the formed catalytic material at temperatures ranging from about 600° C. to about 1200° C.

Other embodiments are directed to a method for preparation of a formed catalytic material for the oxidative coupling of methane, the method comprising:
a) forming a nanostructured catalytic base material by: (i) admixing a nanostructured catalyst with a dopant; (ii) drying the doped nanostructured catalyst of (i); (iii) milling the dried nanostructured catalyst of (ii); and (iv) calcining the milled nanostructured catalyst of (iii) at temperatures ranging from about 600° C. to about 1200° C. to produce the nanostructured catalytic base material;
b) extruding or tableting the mixture of (a) to prepare a formed catalytic material; and
c) calcining the formed catalytic material at temperatures ranging from about 600° C. to about 1200° C.

Methods for performing catalytic reactions, such as the oxidative coupling of methane are also provided in various embodiments. For example, in one embodiment is provided a method for performing a catalytic reaction, the method comprising contacting a composition comprising a molten salt and a catalyst with a reactant gas, thereby converting the reactant gas to a product gas. Compositions comprising a molten salt and a catalyst suspended therein are also provided.

Other different embodiments provide a method for the preparation of an alkene, the method comprising charging a feed gas comprising an alkane and oxygen through an inlet to a reactor comprising a fluidized catalyst bed, and contacting the feed gas with the fluidized catalyst bed for a period of time sufficient to convert the alkane to the alkene, wherein the temperature of the feed gas at the inlet is maintained at or below 550° C., and the fluidized catalyst bed is maintained at temperatures ranging from 650° C. to 950° C.

In still more different embodiments, a method of the oxidative coupling of methane is provided, the method comprising contacting a mixture comprising methane and oxygen with a catalyst bed comprising any of the catalytic materials described herein at gas linear velocities ranging from about 0.1 m/s to about 10 m/s.

In other embodiments, the disclosure provides a method for oxidative coupling of methane, the method comprising contacting methane and oxygen with any of the catalytic materials described herein at temperatures ranging from about 525° C. to about 825° C. to form a product gas comprising C2's, carbon dioxide and substantially no carbon monoxide.

More different embodiments provide a method for oxidative coupling of methane, the method comprising:

a) contacting methane and oxygen with an OCM active catalyst to form a product gas; and b) contacting the product gas in a downstream reactor with a second catalyst that has activity for oxidation of carbon monoxide.

In other embodiments, a method for the oxidative coupling of methane to C2+ hydrocarbons under adiabatic conditions is provided, the method comprising passing a feed gas comprising methane at a linear velocity of 0.1 m/s or higher through a packed catalyst bed, the packed catalyst bed comprising any of the catalytic materials described herein.

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE SEVERAL VIEWS OF THE DRAWINGS

In the drawings, the sizes and relative positions of elements in the drawings are not necessarily drawn to scale. For example, the various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been selected solely for ease of recognition in the drawings.

DETAILED DESCRIPTION

Figure 1:
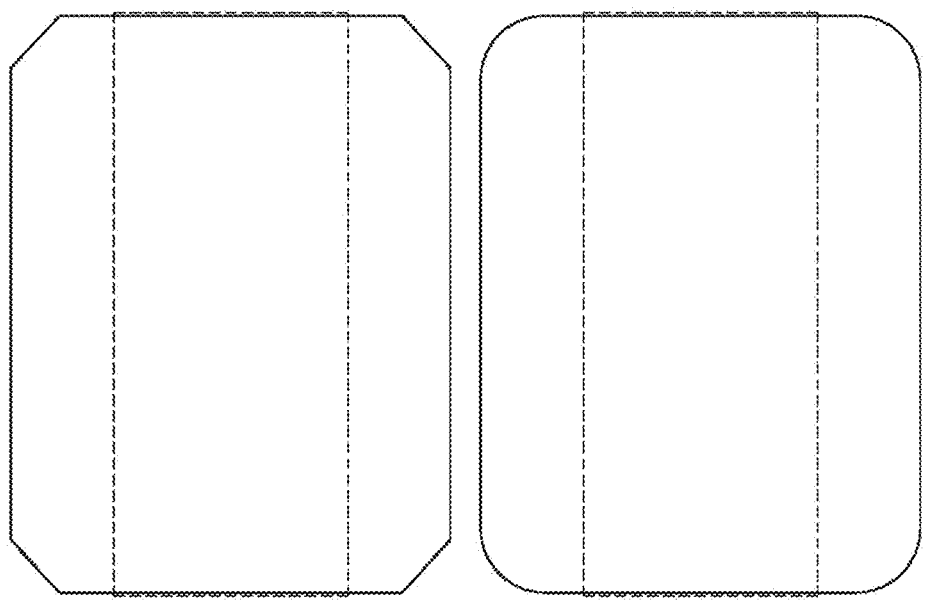
FIG. 1 presents exemplary catalytic material shapes having chamfered (left) or rounded (right) edges.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or"

is generally employed in its sense including "and/or" unless the content clearly dictates otherwise.

Definitions

As used herein, and unless the context dictates otherwise, the following terms have the meanings as specified below.

"Catalyst" means a substance that alters the rate of a chemical reaction. A catalyst may either increase the chemical reaction rate (i.e., a "positive catalyst") or decrease the reaction rate (i.e., a "negative catalyst"). Catalysts participate in a reaction in a cyclic fashion such that the catalyst is cyclically regenerated. "Catalytic" means having the properties of a catalyst.

"Catalytic material" refers to a plurality of catalyst particles, which may optionally be combined with a support, diluent and/or binder.

"Catalyst form" or "catalytic form" refers to the physical shape of a catalytic material. For example, catalyst forms include catalysts and/or catalytic materials extrudated or pelleted into various shapes or disposed on various support structures, including honeycomb structures, grids, monoliths, and the like, as discussed in more detail below.

"Catalyst formulation" or "catalytic formulation" refers to the chemical composition of a catalytic material. For example, a catalyst formulation may include a catalyst and one or more support, diluent and/or binder materials.

An "extrudate" refers to a material (e.g., catalytic material) prepared by forcing a semisolid material comprising a catalyst through a die or opening of appropriate shape. Extrudates can be prepared in a variety of shapes and structures by common means known in the art.

A "formed aggregate" or "formed catalytic material" refers to an aggregation of catalyst material particles, either alone, or in conjunction with one or more other materials, e.g., catalyst materials, dopants, diluents, support materials, binders, etc. formed into a single particle. Formed aggregates include without limitation, extruded particles, termed "extrudates", pressed or cast particles, e.g., pellets such as tablets, ovals, spherical particles, etc., coated particles, e.g., spray, immersion or pan coated particles, pan agglomerated particles, impregnated particles, e.g., monoliths, foils, foams, honeycombs, or the like. Formed aggregates may range in size from particles having individual cross sections in the micron range to cross sections in the millimeter range, to even larger particles such as monolithic formed aggregates, that may be on the order of centimeters or even meters in cross section.

A "pellet", "pressed pellet", "tablet" or "tableted" refers to a material (e.g., catalytic material) prepared by applying pressure to (i.e., compressing) a material comprising a catalyst into a desired shape. Pellets having various dimensions and shapes can be prepared according to common techniques in the art.

"Monolith" or "monolith support" is generally a structure formed from a single structural unit preferably having passages disposed through it in either an irregular or regular pattern with porous or non-porous walls separating adjacent passages. Examples of such monolithic supports include, e.g., ceramic or metal foam-like or porous structures. The single structural unit may be used in place of or in addition to conventional particulate or granular catalysts (e.g., pellets or extrudates). Examples of such irregular patterned monolith substrates include filters used for molten metals. Monoliths generally have a porous fraction ranging from about 60% to 90% and a flow resistance substantially less than the flow resistance of a packed bed of similar volume (e.g., about 10% to 30% of the flow resistance of a packed bed of similar volume). Examples of regular patterned substrates include monolith honeycomb supports used for purifying exhausts from motor vehicles and used in various chemical processes and ceramic foam structures having irregular passages. Many types of monolith support structures made from conventional refractory or ceramic materials such as alumina, zirconia, yttria, silicon carbide, and mixtures thereof, are well known and commercially available from, among others, Corning, Iac.; Vesuvius Hi-Tech Ceramics, Inc.; and Porvair Advanced Materials, Inc. and SiCAT (Sicatalyst.com). Monoliths include, but are not limited to, foams, honeycombs, foils, mesh, gauze and the like.

"Bulk catalyst" or "bulk material" refers to a catalyst without nanosized dimensions. For example, bulk catalysts and materials generally have dimensions of 100 nanometers or more. Such materials can be prepared, for example, by traditional techniques, for example by milling or grinding large catalyst particles to obtain smaller/higher surface area catalyst particles.

"Nanostructured catalyst" means a catalyst having at least one dimension on the order of nanometers (e.g., between about 1 and 100 nanometers). Non-limiting examples of nanostructured catalysts include nanoparticle catalysts and nanowire catalysts.

"Nanoparticle" means a particle having at least one diameter on the order of nanometers (e.g., between about 1 and 100 nanometers).

"Nanowire" means a nanowire structure having at least one dimension on the order of nanometers (e.g. between about 1 and 100 nanometers) and an aspect ratio greater than 10:1. The "aspect ratio" of a nanowire is the ratio of the actual length (L) of the nanowire to the diameter (D) of the nanowire. Aspect ratio is expressed as L:D. Exemplary nanowires are known in the art and described in more detail in co-pending U.S. application Ser. No. 13/115,082 (U.S. Pub. No. 2012/0041246); Ser. No. 13/689,611 (U.S. Pub. No. US-2013/0165728); and Ser. No. 13/689,514 (U.S. Pub. No. 2013/0158322), the full disclosures of which are hereby incorporated by reference in their entirety for all purposes.

"Polycrystalline nanowire" means a nanowire having multiple crystal domains. Polycrystalline nanowires often have different morphologies (e.g. bent vs. straight) as compared to the corresponding "single-crystalline" nanowires.

"Effective length" of a nanowire means the shortest distance between the two distal ends of a nanowire as measured by transmission electron microscopy (TEM) in bright field mode at 5 keV. "Average effective length" refers to the average of the effective lengths of individual nanowires within a plurality of nanowires.

"Actual length" of a nanowire means the distance between the two distal ends of a nanowire as traced through the backbone of the nanowire as measured by TEM in bright field mode at 5 keV. "Average actual length" refers to the average of the actual lengths of individual nanowires within a plurality of nanowires.

The "diameter" of a nanowire is measured in an axis perpendicular to the axis of the nanowire's actual length (i.e. perpendicular to the nanowires backbone). The diameter of a nanowire will vary from narrow to wide as measured at different points along the nanowire backbone. As used herein, the diameter of a nanowire is the most prevalent (i.e. the mode) diameter.

The "ratio of effective length to actual length" is determined by dividing the effective length by the actual length. A nanowire having a "bent morphology" will have a ratio of effective length to actual length of less than one as described in more detail herein. A straight nanowire will have a ratio of effective length to actual length equal to one as described in more detail herein.

"Inorganic" means a substance comprising a metal or semi-metal element. In certain embodiments, inorganic refers to a substance comprising a metal element. An inorganic compound can contain one or more metals in their elemental state, or more typically, a compound formed by a metal ion ($M^{n+}$, wherein n 1, 2, 3, 4, 5, 6 or 7) and an anion ($X^{m-}$, m is 1, 2, 3 or 4), which balance and neutralize the positive charges of the metal ion through electrostatic interactions. Non-limiting examples of inorganic compounds include oxides, hydroxides, halides, nitrates, sulfates, carbonates, phosphates, acetates, oxalates, and combinations thereof, of metal elements. Other non-limiting examples of inorganic compounds include $Li_2CO_3$, $Li_2PO_4$, $LiOH$, $Li_2O$, $LiCl$, $LiBr$, $LiI$, $Li_2C_2O_4$, $Li_2SO_4$, $Na_2CO_3$, $Na_2PO_4$, $NaOH$, $Na_2O$, $NaCl$, $NaBr$, $NaI$, $Na_2C_2O_4$, $Na_2SO_4$, $K_2CO_3$, $K_2PO_4$, $KOH$, $K_2O$, $KCl$, $KBr$, $KI$, $K_2C_2O_4$, $K_2SO_4$, $Cs_2CO_3$, $CsPO_4$, $CsOH$, $Cs_2O$, $CsCl$, $CsBr$, $CsI$, $CsC_2O_4$, $CsSO_4$, $Be(OH)_2$, $BeCO_3$, $BePO_4$, $BeO$, $BeCl_2$, $BeBr_2$, $BeI_2$, $BeC_2O_4$. $BeSO_4$, $Mg(OH)_2$, $MgCO_3$, $MgPO_4$, $MgO$, $MgCl_2$, $MgBr_2$, $MgI_2$, $MgC_2O_4$. $MgSO_4$, $Ca(OH)_2$, $CaO$, $CaCO_3$, $CaPO_4$, $CaCl_2$, $CaBr_2$, $Ca I_e$, $Ca(OH)_2$, $CaC_2O_4$, $CaSO_4$, $Y_2O_3$, $Y_2(CO_3)_3$, $Y_2(PO_4)_3$, $Y(OH)_3$, $YCl_3$, $YBr_3$, $YI_3$, $Y_2(C_2O4)_3$, $Y_2(SO4)_3$, $Zr(OH)_4$, $Zr(CO_3)_2$, $Zr(PO_4)_2$, $ZrO(OH)_2$, $ZrO2$, $ZrCl_4$, $ZrBr_4$, $ZrI_4$, $Zr(C_2O_4)_2$, $Zr(SO_4)_2$, $Ti(OH)_4$, $TiO(OH)_2$, $Ti(CO_3)_2$, $Ti(PO_4)_2$, $TiO_2$, $TiCl_4$, $TiBr_4$, $TiI_4$, $Ti(C_2O_4)_2$, $Ti(SO_4)_2$, $BaO$, $Ba(OH)_2$, $BaCO_3$, $BaPO_4$, $BaCl_2$, $BaBr_2$, $BaI_2$, $BaC_2O_4$, $BaSO_4$, $La(OH)_3$, $La_2(CO_3)_3$, $La_2(PO_4)_3$, $La_2O_3$, $LaCl_3$, $LaBr_3$, $LaI_3$, $La_2(C_2O_4)_3$, $La_2(SO_4)_3$, $Ce(OH)_4$, $Ce(CO_3)_2$, $Ce(PO_4)_2$, $CeO_2$, $Ce_2O_3$, $CeCl_4$, $CeBr_4$, $CeI_4$, $Ce(C_2O_4)_2$, $Ce(SO_4)_2$, $ThO_2$, $Th(CO_3)_2$, $Th(PO_4)_2$, $ThCl_4$, $ThBr_4$, $ThI_4$, $Th(OH)_4$, $Th(C_2O_4)_2$, $Th(SO_4)_2$, $Sr(OH)_2$, $SrCO_3$, $SrPO_4$, $SrO$, $SrCl_2$, $SrBr_2$, $SrI_2$, $SrC_2O_4$, $SrSO_4$, $Sm_2O_3$, $Sm_2(CO_3)_3$, $Sm_2(PO_4)_3$, $SmCl_3$, $SmBr_3$, $SmI_3$, $Sm(OH)_3$, $Sm_2(CO3)_3$, $Sm_2(C_2O_3)_3$, $Sm_2(SO_4)_3$, $LiCa_2Bi_3O_4Cl_6$, $Na_2WO_4$, $K/SrCoO_3$, $K/Na/SrCoO_3$, $Li/SrCoO_3$, $SrCoO_3$, molybdenum oxides, molybdenum hydroxides, molybdenum carbonates, molybdenum phosphates, molybdenum chlorides, molybdenum bromides, molybdenum iodides, molybdenum oxalates, molybdenum sulfates, manganese oxides, manganese chlorides, manganese bromides, manganese iodides, manganese hydroxides, manganese oxalates, manganese sulfates, manganese tungstates, vanadium oxides, vanadium carbonates, vanadium phosphates, vanadium chlorides, vanadium bromides, vanadium iodides, vanadium hydroxides, vanadium oxalates, vanadium sulfates, tungsten oxides, tungsten carbonates, tungsten phosphates, tungsten chlorides, tungsten bromides, tungsten iodides, tungsten hydroxides, tungsten oxalates, tungsten sulfates, neodymium oxides, neodymium carbonates, neodymium phosphates, neodymium chlorides, neodymium bromides, neodymium iodides, neodymium hydroxides, neodymium oxalates, neodymium sulfates, europium oxides, europium carbonates, europium phosphates, europium chlorides, europium bromides, europium iodides, europium hydroxides, europium oxalates, europium sulfates rhenium oxides, rhenium carbonates, rhenium phosphates, rhenium chlorides, rhenium bromides, rhenium iodides, rhenium hydroxides, rhenium oxalates, rhenium sulfates, chromium oxides, chromium carbonates, chromium phosphates, chromium chlorides, chromium bromides, chromium iodides, chromium hydroxides, chromium oxalates, chromium sulfates, potassium molybdenum oxides and the like.

"Oxide" refers to a metal compound comprising oxygen. Examples of oxides include, but are not limited to, metal oxides ($M_xO_y$), metal oxyhalides ($M_xO_yX_z$), metal oxynitrates ($M_xO_y(NO_3)_z$), metal phosphates ($M_x(PO_4)_y$), metal oxycarbonates ($M_xO_y(CO_3)_z$), metal carbonates, metal oxyhydroxides ($M_xO_y(OH)_z$), metal hydroxides ($M_x(OH)_z$) and the like, wherein X is independently, at each occurrence, fluoro, chloro, bromo or iodo, and x, y and z are numbers from 1 to 100.

"Crystal domain" means a continuous region over which a substance is crystalline.

"Single-crystalline nanowires" means a nanowire having a single crystal domain.

"Turnover number" is a measure of the number of reactant molecules a catalyst can convert to product molecules per unit time.

"Active" or "catalytically active" refers to a catalyst which has substantial activity in the reaction of interest. For example, in some embodiments a catalyst which is OCM active (i.e., has activity in the OCM reaction) has a C2+ selectivity of 5% or more and/or an oxygen conversion of 5% or more when the catalyst is employed as a heterogeneous catalyst in the oxidative coupling of methane at a temperature of 750° C. or less.

"Inactive" or "catalytically inactive" refers to a catalyst which does not have substantial activity in the reaction of interest. For example, in some embodiments a catalyst which is OCM inactive has a C2+ selectivity of less than 5% and/or an oxygen conversion of less than 5% when the catalyst is employed as a heterogeneous catalyst in the oxidative coupling of methane at a temperature of 750° C. or less.

"Oxygen conversion" is the percent of oxygen in the feed gas which is consumed.

"Activation temperature" refers to the temperature at which a catalyst becomes catalytically active.

"Light off temperature" is the temperature at which a catalyst or catalytic material has sufficient catalytic activity to initiate the desired reaction. In certain embodiments, e.g., for exothermic reactions like OCM, the light off temperature is at a sufficient level to not only allow initiation of the catalyzed reaction, but to do so at a rate that is thermally self-sufficient, e.g., generating enough thermal energy to maintain the reaction temperature at or above the initiation temperature.

"OCM activity" refers to the ability of a catalyst to catalyze the OCM reaction.

A catalyst having "high OCM activity" refers to a catalyst having a C2+ selectivity of 50% or more and/or an oxygen conversion of 10% or more when the catalyst is employed as a heterogeneous catalyst in the oxidative coupling of methane at a specific temperature, for example 750° C. or less.

A catalyst having "moderate OCM activity" refers to a catalyst having a C2+ selectivity of about 20-50% and/or an oxygen conversion of about 5-10% when the catalyst is employed as a heterogeneous catalyst in the oxidative coupling of methane at a temperature of 750° C. or less.

A catalyst having "low OCM activity" refers to a catalyst having a C2+ selectivity of about 5-20% and/or an oxygen conversion of about 1-5% when the catalyst is employed as a heterogeneous catalyst in the oxidative coupling of methane at a temperature of 750° C. or less.

"Base material" refers to the major component of a catalyst. For example a rare earth oxide which is doped with a dopant comprises a rare earth oxide base material.

"Dopant" or "doping agent" is additive added to or incorporated within a catalyst to optimize catalytic performance (e.g. increase or decrease catalytic activity). As compared to the undoped catalyst, a doped catalyst may increase or decrease the selectivity, conversion, and/or yield of a reaction catalyzed by the catalyst. A dopant may be present in the base catalyst material in any amount, and may in some embodiments be present in 50% or less by weight relative to the base catalyst material or in other embodiments it is present in more than 50% by weight relative to the base catalyst material.

"Atomic percent" (at % or at/at) or "atomic ratio" when used in the context of nanowire dopants refers to the ratio of the total number of dopant atoms to the total number of metal atoms in the nanowire. For example, the atomic percent of dopant in a lithium doped $Mg_6MnO_8$ nanowire is determined by calculating the total number of lithium atoms and dividing by the sum of the total number of magnesium and manganese atoms and multiplying by 100 (i.e., atomic percent of dopant=[Li atoms/(Mg atoms+Mn atoms)]×100).

"Weight percent" (wt/wt)" when used in the context of nanowire dopants refers to the ratio of the total weight of dopant to the total combined weight of the dopant and the nanowire. For example, the weight percent of dopant in a lithium doped $Mg_6MnO_8$ nanowire is determined by calculating the total weight of lithium and dividing by the sum of the total combined weight of lithium and $Mg_6MnO_8$ and multiplying by 100 (i.e., weight percent of dopant=[Li weight/(Li weight+$Mg_6MnO_8$ weight)]×100).

"Group 1" elements include lithium (Li), sodium (Na), potassium (K), rubidium (Rb), cesium (Cs), and francium (Fr).

"Group 2" elements include beryllium (Be), magnesium (Mg), calcium (Ca), strontium (Sr), barium (Ba), and radium (Ra).

"Group 3" elements include scandium (Sc) and yttrium (Y).

"Group 4" elements include titanium (Ti), zirconium (Zr), hafnium (Hf), and rutherfordium (Rf).

"Group 5" elements include vanadium (V), niobium (Nb), tantalum (Ta), and dubnium (Db).

"Group 6" elements include chromium (Cr), molybdenum (Mo), tungsten (W), and seaborgium (Sg).

"Group 7" elements include manganese (Mn), technetium (Tc), rhenium (Re), and bohrium (Bh).

"Group 8" elements include iron (Fe), ruthenium (Ru), osmium (Os), and hassium (Hs).

"Group 9" elements include cobalt (Co), rhodium (Rh), iridium (Ir), and meitnerium (Mt).

"Group 10" elements include nickel (Ni), palladium (Pd), platinum (Pt) and darmistadium (Ds).

"Group 11" elements include copper (Cu), silver (Ag), gold (Au), and roentgenium (Rg).

"Group 12" elements include zinc (Zn), cadmium (Cd), mercury (Hg), and copernicium (Cn).

"Lanthanides" include lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), yitterbium (Yb), and lutetium (Lu).

"Actinides" include actinium (Ac), thorium (Th), protactinium (Pa), uranium (U), *neptunium* (Np), plutonium (Pu), americium (Am), curium (Cm), berklelium (Bk), californium (Cf), einsteinium (Es), fermium (Fm), mendelevium (Md), nobelium (No), and lawrencium (Lr).

"Rare earth elements" include group 3 elements, lanthanides and actinides.

"Metal element" or "metal" is any element, except hydrogen, selected from Groups 1 through 12, lanthanides, actinides, aluminum (Al), gallium (Ga), indium (In), tin (Sn), thallium (Tl), lead (Pb), and bismuth (Bi). Metal elements include metal elements in their elemental form as well as metal elements in an oxidized or reduced state, for example, when a metal element is combined with other elements in the form of compounds comprising metal elements. For example, metal elements can be in the form of hydrates, salts, oxides, as well as various polymorphs thereof, and the like.

"Semi-metal element" refers to an element selected from boron (B), silicon (Si), germanium (Ge), arsenic (As), antimony (Sb), tellurium (Te), and polonium (Po).

"Non-metal element" refers to an element selected from carbon (C), nitrogen (N), oxygen (O), fluorine (F), phosphorus (P), sulfur (S), chlorine (Cl), selenium (Se), bromine (Br), iodine (I), and astatine (At).

"C2" refers to a hydrocarbon (i.e., compound consisting of carbon and hydrogen atoms) having only two carbon atoms, for example ethane and ethylene. Similarly, "C3" refers to a hydrocarbon having only 3 carbon atoms, for example propane and propylene.

"Conversion" means the mole fraction (i.e., percent) of a reactant converted to a product or products.

"Selectivity" refers to the percent of converted reactant that went to a specified product, e.g., C2 selectivity is the % of converted methane that formed ethane and ethylene, C3 selectivity is the % of converted methane that formed propane and propylene, C2+ selectivity is the % of converted methane that formed ethane and ethylene, propane and propylene, and other higher hydrocarbons, CO selectivity is the % of converted methane that formed CO.

"Yield" is a measure of (e.g. percent) of product obtained relative to the theoretical maximum product obtainable. Yield is calculated by dividing the amount of the obtained product in moles by the theoretical yield in moles. Percent yield is calculated by multiplying this value by 100. C2 yield is defined as the sum of the ethane and ethylene molar flow at the reactor outlet multiplied by two and divided by the inlet methane molar flow. C3 yield is defined as the sum of propane and propylene molar flow at the reactor outlet multiplied by three and divided by the inlet methane molar flow. C2+ yield is the sum of the C2 yield and C3 yield. Yield is also calculable by multiplying the methane conversion by the relevant selectivity, e.g., C2 yield is equal to the methane conversion times the C2 selectivity. C2+ yield is equal to the methane conversion times the C2+ selectivity.

"Alkane" means a straight chain or branched, noncyclic or cyclic, saturated aliphatic hydrocarbon. Alkanes include linear, branched and cyclic structures. Representative straight chain alkanes include methane, ethane, n-propane, n-butane, n-pentane, n-hexane, and the like; while branched alkanes include secbutane, isobutane, tertbutane, isopentane, and the like. Representative cyclic alkanes include cyclopropane, cyclobutane, cyclopentane, cyclohexane, and the like.

"Alkene" means a straight chain or branched, noncyclic or cyclic, unsaturated aliphatic hydrocarbon having at least one carbon-carbon double bond. Alkenes include linear, branched and cyclic structures. Representative straight chain and branched alkenes include ethylene, propylene, 1-butene, 2-butene, isobutylene, 1-pentene, 2-pentene, 3-methyl-1-butene, 2-methyl-2-butene, 2,3-dimethyl-2-butene, and the like. Cyclic alkenes include cyclohexene and cyclopentene and the like.

"Alkyne" means a straight chain or branched, noncyclic or cyclic, unsaturated aliphatic hydrocarbon having at least one carbon-carbon triple bond. Alkynes include linear, branched and cyclic structures. Representative straight chain and branched alkynes include acetylene, propyne, 1-butyne, 2-butyne, 1-pentyne, 2-pentyne, 3-methyl-1-butyne, and the like. Representative cyclic alkynes include cycloheptyne and the like.

"Alkyl," "alkenyl" and "alkynyl" refers to an alkane, alkene or alkyne radical, respectively.

"Aromatic" means a carbocyclic moiety having a cyclic system of conjugated p orbitals forming a delocalized conjugated $\pi$ system and a number of $\pi$ electrons equal to $4n+2$ with $n=0, 1, 2, 3$, etc. Representative examples of aromatics include benzene and naphthalene and toluene. "Aryl" refers to an aromatic radical. Exemplary aryl groups include, but are not limited to, phenyl, napthyl and the like.

"Carbon-containing compounds" are compounds that comprise carbon. Non-limiting examples of carbon-containing compounds include hydrocarbons, CO and $CO_2$.

As used throughout the specification, a catalyst composition represented by $E^1/E^2/E^3$, etc., wherein $E^1$, $E^2$ and $E^3$ are each independently an element or a compound comprising one or more elements, refers to a catalyst composition comprised of a mixture of $E^1$, $E^2$ and $E^3$. $E^1/E^2/E^3$, etc. are not necessarily present in equal amounts and need not form a bond with one another. For example, a catalyst comprising Li/MgO refers to a catalyst comprising Li and MgO, for example, Li/MgO may refer to a MgO catalyst doped with Li. In some examples, the catalysts are represented by M1/M2, where M1 and M2 are independently metal elements. In such examples it is understood that the catalysts also comprise oxygen (e.g., an oxide of M1 and/or M2), although not specifically depicted. Such catalysts may also further comprise one or more additional metal elements (M3, M4, M5, etc.). By way of another example, a catalyst comprising $NaMnO_4$/MgO refers to a catalyst comprised of a mixture of $NaMnO_4$ and MgO. Dopants may be added in suitable form. For example in a lithium doped magnesium oxide catalyst (Li/MgO), the Li dopant can be incorporated in the form of $Li_2O$, $Li_2CO_3$, LiOH, or other suitable forms. Li may be fully incorporated in the MgO crystal lattice (e.g., (Li,Mg)O) as well. Dopants for other catalyst may be incorporated analogously.

"Mixed oxide" or "mixed metal oxide" refers to a catalyst comprising at least two different oxidized metals. In various embodiments, the mixed oxides are "physical blends" of different oxidized metals. For example, in some embodiments, the mixed oxides are physical blends and are represented by $M1_xO_{z1}/M2_yO_{z2}$, wherein M1 and M2 are the same or different metal elements, O is oxygen and x, y, z1 and z2 are numbers from 1 to 100 and the "/" indicates that the two oxidized metals are in contact (e.g., physically blended) but not necessarily bound via a covalent or ionic or other type of bond. In other examples, a mixed oxide is a compound comprising two or more oxidized metals and oxygen (e.g., $M1_xM2_yO_z$, wherein M1 and M2 are the same or different metal elements, O is oxygen and x, y and z are numbers from 1 to 100).

A mixed oxide may comprise metal elements in various oxidation states and may comprise more than one type of metal element. For example, a mixed oxide of manganese and magnesium comprises oxidized forms of magnesium and manganese. Each individual manganese and magnesium atom may or may not have the same oxidation state. Mixed oxides comprising 3, 4, 5, 6 or more metal elements can be represented in an analogous manner. Mixed oxides include, but are not limited to metal oxides ($M_xO_y$), metal oxyhalides ($M_xO_yX_z$), metal oxynitrates ($M_xO_y(NO_3)_z$), metal phosphates ($M_x(PO_4)_y$), metal oxycarbonates ($M_xO_y(CO_3)_z$), metal carbonates, metal oxyhydroxides ($M_xO_y(OH)_z$) and the like, and combinations thereof, wherein X is independently, at each occurrence, fluoro, chloro, bromo or iodo, and x, y and z are numbers from 1 to 100. Mixed oxides may be represented herein as M1-M2, wherein M1 and M2 are each independently a metal element and M1 and M2 are oxidized. Mixed oxides comprising, 3, 4, 5, 6 or more metal elements can be represented in an analogous manner.

"Crush strength" is the force required to fracture or crush a material, such as a formed (e.g., extruded catalyst material). Crush strength can be expressed in force per length (N/mm) or force per area (N/mm$^2$) of the material. For example, crush strength can be determined by dividing the force required to crush the material by the largest projected area of the material. For example the largest projected area of a cylinder (diameter=1 mm and length=1 mm) would be diameter multiplied by the length or 1 mm$^2$. When expressed based on material length, crush strength is determined by the force required to crush the material divided by the material length (in the direction of the applied force). This definition is applicable to formed catalysts of different size and shape.

"Void fraction" or "void volume" is the volume of free space, i.e., space not occupied by the catalyst itself, divided by the total volume occupied by the catalytic form. For example, the void fraction of a ring-shaped catalyst is the volume associated with the central void (hole) divided by the total volume occupied by the ring. The void fraction or void volume of a catalyst bed (e.g., a plurality of extrudates or tableted catalytic materials) is the volume of free space associated with each individual catalyst form plus the free space associated with inter-catalyst voids divided by the total volume occupied by the catalyst bed. The calculation of free space, as described above, does not include any free space associated with the porosity of the catalytic material.

"Porosity" is the volume of void within catalyst the catalyst itself divided by the catalyst volume. For purposes of this calculation, the catalyst volume does not include any void fraction or void volume.

A catalyst that "has activity for" a certain reaction (e.g., oxidative coupling of methane) refers to a catalyst that lowers the transition state, increases the reaction rate, increases conversion of reactants, increases selectivity for a certain product, or combinations thereof, under the conditions of the reaction relative to the reaction performed in the absence of the catalyst.

1. Catalysts

The catalyst forms and formulations described herein generally comprise one or more catalysts (also referred to herein as the "active catalyst" or the "base material"), which are optionally combined with a support, binder and/or diluent material. In some embodiments, diluents are selected from bulk materials (e.g. commercial grade), nano materials (nanowires, nanorods, nanoparticles, etc.) and combinations thereof. Catalysts useful in the various embodiments of the invention include any heterogeneous catalyst, for example catalysts comprising transition metal oxides or lanthanide oxides. The catalysts can have various elemental components and activity in a variety of reactions. In certain embodiments the catalyst is an OCM active catalyst (i.e., increases the rate of the OCM reaction relative to the uncatalyzed OCM reaction). In other embodiments the catalyst is an ODH active catalyst (i.e., increases the rate of the ODH reaction relative to the uncatalyzed ODH reaction). The exact elemental components and/or morphological form of the catalysts are not limited and various embodiments include different elemental compositions and/or morphologies. In this regard, catalysts useful for practice of various embodiments of the invention include any bulk and/or nanostructured catalyst (e.g., nanowire) in any combination. For example, in some embodiments the catalyst comprises a catalyst as described in co-pending U.S. application Ser. No. 13/115,082 (U.S. Pub. No. 2012/0041246); Ser. No. 13/479, 767 (U.S. Pub. No. 2013/0023709); Ser. No. 13/689,611 (U.S. Pub. No. 2013/0165728); Ser. No. 13/689,514 (U.S. Pub. No. 2013/0158322) and U.S. Provisional Application Nos. 61/794,486; 61/909,840; and 61/988,063, the full disclosures of which are hereby incorporated by reference in their entirety for their disclosure of catalysts, and methods for use of the same, disclosed therein. In certain embodiments, the catalyst is a nanostructured catalyst, such as a nanowire catalyst, for example a nanowire comprising a metal oxide, metal hydroxide, metal oxyhydroxide, metal oxycarbonate, metal carbonate or combinations thereof. In some other related embodiments, the catalyst is an inorganic nanowire comprising one or more metal elements from any of Groups 1 through 7, lanthanides, actinides or combinations thereof and a dopant comprising a metal element, a semi-metal element, a non-metal element or combinations thereof.

In some other embodiments, the catalyst is an inorganic catalytic polycrystalline nanowire, the nanowire having a ratio of effective length to actual length of less than one and an aspect ratio of greater than ten as measured by TEM in bright field mode at 5 keV, wherein the nanowire comprises one or more elements from any of Groups 1 through 7, lanthanides, actinides or combinations thereof. Such a nanowire may optionally include one or more dopants.

In some other embodiments, the catalyst is an inorganic nanostructured catalyst. For example an inorganic catalytic nanowire, the nanowire having a ratio of effective length to actual length of one and an aspect ratio of greater than ten as measured by TEM in bright field mode at 5 keV, wherein the nanowire may optionally include one or more dopants.

In other embodiments, the present invention is directed to catalyst forms and formulations comprising a nanostructured catalyst, such as a catalytic nanowire, which comprises at least four different doping elements, wherein the doping elements are selected from a metal element, a semi-metal element and a non-metal element. In other embodiments, the catalyst is a catalytic nanowire comprising at least two different doping elements, wherein the doping elements are selected from a metal element, a semi-metal element and a non-metal element, and wherein at least one of the doping elements is K, Sc, Ti, V, Nb, Ru, Os, Ir, Cd, In, Tl, S, Se, Po, Pr, Tb, Dy, Ho, Er, Tm, Lu or an element selected from any of groups 6, 7, 10, 11, 14, 15 or 17.

Other embodiments include catalytic forms and formulations wherein the catalyst comprises at least one of the following dopant combinations: Eu/Na, Sr/Na, Na/Zr/Eu/Ca, Mg/Na, Sr/Sm/Ho/Tm, Sr/W, Mg/La/K, Na/K/Mg/Tm, Na/Dy/K, Na/La/Dy, Sr/Hf/K, Na/La/Eu, Na/La/Eu/In, Na/La/K, Na/La/Li/Cs, K/La, K/La/S, K/Na, Li/Cs, Li/Cs/La, Li/Cs/La/Tm, Li/Cs/Sr/Tm, Li/Sr/Cs, Li/Sr/Zn/K, Li/Ga/Cs, Li/K/Sr/La, Li/Na, Li/Na/Rb/Ga, Li/Na/Sr, Li/Na/Sr/La, Sr/Zr, Li/Sm/Cs, Ba/Sm/Yb/S, Ba/Tm/K/La, Ba/Tm/Zn/K, Sr/Zr/K, Cs/K/La, Cs/La/Tm/Na, Cs/Li/K/La, Sm/Li/Sr/Cs, Sr/Cs/La, Sr/Tm/Li/Cs, Zn/K, Zr/Cs/K/La, Rb/Ca/In/Ni, Sr/Ho/Tm, La/Nd/S, Li/Rb/Ca, Li/K, Tm/Lu/Ta/P, Rb/Ca/Dy/P, Mg/La/Yb/Zn, Rb/Sr/Lu, Na/Sr/Lu/Nb, Na/Eu/Hf, Dy/Rb/Gd, Sr/Ce, Na/Pt/Bi, Rb/Hf, Ca/Cs, Ca/Mg/Na, Hf/Bi, Sr/Sn, Sr/W, Sr/Nb, Sr/Ce/K, Zr/W, Y/W, Na/W, Bi/W, Bi/Cs, Bi/Ca, Bi/Sn, Bi/Sb, Ge/Hf, Hf/Sm, Sb/Ag, Sb/Bi, Sb/Au, Sb/Sm, Sb/Sr, Sb/W, Sb/Hf, Sb/Yb, Sb/Sn, Yb/Au, Yb/Ta, Yb/W, Yb/Sr, Yb/Pb, Yb/W, Yb/Ag, Au/Sr, W/Ge, Sr/Tb, Ta/Hf, W/Au, Ca/W, Au/Re, Sm/Li, La/K, Zn/Cs, Na/K/Mg, Zr/Cs, Ca/Ce, Na/Li/Cs, Li/Sr, Cs/Zn, La/Dy/K, Dy/K, La/Mg, Na/Nd/In/K, In/Sr, Sr/Cs, Rb/Ga/Tm/Cs, Ga/Cs, K/La/Zr/Ag, Lu/Fe, Sr/Tb/K, Sr/Tm, La/Dy, Sm/Li/Sr, Mg/K, Sr/Pr, Li/Rb/Ga, Li/Cs/Tm, Zr/K, Li/Cs, Li/K/La, Ce/Zr/La, Ca/Al/La, Sr/Zn/La, Sr/Cs/Zn, Sm/Cs, In/K, Ho/Cs/Li/La, Sr/Pr/K, Cs/La/Na, La/S/Sr, K/La/Zr/Ag, Lu/Tl, Pr/Zn, Rb/Sr/La, Na/Sr/Eu/Ca, K/Cs/Sr/La, Na/Sr/Lu, Sr/Eu/Dy, Lu/Nb, La/Dy/Gd, Na/Mg/Tl/P, Na/Pt, Gd/Li/K, Rb/K/Lu, Sr/La/Dy/S, Na/Ce/Co, Na/Ce, Na/Ga/Gd/Al, Ba/Rh/Ta, Ba/Ta, Na/Al/Bi, Sr/Hf/Rb, Cs/Eu/S, Sm/Tm/Yb/Fe, Sm/Tm/Yb, Hf/Zr/Ta, Rb/Gd/Li/K, Gd/Ho/Al/P, Na/Ca/Lu, Cu/Sn, Ag/Au, Al/Bi, Al/Mo, Al/Nb, Au/Pt, Ga/Bi, Mg/W, Pb/Au, Sn/Mg, Sr/B, Zn/Bi, Gd/Ho, Zr/Bi, Ho/Sr, Gd/Ho/Sr, Ca/Sr, Ca/Sr/W, Sr/Ho/Tm/Na, Na/Zr/Eu/Tm, Sr/Ho/Tm/Na, Sr/Pb, Sr/W/Li, Ca/Sr/W or Sr/Hf. In various embodiments of the foregoing, the catalyst is a catalytic nanowire, for example a catalytic nanowire comprising a rare earth oxide and one or more of the foregoing dopant combinations.

In other embodiments, the catalyst comprises a lanthanide mixed oxide compound. For example, in certain embodiments the catalyst is a nanostructured catalyst, such as a catalytic nanowire, comprising $Ln1_{4-x}Ln2_xO_6$ and a dopant comprising a metal element, a semi-metal element, a non-metal element or combinations thereof, wherein Ln1 and Ln2 are each independently a lanthanide element, wherein Ln1 and Ln2 are not the same and x is a number ranging from greater than 0 to less than 4. In other embodiments, the catalyst is a catalytic nanowire comprising a mixed oxide of Y—La, Zr—La, Pr—La, Ce—La, Er—La, La—Nd, Y—Nd, Zr—Nd, Pr—Nd, Ce—Nd, Er—Nd, Y—Gd, Zr—Gd, Pr—Gd, Ce—Gd, Er—Gd, Y—Sm, Zr—Sm, Pr—Sm, Ce—Sm, Er—Sm, La—Sm, La—Gd, La—Eu, La—Ho, Nd—Gd, Nd—Sm, Nd—Eu, Nd—Ho, Sm—Gd, Sm—Ho, Sm—Eu, Gd—Ho, Gd—Eu, Eu—Ho, Y—Eu, Zr—Eu, Pr—Eu, Ce—Eu, Er—Eu, Y—Ho, Zr—Ho, Pr—Ho, Ce—Ho or Er—Ho, or combinations thereof and at least one dopant selected from a metal element, a semi-metal element and a non-metal element.

In still other embodiments, the catalyst is a mixed oxide comprising three or more metal elements. In some embodiments, the metal elements are selected from Y, Zr, La, Ce, Pr, Nd, Gd, Sm, Eu, Ho and Er. In certain other embodiments the catalyst is a catalytic nanowire comprising a mixed oxide selected from Y—La—Zr, Y—La—Ce, Y—La—Pr, Y—La—Nd, Y—La—Er, Zr—La—Ce, Zr—La—Pr, Zr—La—Nd, Zr—La—Er, Pr—La—Ce, Pr—La—Nd, Pr—La—Er, Ce—La—Pr, Ce—La—Nd, Ce—La—Er, Er—La—Nd, Y—Nd—Zr, Y—Nd—Ce, Y—Nd—Pr, Y—Nd—Er, Zr—Nd—Ce, Zr—Nd—Pr, Zr—Nd—Er, Pr—Nd—Ce, Pr—Nd—Er, Gd—Y—Zr, Gd—Y—La, Gd—Y—Ce, Gd—Y—Pr, Gd—Zr—La, Gd—Zr—Ce, Gd—Zr—Pr, Gd—Zr—Nd, Gd—Zr—Sm, Gd—Zr—Eu, Gd—Zr—Ho, Gd—Zr—Er, Gd—La—Ce, Gd—La—Pr, Gd—La—Nd, Gd—La—Sm, Gd—La—Eu, Gd—La—Ho, Gd—La—Er, Gd—Ce—Pr, Gd—Ce—Nd, Gd—Ce—Sm, Gd—Ce—Eu, Gd—Ce—Ho, Gd—Ce—Er, Gd—Pr—Nd, Gd—Pr—Sm, Gd—Pr—Eu, Gd—Pr—Ho, Gd—Pr—Er, Gd—Nd—Sm, Gd—Nd—Eu, Gd—Nd—Ho, Gd—Nd—Er, Gd—Sm—Eu, Gd—Sm—Ho, Gd—Sm—Er, Gd—Eu—Ho, Gd—Eu—Er, Gd—Ho—Er, Sm—Y—Zr, Sm—Y—La, Sm—Y—Ce, Sm—Y—Pr, Sm—Zr—La, Sm—Zr—Ce, Sm—Zr—Pr, Sm—Zr—Nd, Sm—Zr—Eu, Sm—Zr—Ho, Sm—Zr—Er, Sm—La—Ce, Sm—La—Pr, Sm—La—Nd, Sm—La—Eu, Sm—La—Ho, Sm—La—Er, Sm—Ce—Pr, Sm—Ce—Nd, Sm—Ce—Eu, Sm—Ce—Ho, Sm—Ce—Er, Sm—Pr—Nd, Sm—Pr—Eu, Sm—Pr—Ho, Sm—Pr—Er, Sm—Nd—Eu, Sm—Nd—Ho, Sm—Nd—Er, Sm—Eu—Ho, Sm—Eu—Er, Sm—Ho—Er, Eu—Y—Zr, Eu—Y—La, Eu—Y—Ce, Eu—Y—Pr, Eu—Zr—La, Eu—Zr—Ce, Eu—Zr—Pr, Eu—Zr—Nd, Eu—Zr—Ho, Eu—Zr—Er, Eu—La—Ce, Eu—La—Pr, Eu—La—Nd, Eu—La—Ho, Eu—La—Er, Eu—Ce—Pr, Eu—Ce—Nd, Eu—Ce—Ho, Eu—Ce—Er, Eu—Pr—Nd, Eu—Pr—Ho, Eu—Pr—Er, Eu—Nd—Eu, Eu—Nd—Ho, Eu—Nd—Er, Eu—Ho—Er, Ho—Y—Zr, Ho—Y—La, Ho—Y—Ce, Ho—Y—Pr, Ho—Zr—La, Ho—Zr—Ce, Ho—Zr—Pr, Ho—Zr—Nd, Ho—Zr—Er, Ho—La—Ce, Ho—La—Pr, Ho—La—Nd, Ho—La—Er, Ho—Ce—Pr, Ho—Ce—Nd, Ho—Ce—Er, Ho—Pr—Nd, Ho—Pr—Er, Ho—Nd—Er, Ce—Nd—Er and combinations thereof. In further embodiments, the foregoing mixed oxides are doped with at least one dopant selected from a metal element, a semi-metal element and a non-metal element. In various embodiments of the above, the catalyst is a catalytic nanowire.

In some other embodiments, the catalyst comprises a mixed oxide of a rare earth element and a Group 13 element, wherein the catalyst further comprises one or more Group 2 elements. In some more specific embodiments, the foregoing catalyst is a nanostructured catalyst, such as a nanowire catalyst.

In another embodiment the catalyst comprises a lanthanide oxide doped with an alkali metal, an alkaline earth metal or combinations thereof, and at least one other dopant from groups 4-16 or a rare earth element. In some more specific embodiments, the foregoing catalyst is a nanostructured catalyst, such as a nanowire catalyst.

Other lanthanide-containing catalysts have also been found useful in various embodiments of the invention. For example, in some embodiments, the catalysts comprise a mixed oxide base material, the mixed oxide comprising erbium (Er) and at least one further lanthanide element. In other embodiments, the catalysts comprise a mixed oxide base material, the mixed oxide comprising lanthanum (La) and at least one further lanthanide element. In other embodiments, the catalysts comprise a mixed oxide base material, the mixed oxide comprising cerium (Ce) and at least one further lanthanide element. In other embodiments, the catalysts comprise a mixed oxide base material, the mixed oxide comprising praseodymium (Pr) and at least one further lanthanide element. In other embodiments, the catalysts comprise a mixed oxide base material, the mixed oxide comprising neodymium (Nd) and at least one further lanthanide element. In other embodiments, the catalysts comprise a mixed oxide base material, the mixed oxide comprising promethium (Pm) and at least one further lanthanide element. In other embodiments, the catalysts comprise a mixed oxide base material, the mixed oxide comprising samarium (Sm) and at least one further lanthanide element. In other embodiments, the catalysts comprise a mixed oxide base material, the mixed oxide comprising europium (Eu) and at least one further lanthanide element. In other embodiments, the catalysts comprise a mixed oxide base material, the mixed oxide comprising gadolinium (Gd) and at least one further lanthanide element. In other embodiments, the catalysts comprise a mixed oxide base material, the mixed oxide comprising terbium (Tb) and at least one further lanthanide element. In other embodiments, the catalysts comprise a mixed oxide base material, the mixed oxide comprising dysprosium (Dy) and at least one further lanthanide element. In other embodiments, the catalysts comprise a mixed oxide base material, the mixed oxide comprising holmium (Ho) and at least one further lanthanide element. In other embodiments, the catalysts comprise a mixed oxide base material, the mixed oxide comprising thulium (Tm) and at least one further lanthanide element. In other embodiments, the catalysts comprise a mixed oxide base material, the mixed oxide comprising ytterbium (Yb) and at least one further lanthanide element. In other embodiments, the catalysts comprise a mixed oxide base material, the mixed oxide comprising lutetium (Lu) and at least one further lanthanide element.

In other embodiments, the catalysts comprise a mixed oxide base material having the following formula:

$$Ln1_a Ln2_b O_c$$

wherein:
Ln1 and Ln2 are independently different lanthanide elements;
O is oxygen; and
a, b and c are each independently numbers greater than 0.

In still more embodiments, the catalyst comprises a mixed oxide base material having the following formula:

$$Ln1_a Ln2_b Ln3_d Ln4_e Ln5_f O_c$$

wherein:
Ln1, Ln2, Ln3, Ln4 and Ln5 are independently different lanthanide elements;
O is oxygen; and
a, b, c and d are each independently numbers greater than 0; and
e and f are independently 0 or a number greater than 0.

In other embodiments, the catalyst comprises a base material comprising an oxide of one or more lanthanide elements and a dopant combination selected from Sr/Sm, Sr/Gd, Sr/Dy, Sr/Er, Sr/Lu, Sr/W, Sr/Ba/B, Ba/B, Ba/Sr, Er/W, Sr/K, Ba/Ce, Ba/Hf, Ga/Mg, Mg/Er, Y/Ba, Sr/Ga/Mg, Sr/Y, Sr/B/Y, Ca/B, Sr/Al, Ba/W, B/W, Sr/Ba/W, Sr/W/B, Ba/W/B, Sr/Ce, Sr/Tb, Sr/B and Sr/Hf/K and Sr/Ba/W/B.

In still other embodiments, the catalyst comprises a single pass methane conversion in an OCM reaction of greater than 10%, for example in some such embodiments the catalyst is a catalytic nanowire. In other embodiments the catalyst comprises a C2+ selectivity of greater than 10% in the OCM reaction when the OCM reaction is performed with an oxygen source other than air or $O_2$ (e.g., $CO_2$). In certain embodiments of the foregoing, the catalyst is a catalytic nanowire. In various embodiments the foregoing C2+ selectivities are obtained when the OCM reaction is performed with a methane:oxygen ratio of less than about 12, a pressure of about 8 barg and temperatures above about 400 C.

In yet other embodiments, the catalyst comprises a mixed oxide of magnesium and manganese, wherein the catalyst further comprises lithium and boron dopants and at least one doping element from groups 4, 9, 12, 13 or combinations thereof. In other examples, the catalyst comprises an oxide of a rare earth element, wherein the catalyst further comprises at least one doping element from groups 1-16, lanthanides, actinides or combinations thereof. In still other examples, the catalyst comprises a mixed oxide of manganese and tungsten, wherein the catalyst further comprises a sodium dopant and at least one doping element from groups 2, 4-6, 8-15, lanthanides or combinations thereof. In yet other embodiments, the catalyst comprises a mixed oxide of a lanthanide and tungsten, wherein the catalyst further comprises a sodium dopant and at least one doping element from groups 2, 4-15, lanthanides or combinations thereof, wherein the catalyst comprises a C2+ selectivity of greater than 50% and a methane conversion of greater than 20% when the catalyst is employed as a heterogeneous catalyst in the oxidative coupling of methane at a temperature of 750° C. or less.

In other aspects, the catalytic forms and formulations comprise a catalyst comprising a mixed oxide of manganese and tungsten, wherein the catalyst further comprises a sodium dopant and at least one doping element from groups 2, 16 or combinations thereof.

In various embodiments, the catalysts employed in the catalytic materials herein have a C2+ selectivity of greater than 45%, greater than 50%, greater than 55%, greater than 60%, greater than 65%, greater than 70% or even greater than 75% when the catalyst is employed as a heterogeneous catalyst in the oxidative coupling of methane at a temperature of 750° C. or less, 700° C. or less, 650° C. or less or even 600° C. or less.

In other embodiments, the catalysts have a methane conversion in the OCM reaction of greater than 10%, greater than 12%, greater than 15%, greater than 20%, greater than 22%, greater than 25%, greater than 30% or even greater than 35% when the catalyst is employed as a heterogeneous catalyst in the oxidative coupling of methane at an inlet temperature of 750° C. or less, 700° C. or less, 650° C. or less or even 600° C. or less.

In various embodiments of the foregoing catalysts, the catalyst comprises a C2+ selectivity of greater than 45% and a methane conversion of greater than 10%, greater than 12%, greater than 15%, greater than 20%, greater than 22%, greater than 25%, greater than 30% or even greater than 35% when the catalyst is employed as a heterogeneous catalyst in the oxidative coupling of methane at a temperature of 750° C. or less, 700° C. or less, 650° C. or less or even 600° C. or less. In further embodiments of the foregoing, the oxygen conversion in the OCM reaction is greater than 90%, for examples about 100%.

In various embodiments of the foregoing catalysts, the catalyst comprises a C2+ selectivity of greater than 50% and a methane conversion of greater than 10%, greater than 12%, greater than 15%, greater than 20%, greater than 22%, greater than 25%, greater than 30% or even greater than 35% when the catalyst is employed as a heterogeneous catalyst in the oxidative coupling of methane at a temperature of 750° C. or less, 700° C. or less, 650° C. or less or even 600° C. or less. In further embodiments of the foregoing, the oxygen conversion in the OCM reaction is greater than 90%, for examples about 100%.

In various embodiments of the foregoing catalysts, the catalyst comprises a C2+ selectivity of greater than 55% and a methane conversion of greater than 10%, greater than 12%, greater than 15%, greater than 20%, greater than 22%, greater than 25%, greater than 30% or even greater than 35% when the catalyst is employed as a heterogeneous catalyst in the oxidative coupling of methane at a temperature of 750° C. or less, 700° C. or less, 650° C. or less or even 600° C. or less. In further embodiments of the foregoing, the oxygen conversion in the OCM reaction is greater than 90%, for examples about 100%.

In various embodiments of the foregoing catalysts, the catalyst comprises a C2+ selectivity of greater than 60% and a methane conversion of greater than 10%, greater than 12%, greater than 15%, greater than 20%, greater than 22%, greater than 25%, greater than 30% or even greater than 35% when the catalyst is employed as a heterogeneous catalyst in the oxidative coupling of methane at a temperature of 750° C. or less, 700° C. or less, 650° C. or less or even 600° C. or less. In further embodiments of the foregoing, the oxygen conversion in the OCM reaction is greater than 90%, for examples about 100%.

In various embodiments of the foregoing catalysts, the catalyst comprises a C2+ selectivity of greater than 65% and a methane conversion of greater than 10%, greater than 12%, greater than 15%, greater than 20%, greater than 22%, greater than 25%, greater than 30% or even greater than 35% when the catalyst is employed as a heterogeneous catalyst in the oxidative coupling of methane at a temperature of 750° C. or less, 700° C. or less, 650° C. or less or even 600° C. or less. In further embodiments of the foregoing, the oxygen conversion in the OCM reaction is greater than 90%, for examples about 100%.

In various embodiments of the foregoing catalysts, the catalyst comprises a C2+ selectivity of greater than 70% and a methane conversion of greater than 10%, greater than 12%, greater than 15%, greater than 20%, greater than 22%, greater than 25%, greater than 30% or even greater than 35% when the catalyst is employed as a heterogeneous catalyst in the oxidative coupling of methane at a temperature of 750° C. or less, 700° C. or less, 650° C. or less or even 600° C. or less. In further embodiments of the foregoing, the oxygen conversion in the OCM reaction is greater than 90%, for example about 100%.

In various embodiments of the foregoing catalysts, the catalyst comprises a C2+ selectivity of greater than 75% and a methane conversion of greater than 10%, greater than 12%, greater than 15%, greater than 20%, greater than 22%, greater than 25%, greater than 30% or even greater than 35% when the catalyst is employed as a heterogeneous catalyst in the oxidative coupling of methane at a temperature of 750° C. or less, 700° C. or less, 650° C. or less or even 600° C. or less. In further embodiments of the foregoing, the oxygen conversion in the OCM reaction is greater than 90%, for examples about 100%.

In some embodiments, the catalysts comprise cerium and one or more non-cerium lanthanide compounds. For example, in some embodiments the catalysts comprise cerium and an oxide or hydroxide (or oxyhydroxide) of one or more non-cerium lanthanides. For example, in some embodiments the catalysts comprise cerium and a compound having the following formula:

$$Ln1_xLn2_yO_z(OH)_n$$

wherein:

Ln1 and Ln2 are each independently different non-cerium lanthanide elements;

O is oxygen;

OH is hydroxy; and n, x, y and z are each independently numbers of 0 or greater, provided that at least one of x or y is greater than 0 and at least one of n or z is greater than 0.

While any of the non-cerium lanthanides are included, in some embodiments Ln1 is La or Nd.

The percentage of cerium in the catalyst can be varied, and in some embodiment ranges from greater than 0% w/w and up to 20% w/w/cerium. In some embodiments, cerium is present in about 0.1% to about 10% w/w.

Other catalysts useful in the context of the catalytic forms and formulations described herein will be readily apparent to one of ordinary skill in the art.

2. Catalytic Formulations

As noted above, the present disclosure provides a catalytic material comprising a plurality of catalysts and optionally one or more binder, support, diluent and/or carrier materials. In some embodiments, the catalytic material comprises a plurality of bulk catalysts. In some embodiments, the catalytic material comprises a plurality of nanostructured catalysts, such as catalytic nanowires. In other embodiments, the catalytic materials comprise a plurality of inorganic catalytic polycrystalline nanowires, the plurality of nanowires having a ratio of average effective length to average actual length of less than one and an average aspect ratio of greater than ten as measured by TEM in bright field mode at 5 keV, wherein the plurality of nanowires comprises one or more elements from any of Groups 1 through 7, lanthanides, actinides or combinations thereof. In still other embodiments, the catalytic materials comprise a bulk catalyst. Mixtures of bulk and nanostructured catalysts (e.g., nanowires) are also contemplated.

Typically, heterogeneous catalysts are used either in their pure form or blended with inert materials, such as silica, alumina, etc. The blending with inert materials may be used in order to reduce and/or control large temperature non-uniformities within the reactor bed often observed in the case of strongly exothermic (or endothermic) reactions. In the case of complex multistep reactions, such as the reaction to convert methane into ethane and/or ethylene (OCM), typical blending materials can selectively slow down or quench one or more of the reactions of the system and promote unwanted side reactions. For example, in the case of the oxidative coupling of methane, silica and alumina can quench the methyl radicals and thus prevent the formation of ethane. Accordingly, certain embodiments are directed to catalytic materials comprising a catalyst (e.g., catalytic nanowire) and a blending material which enhances, rather than reduces, the catalytic activity of the catalyst.

In certain aspects, the present disclosure provides a catalytic material which solves problems typically associated with typical catalyst support material. Accordingly, in certain embodiments the catalytic activity of the catalytic material can be tuned by blending two or more catalysts and/or catalyst support materials. The blended catalytic material may comprise catalytic nanowires, bulk catalysts, or both and/or inert support material.

In other aspects, the present invention is directed to a catalytic material having a single pass methane conversion of greater than 10%, greater than 15%, greater than 20% or even greater than 25% when the catalytic material is employed as a catalytic material in the oxidative coupling of methane at inlet reactor temperatures of 750° C. or less, for example temperatures of less than 700° C., of less than 650° C., of less than 600° C. or even temperatures of less than 550° C.

In certain embodiments, the catalytic material comprises a support, diluent and/or carrier. In some embodiments, the diluent is porous and has a high surface area. In some embodiments the support is active (i.e. has catalytic activity). In other embodiments, the diluent is inactive (i.e. non-catalytic). In some embodiments, the diluent comprises an inorganic material such as an inorganic oxide. In other embodiments the diluents comprises $Al_2O_3$, $SiO_2$, $TiO_2$, MgO, CaO, SrO, BaO, $ZrO_2$, ZnO, $LiAlO_2$, $MgAl_2O_4$, MnO, $MnO_2$, $Mn_3O_4$, $La_2O_3$, $Ln_2O_3$, where Ln is a lanthanide element, $AlPO_4$, $SiO_2/Al_2O_3$, $B_2O_3$, $Ga_2O_3$, $In_2O_3$, $SrAl_2O_4$, $B_4SrO_7$, $CaCO_3$, $SrCO_3$, $BaCO_3$, activated carbon, silica gel, zeolites, activated clays, activated $Al_2O_3$, SiC, diatomaceous earth, aluminosilicates, calcium aluminate, barium aluminate, $CeO_2$, sulfates (e.g., $SrSO_4$, $BaSO_4$, etc.), support nanowires or combinations thereof. In still other embodiments, the diluent comprises a carbide (e.g., boron-carbide, silicon carbide and the like), a nitride, a carbonate (e.g., alkaline earth metal carbonate), a silicate or an aluminate.

In various embodiments of the above, the catalyst is a catalytic nanowire and the diluent comprises SrO, BaO, $B_2O_3$, $Ga_2O_3$, $In_2O_3$, $SrAl_2O_4$, $B_4SrO_7$, $CaCO_3$, $SrCO_3$, $BaCO_3$, SiC, barium aluminate, $CeO_2$, sulfates (e.g., $SrSO_4$, $BaSO_4$, etc.), or combinations thereof.

In some more specific embodiments the diluent comprises silicon, for example $SiO_2$. In other embodiments the diluent comprises magnesium, for example MgO. In other embodiments the diluent comprises zirconium, for example $ZrO_2$. In yet other embodiments, the diluent comprises lanthanum, for example $La_2O_3$. In yet other embodiments, the diluent comprises yttrium, for example $Y_2O_3$. In yet other embodiments, the diluent comprises hafnium, for example $HfO_2$. In yet other embodiments, the diluent comprises aluminum, for example $Al_2O_3$. In yet other embodiments, the diluent comprises gallium, for example $Ga_2O_3$.

In still other embodiments, the diluent material comprises an inorganic oxide, $Al_2O_3$, $SiO_2$, $TiO_2$, MgO, $ZrO_2$, $HfO_2$, CaO, SrO, ZnO, $LiAlO_2$, $MgAl_2O_4$, MnO, $MnO_2$, $Mn_2O_4$, $Mn_3O_4$, $La_2O_3$, $Ln_2O_3$, where Ln is a lanthanide element, activated carbon, silica gel, zeolites, activated clays, activated $Al_2O_3$, diatomaceous earth, aluminosilicates, calcium aluminate, barium aluminate, $CeO_2$, sulfates (e.g., $SrSO_4$, $BaSO_4$, etc.), or combinations thereof. For example, the diluent material may comprise $SiO_2$, $ZrO_2$, CaO, $La_2O_3$ or MgO.

In still other embodiments, the diluent material comprises an SrO, ZnO, $LiAlO_2$, barium aluminate, $CeO_2$, sulfates (e.g., $SrSO_4$, $BaSO_4$, etc.) or combinations thereof.

In still other embodiments, the diluent material comprises a carbonate. For example, in some embodiments the diluent material comprises $MgCO_3$, $CaCO_3$, $SrCO_3$, $BaCO_3$, $Y_2(CO_3)_3$, $La_2(CO_3)_3$ or combination thereof.

In other embodiments, the catalytic materials described herein comprise a catalyst and a diluent, the diluent comprising a metal carbonate, a metal sulfate, a metal phosphate, a metal halide or combinations thereof. In some of these embodiments the catalyst is a nanowire catalyst. For example, in some embodiments, the diluent comprises a metal carbonate. In other embodiments, the diluent comprises an alkaline earth metal carbonate. In even more embodiments, the catalyst comprises a rare earth oxide.

Other examples of diluents useful in various embodiments include, but are not limited to, $MgCO_3$, $MgSO_4$, $Mg_3(PO_4)_2$, $CaCO_3$, $CaSO_4$, $Ca_3(PO_4)_2$, SrO, $SrCO_3$, $SrSO_4$, $Sr_3(PO_4)_2$, $SrAl_2O_4$, BaO, $BaCO_3$, $BaSO_4$, $Ba_3(PO_4)_2$, $BaAl_2O_4$ and the like. Most of these compounds are very cheap, especially $MgCO_3$, $CaCO_3$, SrO, $SrCO_3$ and thus very attractive for use as diluents from an economic point of view. Additionally, the magnesium and calcium compounds are also environmentally friendly. Accordingly, an embodiment of the invention provides a catalytic material comprising a catalytic nanowire in combination with a diluent selected from one or more of $MgCO_3$, $MgSO_4$, $Mg_3(PO_4)_2$, $CaCO_3$, $CaSO_4$, $Ca_3(PO_4)_2$, SrO, $SrCO_3$, $SrSO_4$, $Sr_3(PO_4)_2$, BaO, $BaCO_3$, $BaSO_4$, $Ba_3(PO_4)_2$. In some specific embodiments the diluent is SrO, $MgCO_3$, $CaCO_3$, $SrCO_3$ or a combination thereof. In other embodiments, the catalytic material comprises a catalytic nanowire in combination with a diluent selected from one or more of MgO, CaO, $MgAl_2O_4$ and $CaAl_2O_4$, $MgCO_3$, $MgSO_4$, $Mg_3(PO_4)_2$, $CaCO_3$, $CaSO_4$, $Ca_3(PO_4)_2$, SrO, $SrCO_3$, $SrSO_4$, $Sr_3(PO_4)_2$, BaO, $BaCO_3$, $BaSO_4$, $Ba_3(PO_4)_2$. In some embodiments the diluent is SrO, $MgCO_3$, $CaCO_3$, $SrCO_3$ or a combination thereof. In some embodiments, the diluent is selected from magnesium aluminates and calcium aluminates. In other embodiments, the diluent comprises a group 4 element. In some of these embodiments the group 4 element is present in the form of a compound comprising an alkaline earth metal and the group 4 element, for example an alkaline earth metal titanate, hafnate or zirconate, non-limiting examples of which include calcium titanate, calcium hafnate, strontium titanate, strontium hafnate, barium titanate, barium hafnate, barium zirconate and strontium zirconate. Methods for use of the foregoing catalytic materials in an OCM reaction are also provided. The methods comprise converting methane to ethane and/or ethylene in the presence of the catalytic materials.

In various embodiments of the foregoing, the diluent is nanostructured, for example nanowires are employed as diluents in various embodiments. In some of these embodiments, the nanowires comprise one or more of the foregoing diluent materials which are amenable to formation of nanowires. In other embodiments the diluent nanowires comprise a metal oxide. In some embodiments, the diluent portion in the catalyst/diluent mixture is about 0.01%, 10%, 30%, 50%, 70%, 90% or 99.99% (weight percent) or any other value between 0.01% and 99.9%. In some embodiments, the dilution is performed with the OCM catalyst ready to go, e.g. after calcination. In some other embodiments, the dilution is performed prior to the final calcination of the catalyst, i.e. the catalyst and the diluent are calcined together. In yet some other embodiments, the dilution can be done during the synthesis as well, so that, for example, a mixed oxide is formed. In still more embodiments, the catalyst diluent compositions is homogenized in a maximally dispersed state.

In certain embodiments, active catalyst to inert diluent ratio ranges from 5:95 to 95:5 (mass basis) in order to fulfill the desired performance criteria of managing localized temperature, catalyst activity and mechanical properties of the catalytic material. These criteria can vary within the catalyst packed bed as a function of location within the bed. For example for an adiabatic reactor with a large temperature rise through the reactor bed from inlet to outlet, a larger active catalyst to inert diluent ratio can be applied at the reactor inlet than the ratio used at the reactor outlet.

In some embodiments, the ratio of active catalyst to diluent ranges from about 1:99 to 99:1 (mass basis), for example from about 5:95 to 95:5, from about 10:90 to about 90:10, from about 25:75 to about 75:25 or is about 50:50. The ratio of active catalyst to diluent will vary depending on the particular catalytic reaction, reaction conditions, upon mechanical strength needs, thermal control needs, catalyst activity, and other factors as described elsewhere herein. One of ordinary skill in the art will recognize how to determine the appropriate ratio. For example, in certain embodiments the appropriate ratio can be determined empirically by determining which ratios provide optimum catalytic performance and/or prevent unwanted side reactions (e.g., reforming of methane during OCM).

Further dilution of the active catalyst loading can then easily be obtained by blending forms with no catalyst with forms containing active catalyst. The forms containing no active catalyst can be bonded at much higher temperature than the forms with active catalyst and can be typically made much more mechanically stronger than the active composite forms.

In some embodiments, the catalyst/diluent mixture comprises more than one catalyst and/or more than one diluent. In some other embodiments, the catalyst/diluent mixture is pelletized and sized, or made into shaped extrudates or deposited on a monolith or foam, or is used as it is. Such catalytic forms are described in more detail below. Methods of the invention include taking advantage of the very exothermic nature of OCM by diluting the catalyst with another catalyst that is completely or substantially inactive, or less active in the OCM reaction at the operating temperature of the first catalyst but active at higher temperature. In these methods, the heat generated by the hotspots of the first catalyst will provide the necessary heat for the second catalyst to become active.

In any of the above embodiments, the catalysts may comprise a $SiO_2$ support. Alternatively, the use of different supports such as $ZrO_2$, $HfO_2$ and $In_2O_3$ in any of the above embodiments has been shown to promote OCM activity at reduced temperature compared to the same catalyst supported on silica with limited reduction in selectivity.

In some embodiments of the foregoing blends, the first and second catalysts are physically blended. In related embodiments of the foregoing, rather than mixing the first and second catalysts, each catalyst type is segregated into different locations within the catalyst bed. For example the catalyst bed may comprise two layers of catalysts, wherein one layer contains the first catalyst and the other layer contains the second catalyst. The first catalyst may either be at the inlet end, or outlet end of the reactor. Other embodiments include various numbers of alternating layers (e.g., 1, 2, 3, 4, 5 or 6 or more layers) of first catalysts and second catalysts. Such stratified catalyst beds may serve to increase yield of desired C2 product while controlling the hot spots within the catalyst bed and/or reducing carbon monoxide in the product gas.

In various embodiments, blends of OCM active catalysts with other catalysts (which may also be OCM active) are provided. The provided blends have physical properties, such as crush strength, which are improved relative to the individual components. Furthermore, activity of the catalysts may be improved upon blending. The OCM active catalyst may be selected from any of active OCM catalyst, including those described herein and incorporated by reference. Similarly, the additional catalyst component may be selected from any number of catalysts, including bulk and nanostructured (e.g., nanowire) catalysts.

Accordingly, in some embodiments a formed catalytic material is provided, the formed catalytic material comprising:

(a) a perovskite; and
(b) a catalyst having the following formula:

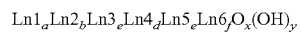

wherein:
Ln1, Ln2, Ln3, Ln4, Ln5 and Ln6 are each independently different lanthanide elements;
O is oxygen;
OH is hydroxy;
a is a number greater than 0; and
b, c, d, e, f, x and y are each independently numbers of 0 or greater, provided that at least one of x or y is greater than 0,
wherein the catalytic material further comprises a methane conversion of greater than 20% and a C2 selectivity of greater than 50% when the catalyst is employed as a heterogeneous catalyst in the oxidative coupling of methane at a temperatures ranging from about 550° C. to about 750° C.

In some embodiments, the perovskite comprises the following formula:

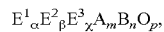

wherein:

A is a lanthanide or an element from group 4
B is an element from group 2;
$E^1$, $E^2$ and $E^3$ are each independently an element from groups 2, 3, 4 or the lanthanides;
O is oxygen;
α, β, χ are each independently a number of 0 or greater; and
m, n and p are each independently numbers greater than 0.

In various embodiments, B is Ba, Sr or Ca.
In other embodiments, A is Ce, Ti, Zr or Hf.
In still more embodiments of the foregoing perovskite, a is greater than 0. For example, in some embodiments the perovskite has the following formula:

$$E^1{}_\alpha A_m B_n O_p.$$

In other of the foregoing embodiments, $E^1$ is an element from group 2 or group 3 of the periodic table.

In some specific embodiments of the foregoing, the perovskite has the formula $ABO_3$, wherein A and B are as defined in any of the foregoing embodiments. In other of the foregoing embodiments, the perovskite comprises the following formula:

$$A^1{}_a A^2{}_b A^3{}_c B^1{}_x B^2{}_y B^3{}_z O_3$$

wherein:

$A^1$, $A^2$ and $A^3$ are each independently an element from the lanthanides or group 2, 3, 4, 6 or 13;
$B^1$, $B^2$ and $B^3$ are each independently a metal;
O is an oxygen anion;
a, b and c are each independently numbers ranging from 0 to 1, wherein the sum of a, b and c ranges from greater than 0 to 1; and
x, y and z are each independently numbers ranging from 0 to 1, wherein the sum of x, y and z does not exceed 1.

In some of the foregoing embodiments, the sum of a, b and c is 1.
In other of the foregoing embodiments, the sum of x, y and z is 1.
In some more specific embodiments, the perovskite has the following formula:

$$A^1{}_{(1-\lambda)} A^2{}_\lambda B^1{}_{(1-\delta)} B^2{}_\delta O_3$$

wherein:

$A^1$ and $A^2$ are each independently an element from the lanthanides or group 2, 3, 4, 6 or 13;
$B^1$ and $B^2$ are each independently a metal;
O is an oxygen anion; and
δ and λ are each independently numbers ranging from 0 to 1.

In some further embodiments of the above, δ and λ are each independently numbers ranging from greater than 0 to less than 1.

In still other embodiments, the perovskite comprises a lanthanide or alkaline earth metal dopant, or combinations thereof.

In yet more embodiments, $A^1$ and $A^2$ are each independently an alkaline earth metal.

In other embodiments of the foregoing perovskite, $B^1$ and $B^2$ are each independently a group 3 or group 4 element.

In some further embodiments, the perovskite comprises $Er/Ca/BaZrO_3$, $Nd/Ca/BaZrO_3$, $Eu/Ca/BaZrO_3$, $Ca_{(1-\lambda)}Sr_\lambda Y_{(1-\delta)}Zr_\delta O_3$, $Sr_\lambda Y_{(1-\delta)}Zr_\delta O_3$, $Ca/Nd/Ca_{(1-\lambda)}Sr_\lambda Y_{(1-\delta)}Zr_\delta O_3$, $Ca/Nd/SrY_{(1-\delta)}Zr_\delta O_3$, $Ca/Nd_2O_3/Ca_{(1-\lambda)}Sr_\lambda Y_{(1-\delta)}Zr_\delta O_3$, $La_{0.9}Sr_{0.1}Ga_{0.8}Mg_{0.2}O_3$, $BaCe_{0.7}Y_{0.2}Pr_{0.1}O_3$, $Ca/BaZrO_3$, $Y/BaZrO_3$, $BaZrO_3$, $Ca/Sr/BaZrO_3$, $SrCeO_3$, $Sr_\lambda Y_{(1-\delta)}Zr_\delta O_3$, $SrZrO_3$, $SrHfO_3$, $Mg/SrHfO_3$, $CaHfO_3$, $SrTbO_3$, $BaTiO_3$, $Y/SrZrO_3$, $Ce/GaPrO_3$, $SrCeO_3/SrCe_2O_4$, $Ce_{0.5}La_{0.4}Sr_{0.1}O_3$, $BaCeO_3$, $BaY_xCe_yO_3$, $BaY_xZr_yCe_zO_3$, $BaY_xLn_yCe_zO_3$, $BaZr_w Y_x Ln_y Ce_z O_3$, wherein δ, λ, w, x, y and z are numbers ranging from greater than 0 to 1, and Ln is a lanthanide element such as Gd or Nd. In some embodiments the sum of x and y is 1, or the sum of x, y and z is 1, or the sum of w, x, y and z is 1.

In other embodiments, the catalyst has the formula $Ln1_a Ln2_b O_x(OH)_y$. In some of these embodiments x is greater than zero. In other embodiments x is greater than zero and y is 0. In other embodiments x is greater than zero and y is greater than 0. In some other of these embodiments x is greater than zero.

In some other embodiments of the foregoing, b and y are both 0. For example, in some embodiments, b and y are both 0, and a and x are greater than 0. In some different embodiments, b and x are both 0, and a and y are greater than 0. In some other embodiments, y is 0, and a, b and x are greater than 0. In still other embodiments, x is 0, and a, b and y are greater than 0. In more embodiments, each of a, b, x and y is greater than 0.

In still other embodiments of the foregoing, the catalyst is a nanostructured catalyst. For example, in some embodiments the catalyst is a nanowire catalyst.

In more embodiments of the foregoing catalytic material, the catalyst further comprises a dopant selected from one or more elements from groups 2, 6 and the lanthanides. For example, in some embodiments the catalyst further comprises a dopant from each of groups 2, 6 and the lanthanides. In other embodiments, the catalyst further comprises a dopant from each of groups 2 and 6. Exemplary dopants from groups 2, 6 and the lanthanides include Mg, Ca, Sr, Ba, Mo, W, La, Ce, Nd and Gd.

In various different embodiments the invention provides a catalytic material comprising:

(a) an OCM active catalyst and
(b) a second catalyst having the following formula:

$$Ln1_a Ln2_b Ln3_c Ln4_d Ln5_e Ln6_f O_x(OH)_y$$

wherein:

Ln1, Ln2, Ln3, Ln4, Ln5 and Ln6 are each independently different lanthanide elements;
O is oxygen;
OH is hydroxy;
a is a number greater than 0; and
b, c, d, e, f, x and y are each independently numbers of 0 or greater, provided that at least one of x or y is greater than 0.

In some embodiments, the foregoing OCM active catalyst comprises a methane conversion of greater than 20% and a C2 selectivity of greater than 50% when the catalyst is employed as a heterogeneous catalyst in the oxidative coupling of methane at a temperatures ranging from about 550° C. to about 750° C., and wherein the OCM activity of the catalytic material is greater than either (a) or (b) alone In different embodiments, the second catalyst has the following formula:

$$Ln^1{}_x Ln^2{}_y O_z(OH)_n$$

wherein:

Ln1 and Ln2 are each independently different lanthanide elements;
O is oxygen;
OH is hydroxy; and n, x, y and z are each independently numbers of 0 or greater, provided that at least one of x or y is greater than 0 and at least one of n or z is greater than 0.

In some embodiments, the OCM active catalyst is a bulk catalyst. In other embodiments, the OCM active catalyst is a nanostructured catalyst, such as a nanowire.

In some embodiments, the second catalyst is also an OCM active catalyst. In some embodiments, the second catalyst comprises a nanostructured catalyst. For example, in some embodiments the second catalyst comprises catalytic nanowires. In various embodiments, the second catalyst (e.g., catalytic nanowires) comprise a rare earth element. In other embodiments, the second catalyst (e.g., catalytic nanowires) comprise lanthanum, cerium, praseodymium, neodymium, samarium, europium, gadolinium, terbium, dysprosium, holmium, erbium, thulium, ytterbium, lutetium or combination thereof. For example, in some embodiments the second catalyst (e.g., catalytic nanowires) comprise a lanthanum/neodymium oxide, a lanthanum/cerium oxide, a neodymium/cerium oxide, a lanthanum/samarium oxide, a neodymium/samarium oxide, a europium/neodymium oxide, a lanthanum/erbium oxide, a neodymium/erbium oxide or a europium/lanthanum oxide.

In any of the foregoing embodiments, the OCM active catalyst comprises a group 4 element, for example a compound comprising an alkaline earth metal and a group 4 element. For example, in some embodiments the alkaline earth metal is magnesium, calcium, strontium or barium. In some other embodiments, the group 4 element is titanium, zirconium or hafnium. For example, in certain embodiments the OCM active catalyst comprises an alkaline earth metal and titanium, zirconium or hafnium. The OCM active catalyst may also further include optional dopants, for example alkaline earth metal dopants such as magnesium, calcium, strontium or barium.

In any of the foregoing embodiments, the OCM active catalyst comprises a group 6 element, for example a compound comprising an alkaline earth metal and a group 6 element. For example, in some embodiments the alkaline earth metal is magnesium, calcium, strontium or barium. In some other embodiments, the group 6 element is tungsten. For example, in certain embodiments the OCM active catalyst comprises an alkaline earth metal and tungsten. The OCM active catalyst may also further include optional dopants, for example alkaline earth metal dopants such as magnesium, calcium, strontium or barium.

In any of the foregoing embodiments, the OCM active catalyst comprises a group 13 element, for example a compound comprising an alkaline earth metal and a group 13 element. For example, in some embodiments the alkaline earth metal is magnesium, calcium, strontium or barium. In some other embodiments, the group 13 element is aluminum. For example, in certain embodiments the OCM active catalyst comprises an alkaline earth metal and aluminum. The OCM active catalyst may also further include optional dopants, for example alkaline earth metal dopants such as magnesium, calcium, strontium or barium.

In any of the foregoing embodiments, the OCM active catalyst comprises one or more lanthanide elements, for example a compound comprising an alkaline earth metal and one or more lanthanide elements. For example, in some embodiments the alkaline earth metal is magnesium, calcium, strontium or barium. In some other embodiments, the lanthanide element is Gd or Nd, or combinations thereof. For example, in certain embodiments the OCM active catalyst comprises an alkaline earth metal and Gd or Nd, or combinations thereof. The OCM active catalyst may also further include optional dopants, for example alkaline earth metal dopants such as magnesium, calcium, strontium or barium.

The weight ratio of the OCM catalyst to the second catalyst (e.g., catalytic nanowires) can vary from about 1% to about 99%, for example from about 90% to about 50%, from about 80% to about 60% or from about 75% to about 65%. In some embodiments, the weight ratio of OCM active catalyst to catalytic nanowires is about 70%.

The strength of the blended catalytic materials is improved relative to the individual components. For example, in some embodiments the catalytic material has a crush strength of greater than about 20 N/mm, greater than about 25 N/mm, greater than about 30 N/mm, greater than about 35 N/mm or even greater than about 40 N/mm when tested according to ASTM D4179. In some embodiments, the strength of the blended catalytic materials is determined for 6 mm diameter cylinders having an aspect ratio of 1, and which have been prepared by pressing at 1 ton using a manual hydraulic pellet press.

The catalytic performance of the blended catalytic materials is also surprisingly better than the individual components. In some embodiments, the C2+ selectivity of the catalytic material in the OCM reaction is greater than about 60%, 65%, 70% or even 75% when the OCM reaction is conducted at temperatures of about 600° C. or lower and pressures ranging from about 6-10 bar, for example about bar.

In other embodiments, the invention provides a catalytic material having enhanced physical properties, such as reduced shrinkage, while maintaining the same or better catalytic properties. While not wishing to be bound by theory, "shrinkage" as used herein is thought to be related to sintering of the catalytic materials, which results in volume contraction. For example, certain catalysts have excellent catalytic performance in OCM, ODH and/or other reactions, but suffer from significant shrinkage when heated to temperatures needed for these reactions. Such shrinkage can cause problems on large scale reactors by giving dead space at the top of the reactor resulting in increased possibilities of auto-ignition of feed gas. Thus the commercial applications of such catalysts are limited. However, experiments performed in support of the present invention have shown that addition of certain elements, such as group 4 elements (e.g., titanate, zirconates, and/or halfnates) can reduce the shrinkage associated with some heterogeneous catalysts, while improving (or at least not reducing) the catalytic performance of the catalyst. In some embodiments the group 4 element is titanium, zirconium or hafnium and the catalytic materials comprise calcium titanate, calcium hafnate, strontium titanate, strontium hafnate, barium titanate, barium hafnate, barium zirconate and/or strontium zirconate.

Other experiments performed in support of different embodiments of the present invention have identified different additives which prevent or reduce shrinkage of catalytic materials. For example, in some embodiments group 13 elements are included in the catalytic materials, and such catalytic materials show a reduced tendency to shrink at temperatures employed for OCM. The group 13 elements can be used in addition to the group 4 element, such as a titanate, zirconate or hafnate, or the group 13 element may be used separately. In some embodiments, the group 13 element is boron, gallium or aluminum.

In various embodiments of the foregoing catalytic material, the catalytic material further comprises one or more dopant. In some embodiments, the dopant is an alkaline earth metal such as magnesium, calcium, strontium or barium. The one or more dopant of certain other embodiments may be selected from the dopants provided in in co-pending U.S. application Ser. No. 13/115,082 (U.S. Pub. No. 2012/0041246); Ser. No. 13/479,767 (U.S. Pub. No. 2013/0023709); Ser. No. 13/689,611 (U.S. Pub. No. 2013/0165728); Ser. No. 13/689,514 (U.S. Pub. No. 2013/0158322) and U.S. Provisional Application Nos. 61/794,486; 61/909,840; and 61/988,063, the full disclosures of which are incorporated herein by reference at least for the purpose of providing exemplary dopants.

In some different embodiments a catalytic material comprising a group 4, 6 or 13 element, such as a tungstate, aluminate, titanate, zirconate and/or hafnate compound, and an active catalyst (e.g., OCM active) are provided. In some embodiments, the catalytic material comprises a group 4 element, such as a titanate, zirconate and/or hafnate compound, and an active catalyst. In some embodiments, the group 4, 6 or 13 element is in combination with an alkaline earth metal element. For example, in some embodiments, the catalytic materials comprise an alkaline earth metal titanate, alkaline earth metal zirconate or alkaline earth metal hafnate, and the active catalyst is an OCM active catalyst.

In other embodiments, the catalytic materials comprise:

a) an alkaline earth metal aluminate, tungstate, titanate, zirconate or hafnate; and (b) a catalyst having the following formula:

$$Ln1_aLn2_bLn3_cLn4_dLn5_eLn6_fO_x(OH)_y$$

wherein:

Ln1, Ln2, Ln3, Ln4, Ln5 and Ln6 are each independently different lanthanide elements;

O is oxygen;

OH is hydroxy;

a is a number greater than 0; and b, c, d, e, f, x and y are each independently numbers of 0 or greater, provided that at least one of x or y is greater than 0.

In some embodiments, c is a number greater than 0. In other embodiments, c and d are each independently a number greater than 0. In still more embodiments, c, d and e are each independently a number greater than 0.

In other different embodiments of the foregoing catalytic material, the weight ratio of the alkaline earth metal aluminate, tungstate, titanate, zirconate or hafnate to the catalyst ranges from about 80% to about 60%.

In some further embodiments, the catalytic materials comprise:

(a) an alkaline earth metal titanate, zirconate or hafnate; and (b) a catalyst having the formula $Ln1_aLn2_bO_x(OH)_y$.

In some embodiments of the above, the catalytic material comprises a methane conversion of greater than 20% and a C2 selectivity of greater than 50% when the catalytic material is employed as a heterogeneous catalyst in the oxidative coupling of methane at a temperatures ranging from about 550° C. to about 750° C.

In some of the foregoing embodiments, the catalytic materials comprise an alkaline earth metal tungstate or alkaline earth metal aluminate, and the active catalyst is an OCM active catalyst. For example, in some embodiments the catalytic materials comprise strontium aluminate, strontium tungstate, barium tungstate, calcium titanate, calcium hafnate, strontium titanate, strontium hafnate, barium titanate, barium hafnate, barium zirconate, barium zirconate and/or strontium zirconate. In certain embodiments, the active catalyst is a nanostructured catalyst, such as a nanowire catalyst. In other embodiments, the active catalyst is a bulk catalyst. In some of these embodiments, the alkaline earth metal aluminate, tungstate, titanate, zirconate or hafnate is nanostructured, such as a nanowire.

In some other specific embodiments, the catalytic material comprises calcium titanate, calcium hafnate, strontium titanate, strontium hafnate, barium titanate, barium hafnate, barium zirconate, calcium zirconate and/or strontium zirconate, and an OCM active catalyst. In certain embodiments, the OCM active catalyst (e.g., catalytic nanowires) has the following formula:

$$Ln1_xLn2_yO_z(OH)_n$$

wherein:

Ln1 and Ln2 are each independently different lanthanide elements;

O is oxygen;

OH is hydroxy; and n, x, y and z are each independently numbers of 0 or greater, provided that at least one of x or y is greater than 0 and at least one of n or z is greater than 0.

In some embodiments, the catalyst (e.g., an OCM active catalyst) comprises lanthanum, cerium, praseodymium, neodymium, samarium, europium, gadolinium, terbium, dysprosium, holmium, erbium, thulium, ytterbium, lutetium or combinations thereof. In some other embodiments the OCM active catalyst comprises a lanthanum/neodymium oxide, a lanthanum/cerium oxide, a neodymium/cerium oxide, a lanthanum/samarium oxide, a neodymium/samarium oxide, a europium/neodymium oxide, a lanthanum/erbium oxide, a neodymium/erbium oxide or a europium/lanthanum oxide.

For example, in some embodiments, the OCM active catalyst comprises catalytic nanowires. In some embodiments, the catalytic nanowires comprise lanthanum, cerium, praseodymium, neodymium, samarium, europium, gadolinium, terbium, dysprosium, holmium, erbium, thulium, ytterbium, lutetium or combinations thereof. In some other embodiments the catalytic nanowires comprise a lanthanum/neodymium oxide, a lanthanum/cerium oxide, a neodymium/cerium oxide, a lanthanum/samarium oxide, a neodymium/samarium oxide, a europium/neodymium oxide, a lanthanum/erbium oxide, a neodymium/erbium oxide or a europium/lanthanum oxide.

The weight ratio of the group 4, 6 or 13 element-containing compound (e.g., zirconate) to the catalytic nanowires can vary from about 1% to about 99%, for example from about 90% to about 50%, from about 80% to about 60% or from about 75% to about 65%. In some embodiments, the weight ratio of the zirconate to catalytic nanowires is about 70%.

Although any group 4 element-containing compound may be used in the foregoing catalytic materials, specific embodiments are directed to catalytic materials comprising compounds of alkaline earth metals and group 4 elements. For example, in some embodiments the catalytic materials comprise strontium aluminate, strontium tungstate, barium tungstate, calcium titanate, calcium hafnate, strontium titanate, strontium hafnate, barium titanate, barium hafnate, barium zirconate, calcium zirconate and/or strontium zirconate. In some other embodiments the catalytic materials comprise calcium titanate, calcium hafnate, strontium titanate, strontium hafnate, barium titanate, barium hafnate, barium zirconate and/or strontium zirconate. In any of the foregoing embodiments, the catalyst is a lanthanum and/or neodymium-containing catalyst.

Any morphology of group 4 element-containing compound may be employed. For example, in some embodiments the group 4 element-containing compound is bulk, and in other embodiments the group 4 element-containing compound is nanostructured, such as a nanowire.

In various embodiments of the foregoing catalytic material, the catalytic material further comprises one or more dopant. In some embodiments, the dopant is an alkaline earth metal such as magnesium, calcium, strontium or barium. The one or more dopant of certain other embodiments may be selected from the dopants provided in in co-pending U.S. application Ser. No. 13/115,082 (U.S. Pub. No. 2012/0041246); Ser. No. 13/479,767 (U.S. Pub. No. 2013/0023709); Ser. No. 13/689,611 (U.S. Pub. No. 2013/0165728); Ser. No. 13/689,514 (U.S. Pub. No. 2013/0158322) and U.S. Provisional Application Nos. 61/794,486; 61/909,840; and 61/988,063, the full disclosures of which are incorporated herein by reference at least for the purpose of providing exemplary dopants.

As noted above, one particular advantage of the catalytic materials comprising a group 4 element-containing compound (e.g., calcium titanate, calcium hafnate, strontium titanate, strontium hafnate, barium titanate, barium hafnate, barium zirconate and/or strontium zirconate) is the reduced shrinkage at the temperatures required for many petrochemical catalytic reactions, such as OCM. In various embodiments, the catalytic material has a volume loss of less than 10%, less than 5%, less than 2% or even less than 1% when heated to 900° C. in static air for 100 hours.

Advantageously, the group 4 element-containing catalytic materials are less susceptible to shrinkage, but their catalytic performance remains substantially the same as the catalyst without the added group 4 element. Accordingly, in some embodiments, the C2+ selectivity of the group 4 element-containing catalytic material in the OCM reaction is greater than about 50%, 55%, 60%, 65%, 70% or even 75% when the OCM reaction is conducted at temperatures of about 600° C. or lower. In various embodiments of the foregoing, the C2+ selectivity of the group 4 element-containing catalytic material in the OCM reaction is determined at about 6-10 barg, for example about 8 barg.

In any of the foregoing embodiments of catalytic materials having reduced shrinkage, the catalytic material comprises:

(a) an OCM active catalyst; and
(b) a second catalyst comprising the following formula:

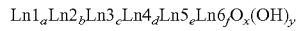

$Ln1_a Ln2_b Ln3_c Ln4_d Ln5_e Ln6_f O_x(OH)_y$ wherein:
Ln1, Ln2, Ln3, Ln4, Ln5 and Ln6 are each independently different lanthanide elements;
O is oxygen;
OH is hydroxy;
a is a number greater than 0; and
b, c, d, e, f, x and y are each independently numbers of 0 or greater, provided that at least one of x or y is greater than 0 wherein the catalytic material has a volume loss of less than 5% when heated to 900° C. in air for 100 hours.

In certain embodiments of the foregoing, the OCM activity of the catalytic material is greater than either (a) or (b) alone.

In various embodiments, of the foregoing a method for reducing shrinkage of a catalytic material is provided. The method comprises including a group 4 and/or group 13 element in the catalytic material. Exemplary group 4 and/or group 13 elements include those described above with respect to the catalytic material.

In other embodiments, a catalytic material comprising a first and second catalyst is provided, wherein the first catalyst has activity for oxidative coupling of methane and the second catalyst has activity for oxidation of carbon monoxide.

In some embodiments, the second catalyst comprises a transition metal oxide. For example in some embodiments the second catalyst comprises an oxide of titanium, chromium, manganese, iron, cobalt, nickel, copper, zinc, zirconium, molybdenum, palladium, silver, tungsten, platinum, gold, or any combination thereof.

In various embodiments of the foregoing, the weight percent of the second catalyst in the catalytic material ranges from about 0.1% to about 5%. For example, in some embodiments the weight percent of the second catalyst in the catalytic material ranges from about 0.1% to about 3%.

In other embodiments, the first catalyst comprises a rare earth oxide. In some embodiments, the rare earth oxide is an oxide of a lanthanide, an actinide or combinations thereof. In some embodiments, the rare earth oxide comprises lanthanum, cerium, praseodymium, neodymium, samarium, europium, gadolinium, terbium, dysprosium, holmium, erbium, thulium, ytterbium, lutetium or combinations thereof. In some other embodiments the rare earth oxide comprises a lanthanum/neodymium oxide, a lanthanum/cerium oxide, a neodymium/cerium oxide, a lanthanum/samarium oxide, a neodymium/samarium oxide, a europium/neodymium oxide, a lanthanum/erbium oxide, a neodymium/erbium oxide or a europium/lanthanum oxide. For example, in some embodiments the rare earth oxide is a lanthanum, cerium or yttrium oxide, or combinations thereof.

In other embodiments, the first catalyst comprises a transition metal, for example manganese. In some embodiments, the first catalyst comprises a manganese tungstate.

In other embodiments of the foregoing, the first catalyst further comprises a dopant. For example, in some embodiments the dopant is silicon, strontium or sodium, or combinations thereof. The dopant of certain other embodiments may be selected from the dopants provided in in co-pending U.S. application Ser. No. 13/115,082 (U.S. Pub. No. 2012/0041246); Ser. No. 13/479,767 (U.S. Pub. No. 2013/0023709); Ser. No. 13/689,611 (U.S. Pub. No. 2013/0165728); Ser. No. 13/689,514 (U.S. Pub. No. 2013/0158322) and U.S. Provisional Application Nos. 61/794,486; 61/909,840; and 61/988,063, the full disclosures of which are incorporated herein by reference at least for the purpose of providing exemplary dopants.

A method for oxidative coupling of methane comprising use of the foregoing catalytic material is also provided, the method comprising contacting methane and oxygen with the foregoing catalytic material (i.e., comprising first and second catalysts) at temperatures ranging from about 525° C. to about 825° C. to form a product gas comprising C2's, carbon dioxide and substantially no carbon monoxide.

In some embodiments of the foregoing method, the ratio of carbon monoxide in the product gas relative to the concentration of carbon dioxide in the product gas ranges from about 0.1 to 10 to about 0.2 to 1.0.

In other embodiments, the method further comprises converting the carbon dioxide into methane. For example, in some embodiments the carbon dioxide is converted into methane via a reverse water gas shift or Sabatier reaction.

3. Catalytic Forms

The catalytic materials may also be employed in any number of forms. In this regard, the physical form of the catalytic materials may contribute to their performance in various catalytic reactions. In particular, the performance of a number of operating parameters for a catalytic reactor that impact its performance are significantly impacted by the form in which the catalyst is disposed within the reactor. As noted elsewhere herein, the catalyst may be provided in the form of discrete particles, e.g., pellets, extrudates or other formed aggregate particles, or it may be provided in one or more monolithic forms, e.g., blocks, honeycombs, foils, lattices, etc. These operating parameters include, for example, thermal transfer, flow rate and pressure drop through a reactor bed, catalyst accessibility, catalyst lifetime, aggregate strength, performance, and manageability.

In a certain embodiment, the form of the catalyst can directly impact the flow rate and pressure drop through a catalyst bed. In particular, the pressure drop across a catalyst bed, which can be estimated using the Ergun equation, is a function of the bed void volume, where increased void spaces, e.g., between catalyst particles, provides easier flow through the catalyst bed, and thus a smaller pressure drop across the catalyst bed. Pressure drop across the bed is also a function of size of the formed catalyst particles as defined by the effective particle diameter: $Dp,eq=6Vp/Sp$, where Vp is the volume of formed catalyst and Sp is the surface area of the catalyst. As the effective particle diameter increases the pressure drop decreases. With reference to previously described OCM reactions, the issue of pressure drop was of little importance since such reactions were carried out at relatively high pressures and small scales. In accordance with preferred low pressure OCM reactions described herein, however, it is desirable to maintain an entire reactor system at pressures and other operating conditions, that are more conventionally found in gas and other chemical processing systems. As such, it is desirable to provide reactor systems that operate at inlet pressures of from about 15 psig to about 150 psig with relatively controlled pressure drops across the reactor bed. Thus, in accordance with certain embodiments, catalyst forms are selected to provide the reactors that have inlet pressures of between about 15 and 300 psig, with pressure drops that average between about 0.1 psig/linear foot of reactor bed depth to about 10 psig/linear foot of reactor bed depth. Typically the catalytic form is chosen such that the pressure drop across a bed comprising the catalytic forms will range from about 0.05 bar/m to about 0.4 bar/m at gas head space velocities (GHSV) ranging from about 15,000 $hr^{-1}$ at STP to about 50,000 $h^{-1}$ at STP. The pressure drop will typically increase as the aspect ratio of the catalyst bed increases and/or the diameter of the catalyst bed decreases. Typical catalyst bed aspect ratios (length to diameter) range from about 0.1 to about 3, 0.1 to about 2, from about 0.3 to about 1, for example about 0.5 to about 0.75. Typical catalyst bed diameters range from about 3 feet to about 20 feet, for example about 5 feet to about 15 feet.

A variety of catalyst forms may be used to achieve these parameters as described herein. In particular, catalyst forms that provide void fractions within the reactor of from about 35% to about 70%, and preferably between about 45% and about 65%, will generally provide void fractions in an advantageous range. In some embodiments, the void fraction ranges from 60% to 70%, for example from 64% to 67%. Notwithstanding the foregoing, a range of effective void fractions may be selected by selecting the appropriate particle size, to meet the desired pressure drop while still providing the requisite catalytic activity. In general, the catalyst particles will typically range from about 0.25 mm to about 50 mm in at least one cross sectional dimension, with some embodiments having particle sizes for formed aggregates ranging from about 0.25 mm to about 50 mm or to about 40 mm, from about 4 mm to about 28 mm or from about 6 mm to about 25 mm, or from about 2 mm to about 25 mm in at least one cross sectional dimension. For example, in some embodiments the catalyst particles will typically be between about 4 mm and about 28 mm in at least one cross sectional dimension, with preferred particle sizes for formed aggregates being between about 10 mm and about 25 mm in at least one cross sectional dimension. In other embodiments, at least one cross sectional dimension ranges from about 10 mm to about 16 mm, 14 mm to about 20 mm or about 18 mm to about 25 mm.

In accordance with certain embodiments, the foregoing parameters are adjusted in the context of maintaining other parameters in desired ranges. In particular, adjustment of void fraction and pressure drop is generally carried out in a manner that does not significantly adversely affect catalytic activity, or catalyst lifetime. In particular, preferred catalyst forms will provide desired pressure drops, while also providing desired performance activity. In general, catalyst forms that provide higher surface to volume ratios, while maintaining desired void fractions are preferred. Surface to volume ratios increase as the effective particle diameter decreases. Therefore, it is desirable to have as small an effective diameter as possible while still meeting the pressure drop requirements. Forms with smaller effective diameters can be used but the void fraction must increase to meet pressure drop requirements. In certain embodiments, catalyst forms that accomplish this include, e.g., rings, pentagons, ovals, tubes, trilobes, trilobe rings, wagon wheels, monoliths, quadralobes, quadralobe rings, shapes with fluted edges and the like. In general, the surface area to volume ratio for the formed aggregate catalyst particles of the invention will range from about 0.1 $mm^{-1}$ to 10 $mm^{-1}$, and in some embodiments from about 0.5 $mm^{-1}$ to about 5 $mm^{-1}$ and in other embodiments from about 0.1 $mm^{-1}$ to about 1 $mm^{-1}$.

In a further aspect, it is also desirable that the catalyst forms used will have crush strengths that meet the operating parameters of the reactor systems. In particular, a catalyst crush strength should generally support both the pressure applied to that particle from the operating conditions, e.g., gas inlet pressure, as well as the weight of the catalyst bed. In general, it is desirable that a catalyst particle has a crush strength that is greater than about 0.2 $N/mm^2$, and in some embodiments greater than about 2 $N/mm^2$, for example greater than about 0.5 $N/mm^2$, and preferably greater than about 2 $N/mm^2$. In some embodiments, the crush strength is greater than about 0.25 $N/mm^2$, or greater than about 1 $N/mm^2$, such as about 10 $N/mm^2$. As will be appreciated, crush strength may generally be increased through the use of catalyst forms that are more compact, e.g., having lower surface to volume ratios, or that have a higher catalyst density. However, adopting such forms may adversely impact performance. Accordingly, forms are chosen that provide the above described crush strengths within the desired activity ranges, pressure drops, etc. Crush strength is also impacted though use of binder and preparation methods (e.g., extrusion or pelleting).

In addition, in particularly preferred embodiments, the use of catalytic nanowire materials can enhance crush strength as they can operate as binders themselves, and thus impart greater structural integrity and crush strength to the catalyst particle.

Another catalyst form characteristic that can impact overall reactor performance is the accessibility of the catalyst material within a catalyst particle. This is generally a function of the surface to volume ratio of the catalytic portion of a given catalyst particle. For a homogeneously dispersed catalyst, this relates to the surface:volume ratio of the entire particle, while for catalyst coated particles or forms, this would relate to the surface:volume ratio of the coating porosity of the catalyst particle. While this ratio is a function of the catalyst particle shape, e.g., spherical particles will have lower surface:volume ratios than other shapes, it can also be substantially impacted by the porosity of the catalyst particle. In particular, highly porous catalyst particles have larger effective diffusivities allowing for greater utilization of the formed catalyst in the reactor. Again, while highly porous catalyst particles may provide greater accessibility, they should generally do so while maintaining desired crush strengths, etc., which can be adversely impacted by increasing porosity. In particularly preferred aspects, catalyst particles or other forms will include a porosity of between about 10% and about 80% while maintaining the desired crush strengths above about 0.2 N/mm$^2$. In more preferred aspects, the porosity will be between about 40% and about 60%.

For example, in some embodiments the catalytic materials are in the form of an extrudate or pellet. Extrudates may be prepared by passing a semi-solid composition comprising the catalytic materials through an appropriate orifice or using molding or other appropriate techniques. Other catalytic forms include catalysts supported or impregnated on a support material or structure. In general, any support material or structure may be used to support the active catalyst. The support material or structure may be inert or have catalytic activity in the reaction of interest (e.g., OCM). For example, catalysts may be supported or impregnated on a monolith support. In some particular embodiments, the active catalyst is actually supported on the walls of the reactor itself, which may serve to minimize oxygen concentration at the inner wall or to promote heat exchange by generating heat of reaction at the reactor wall exclusively (e.g., an annular reactor in this case and higher space velocities). Exemplary catalytic forms useful in the practice of the present invention are described in more detail below.

The surface area to volume ratio of the catalytic form is an important parameter in determining the maximal flux of reagents and product molecules entering or leaving the catalytic form. This parameter also affects the temperature gradient throughout the form since increase in relative surface area tends to favor heat removal and minimize thickness of the form, hence limiting peak temperatures at the core of the particle. In some cases, heat removal from the catalyst particle is not favored, such that there is a large temperature difference between the catalyst particle and surrounding gas. In this case, a smaller catalytic form envelope surface area to catalytic form envelope volume ratio is desired, ranging from 0.1 mm$^{-1}$ to about 4 mm$^{-1}$ or from 0.1 mm$^{-1}$ to about 0.5 mm$^{-1}$. In the particular case of OCM active catalytic forms, the catalytic form envelope surface area to catalytic form envelope volume ratio ranges from about 0.5 to about 4 mm$^{-1}$ or from about 0.25 mm$^{-1}$ to about 4 mm$^{-1}$. when the space velocities range from about 10,000 to about 200,000 hr$^{-1}$, for example from 20,000 hr$^{-1}$ to 32,000 hr$^{-1}$. At ratios larger than 4 mm$^{-1}$, the same catalytic forms may become mechanically weak, and in this case a coated substrate might be preferable. At ratios lower than 0.5 only a fraction of the catalyst is accessible to the reagent as the form gets too thick and transport limitations can become a limiting factor.

In some cases, it will be particularly desirable to provide catalytic materials in which the active catalyst material is substantially homogeneously dispersed. As used herein, homogeneously dispersed means that across a given catalyst particle, the concentration of active catalyst does not vary by more than 25%, preferably not greater than 10%. For particularly preferred materials, this is advantageously achieved through the use of catalytic nanowire materials, which provide a more uniform dispersion profile within catalyst formulations, e.g., including diluents, binders etc.

For catalysts which are heterogeneously dispersed within the catalytic form (e.g., catalysts disposed on the surface of a support), the above mentioned ratio can become quite small (e.g., from about 0.1 to about 0.5) as effective catalyst used can be maintained by preferentially concentrating the active catalyst component at the surface of the form (e.g., adhered to surface of a support).

The density of the formed catalytic material can affect various factors such as the porosity, effective surface area, pressure drop, crush strength, etc. In various embodiments, the density of the formed catalytic material ranges from about 0.5 g/cm$^3$ to about 5.0 g/cm$^3$ or to about 3.0 g/cm$^3$. For example, in some more specific embodiments, the density ranges from about 1.50 g/cm$^3$ to about 3.5 g/cm$^3$, to about 3.0 g/cm$^3$ or from about 2.0 g/cm$^3$ to about 2.75 g/cm$^3$, for example about 2.5 g/cm$^3$. The foregoing densities refer to the density of the catalytic material excluding the volume associated with the catalytic material's porosity and void volume.

In certain preferred embodiments, the catalytic materials will satisfy one, two, or more of the foregoing parameters. For example, the catalyst particles (or catalytic materials made therefrom, e.g., formed aggregate) may include one or more of a particle size and/or shape that yields a bed void volume fraction of 35% to 70%, a crush strength of greater than 1 N/mm$^2$, a porosity ranging from 10% to 80% and a surface area to volume ratio ranging from 0.1 mm$^{-1}$ to 10 mm$^{-1}$. In other embodiments, the catalyst particles (or catalytic materials made therefrom, e.g., formed aggregate) may include one or more of a particle size that yields a bed void volume fraction of 45% to 65%, a crush strength of greater than 1 N/mm$^2$, a porosity ranging from 40% to 60% and a surface area to volume ratio ranging from 0.1 mm$^{-1}$ to 5 mm$^{-1}$.

In still more embodiments, the catalyst particles (or catalytic materials made therefrom, e.g., formed aggregate) may include one or more of a particle size that yields a bed void volume fraction of 40% to 60%, a crush strength of greater than 0.2 N/mm$^2$, a porosity ranging from 10% to 80% and a surface area to volume ratio ranging from 0.1 mm$^{-1}$ to 10 mm$^{-1}$. In some embodiments, the catalyst particles (or catalytic materials made therefrom, e.g., formed aggregate) may include one or more of a particle size that yields a bed void volume fraction of 35% to 70%, a crush strength of greater than 0.2 N/mm$^2$, a porosity ranging from 10% to 80% and a surface area to volume ratio ranging from 0.1 mm$^{-1}$ to 10 mm$^{-1}$. In other embodiments, the catalyst particles (or catalytic materials made therefrom, e.g., formed aggregate) may include one or more of a particle size that yields a bed void volume fraction of 35% to 70%, a crush strength of greater than 1 N/mm$^2$, a porosity ranging from 40% to 60% and a surface area to volume ratio ranging from 0.1 mm$^{-1}$ to 10 mm$^{-1}$. In still other embodiments, the catalyst particles (or catalytic materials made therefrom, e.g., formed aggregate) may include one or more of a particle size that yields a bed void volume fraction of 35% to 70%, a crush strength of greater than 0.2/mm$^2$, a porosity ranging from 10% to 80% and a surface area to volume ratio ranging from 0.1 mm$^{-1}$ to 5 mm$^{-1}$.

In some of the foregoing embodiments, wherein the catalytic materials satisfy one, two or more of the foregoing parameters, the catalyst particles (or catalytic materials made therefrom, e.g., formed aggregate) additionally comprise at least one cross sectional dimension ranging from 0.25 mm to 50 mm. In other embodiments, at least one cross sectional dimension ranges from 4 mm to 28 mm. Any of the foregoing catalytic materials may also comprise a BET surface area ranging from about 0.1 m$^2$/g to about 50 m$^2$/g. BET (Brunauer/Emmett/Teller) refers to a technique for determining surface area, which employs an inert gas, for example nitrogen, to measure the amount of gas adsorbed on a material and can be used to determine the accessible surface area of materials.

The total surface area (including pores) by weight of the catalytic form is primarily determined by the composition (i.e., catalyst, binder, diluent, etc.) of the form. When low surface area diluent is used then most of the surface area of the solid comes from the OCM active catalyst. In certain embodiments, the surface area of the catalytic materials ranges from about 0.1 m$^2$/g to about 50 m$^2$/g depending on catalyst dilution when using low surface area diluent material.

One of the advantages of catalytic materials employing nanowire structured catalysts is that they can form aggregates with large pore volume presenting interconnected large pores. Typically pore volume fraction in catalytic materials containing a nanowire catalyst ranges from 20 to 90% (vol/vol) and in some embodiments can be modified by adjusting the ratio of diluent (typically lower porosity and lower surface area) to nanowire aggregates, and in other embodiments can be modified by selecting nanowires with the appropriate aspect ratio. When the pore structure is mostly dominated by the nanowire aggregates pores above 20 nm are the main source of pore volume within the composite form. Some embodiments include catalytic forms which have highly interconnected and large openings relative to reagent and product molecules, thus promoting diffusion through the form. This property can also be used when reactant flow is forced through the composite as for example in wall through flow monoliths for diesel soot removal.

In some examples, the catalytic forms are chosen in order to mitigate potential hot spots resulting from highly exothermic reactions. For example, in some embodiments the heat conductivity of the form is increased including material with high heat conductivity in the form. Examples of materials used to increase the heat conductivity include, but are not limited to, SiC. In other embodiments, the rate of heat generation per unit volume of form can be decreased, for example by dilution of the form with an inactive material, thus adjusting the catalyst surface area per form volume and form porosity. At the same time the selection of the diluent to promote heat transfer through the form can be beneficial in reducing temperature gradient through the form. In this regard, any of the diluents described herein can be employed in the catalytic form for the purpose of promoting heat transfer and reducing the temperature gradient through the form.

In another embodiment, the thermal transfer properties of the catalytic form are controlled by heterogeneous loading of active catalyst throughout the form. For example, in some embodiments OCM catalyst can be coated upon a catalytically inert support resulting in an overall low catalyst loading per form and limited temperature gradient through the form (since there is no heat generation in the core of the particle). Again, the thickness of such coating layers will depend upon the desired ratio of catalyst to inert support and/or catalyst loading. In other embodiments, it may be desirable to increase the temperature gradient through the form in some locations of the pack-bed reactor. In this case active catalyst may be preferentially loaded in the core of the form with an outer shell containing low active catalyst amounts. Such strategies are discussed in more detail below.

In some embodiments a support (e.g., MgO, CaO, B$_2$O$_3$, Ga$_2$O$_3$, Al$_2$O$_3$, In$_2$O$_3$, SrAl$_2$O$_4$, B$_4$SrO$_7$, CaCO$_3$, SrCO$_3$, inorganic oxides, SiO$_2$, TiO$_2$, SrO, BaO, ZrO$_2$, ZnO, LiAlO$_2$, MgAl$_2$O$_4$, MnO, MnO$_2$, Mn$_3$O$_4$, La$_2$O$_3$, Ln$_2$O$_3$, where Ln is a lanthanide element, AlPO4, SiO$_2$/Al$_2$O$_3$, activated carbon, silica gel, zeolites, activated clays, activated Al$_2$O$_3$, SiC, diatomaceous earth, magnesia, aluminosilicates, calcium aluminate, support nanowires or combinations thereof) may be used in the form of a pellet or extrudate or monolith (e.g., honeycomb) structure, and the catalysts may be impregnated or supported thereon. In other embodiments, a core/shell arrangement is provided and the support material may form part of the core or shell. For example, a core of MgO, CaO, CaCO$_3$ or SrCO$_3$ may be coated with a shell of catalyst.

In certain embodiments, the catalyst materials are provided as a formed aggregate that comprises the underlying catalyst material, and in many cases, one or more additional materials, including dopants, diluents, binders, supports, or other different catalyst materials, as described elsewhere herein. These formed aggregates may be prepared by a large number of different forming processes, including for example, extrusion processes, casting processes, press forming processes, e.g., tablet processes, free form aggregation processes (e.g., spray aggregation), immersion, spray, pan or other coating or impregnation processes and/or agglomeration/granulation techniques. These formed aggregates may range in size from small particles, e.g., less than 1 mm in cross sectional dimension, to moderate size particles ranging from 1 mm to 2 cm in cross sectional dimension, e.g., for typical pellet or extrudate sized particles, to much larger forms, ranging from 2 cm to 1 or more meters in cross sectional dimension, e.g., for larger formed aggregates and monolithic forms.

In some embodiments, diluents or binders used for the purpose of forming composite formed aggregates containing a heterogeneous catalyst (e.g., an OCM active catalyst) are selected from Silicon Carbide, Magnesium Oxide, Calcium Oxide, Alumina, aluminosilicates, carbonates, sulfates, low acidity refractory oxides such as cordierite (Mg$_2$Al$_4$Si$_5$O$_{18}$) and alkaline earth metal aluminates (e.g., CaAl2O4, Ca$_3$Al$_2$O$_6$). In other embodiments, the diluents are selected from one or more of the diluents described in the foregoing section entitled "Catalytic Formulations." The diluents are preferentially of low surface area and low porosity in order to minimize potential negative interaction between the diluent surface and the reaction product intermediates.

Additional binders can also be used in order to improve the mechanical strength (in particular crush strength) of the formed aggregates. In some embodiments, such binders are inorganic precursors or inorganic clusters capable of forming bridges between the particles in the aggregate, for example, colloidal oxide binders such as colloidal silica, alumina or zirconia may be used. In the particular case of an OCM catalyst however, inertness of the binder toward reaction intermediates is generally desired. Since standard colloidal silica and colloidal alumina have been found to interfere with the OCM reaction, certain embodiments include catalytic materials which do not comprise these types of binders, and in certain embodiments the catalytic materials comprise a catalytic nanowire and substantially no binder (i.e., the nanowires act as binder material). In some embodiments, the binder may comprise low concentration of CeO$_2$ provided the red-ox activity of the binder is much smaller than the overall catalyst activity for OCM of the composite form.

Apart from the above mentioned components, further components and auxiliaries are typically added to the mixture to be formed (e.g., extruded). Water and, if appropriate, acids or bases may be employed. In addition, organic and inorganic substances which contribute to improved processing during formation of the catalytic form and/or to a further increase in the mechanical strength and/or the desired porosity of the extruded catalytic material can additionally be employed as auxiliaries. Such auxiliaries can include graphite, stearic acid, methylstearate, silica gel, siloxanes, cellulose compounds, starch, polyolefins, carbohydrates (sugars), waxes, alginates, and polyethylene glycols (PEGs).

The ratios of active catalyst to binder to be used in the formed aggregate varies depending upon the desired final catalyst form, the desired catalytic activity and/or mechanical strength of the catalytic form and the identity of the catalyst. With regard to extrudates, the rheology of the paste to extrude can be varied to obtain the desired catalytic material.

In certain embodiments, the disclosed formed catalytic materials for the OCM reaction are designed differently from catalytic materials employed in common catalytic reactions involving the elementary steps of adsorption, surface reaction, and desorption. While not wishing to be bound by theory, it is believed that in certain embodiments the OCM reaction follows an Eley-Rideal mechanism where methane is activated at a catalyst surface by collision, generating methyl radicals that then react in the gas phase surrounding the catalyst surface. Under such a mechanism, the pore volume within the catalytic material can become filled with high methyl radical concentration, leading to highly selective methyl radical coupling and ethane formation.

This mechanism leads to a catalyst that can produce very high turnover rates and allows operation at higher gas hourly space velocities relative to other catalytic reactions. Since reactor vessels with high aspect ratio (length/diameter ratio for cylindrical reactor) are desirable at commercial scale, high gas linear velocity or superficial velocity is preferred in some embodiments of OCM at commercial scale. As used herein, "high linear velocity" or "OCM linear velocity" both refer to linear velocities which range from about 1 m/s to about 10 m/s, or in certain embodiments from about 2 m/s to about 8 m/s and in other embodiments from about 2 m/s to about 4 m/s. Typical commercial reactor systems used for other catalytic reactions with similar dimensions run lower space velocity and much lower linear velocities such as less than about 2 m/s or less than about 1 m/s. These high linear flow rates result in increased flow resistance for catalyst beds with small particle size and low void fraction.

Accordingly, one challenge associated with an OCM catalytic material is to minimize mass transfer limitations within the reactor (and the catalyst) to take advantage of the very rapid kinetics while meeting pressure drop requirements for a practical commercial deployment. To minimize mass transfer resistance, both external and internal mass transfer must be minimized. In certain embodiments, the internal mass transfer resistance is minimized by maintaining the catalytic material's diameter at a minimum and the pore size at greater than about 10 nm. In other embodiments, to minimize external mass transfer resistance, the hydrodynamics are controlled such that the process is operated at a gas velocity where the Reynolds number is high and the flow is turbulent. The Reynolds numbers increases with increasing particle effective diameter or gas velocity. In certain embodiments herein the OCM reaction is operated under conditions such that the Reynolds number (based on particle) exceeds 100, for example greater than 1,000 or greater than 2,000.

To meet both a small effective diameter to minimize internal mass transfer resistance and a high Reynolds number, certain embodiments of the catalytic material are chosen to have a shape that minimizes the effective diameter but have a high void fraction to reduce the pressure drop generated from high gas velocity. Thus, certain embodiments of the disclosed catalytic materials are provided in high void forms such as rings, pentagons, ovals, and the like, each having optional fluted edges and through holes.

Accordingly, in some embodiments, the catalytic materials of the invention are produced in various shapes and sizes. In this regard, extrudates or tablets find particular utility in certain embodiments. Exemplary catalytic materials include extruded or tableted cylinders, rods, stars or ribbed particles, trilobes, hollow shapes, donut or ring-shaped particles, pellets, tubed, spherical, fluted, honeycombs and irregular shapes. In various embodiments, catalyst size and shape is chosen to meet selectivity, activity, and pressure drop requirements for a particular reactor size and reactor operating conditions (e.g., temperature, pressure, linear velocity, etc.). The catalytic material size and shape may be different depending on specific reactor type. Catalyst size is typically chosen to provide the highest surface area possible (e.g., most contact with reactant gases) while maintaining an acceptably low pressure drop. Therefore, small reactors will typically use small size particles while large reactors will typically use larger size particles. In some embodiments, small extrudates or tablets have an outer diameter ranging in size from 0.5 to 10 mm, preferably from 1 to 50 mm, particularly preferably from 6 to 25 mm. In other embodiments, the mean ratio of length to outer diameter for small catalytic materials is from 0.2:1 to 20:1, preferably from 0.7:1 to 10:1, particularly preferably from 1:1 to 5:1. Exemplary embodiments of large catalytic materials include extrudates or tablets ranging in size (effective diameter) from 10 to 50 mm, preferably from 10 to 30 mm, particularly preferably from 14 to 25 mm. In certain other embodiments, the mean ratio of length to outer diameter for large catalytic materials is from 0.1:1 to 20:1, preferably from 0.7:1 to 10:1, particularly preferably from 0.5:1 to 2:1.

The shape of the catalytic materials may be selected to either increase or decrease the active catalyst volumetric loading since the shape of the form may have a significant impact on the void fraction between formed particles. For example, one embodiment is directed to donut shaped particles which have larger inter packbed void fraction because of the added void contributed by the donut hole in this form when compared to a plain cylindrical shape of the same diameter. In certain embodiments, a shape that gives acceptable pressure drop and surface area at commercial scale has a bed void fraction between about 0.6 and 0.7 and an effective diameter between about 3 and 12 mm. As used herein, effective diameter is calculated as 6*(volume)/(surface area).

Other aspects are directed to hollow catalytic forms (which are typically prepared by extrusion or casting, but may be press formed as well). Such embodiments allow separation of different gas domains by a porous and catalytically active material. One implementation of such design is in hollow tubes with walls made of nanowire catalyst with diluent material. The tubes may be used to introduce reagents in separate streams. Another implementation of such complex form can be wall flow through monoliths where feed gases and product gases are on separate sides of the catalytic walls.

In certain other aspects, tube or ring shaped catalyst particles are used. While not wishing to be bound by theory, it is believed that the wall or ring thickness can have a significant impact on performance. In particular, a larger wall or ring thickness is thought to promote lower light-off temperatures for OCM reactions. Restated, ring or tube shaped catalyst forms or particles having a higher ratio of the outer diameter to the inner diameter show lower light-off temperatures for OCM reactions. In particularly preferred aspects, the wall or ring thickness of an OCM catalyst particle, e.g., a nanowire OCM catalyst containing particle as described elsewhere herein, is selected so that the ratio of inner diameter to outer diameter is between about 0.3 and 0.7. For example, in some cases, the wall thickness of the catalyst particle may be between about 1 mm and about 10 mm, with particularly preferred catalyst particles being between about 6 mm and about 2 mm, and more preferably between about 4 mm and about 1.4 mm, with even more preferred wall thicknesses being between about 1.5 and 1.9 mm for catalyst rings or tubes that have an outer diameter of between about 1 mm and about 50 mm, preferably between about 4 mm and about 10 mm.

Figure 2A:
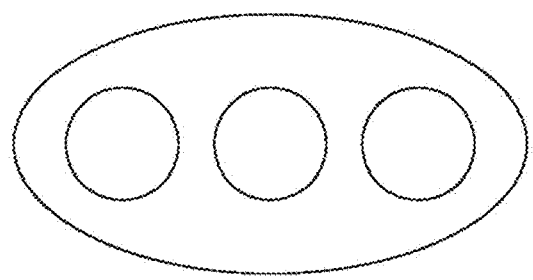
FIGS. 2A-F illustrate exemplary catalytic material shapes.

Other embodiments of ring-shaped catalytic materials include rings having an outer diameter from about 3 mm to about 50 mm. Inner diameters in certain embodiments range from about 1 mm to about 25 mm. The outer diameter can be selected to be larger than the inner diameter. Accordingly, various embodiments are directed to a catalytic material comprising a plurality of OCM active catalysts, wherein the catalytic material is in the shape of a ring (e.g., FIGS. 2D-F) having an outer diameter ranging from about 3 mm to about 50 mm and an inner diameter ranging from about 1 mm to about 25 mm, wherein the outer diameter is larger than the inner diameter. In related embodiments, the ratio of inner to outer diameter of the rings ranges from about 0.3 to about 0.9, for example from about 0.4 to about 0.8 or from about 0.65 to about 0.75. The aspect ratio of the rings (length divided by outer diameter) varies in different embodiments. In certain embodiments the aspect ratio ranges from about 0.5 to about 2, 0.5 to about 2 or from about 0.6 to about 1.2.

Different scale reactions will typically benefit from different sized rings. For example, for smaller scale reactions (e.g., pilot, small commercial, etc.), the rings will typically have an outer diameter ranging from about 3 mm to about 15 mm, from about 4 mm to about 10 mm or from about 5 to about 10 mm. In various embodiments, the inner diameter of these rings will vary from about 1 mm to about 10 mm, for example from about 2 to about 7 mm or from about 2 to about 5 mm. For example, in some embodiments the rings have an outer diameter of about 6 mm and an inner diameter of about 3 mm.

In more specific embodiments, catalytic materials in the shape of rings have an outer diameter ranging from about 5 mm to about 10 mm and an inner diameter ranging from about 1 mm to about 4 mm. In other embodiments the outer diameter ranges from about 5 mm to about 7 mm and the inner diameter rangers from about 2 mm to about 4 mm. In some related embodiments the outer diameter is about 6 mm and the inner diameter is about 3 mm.

For larger scale reactions (e.g., demonstration scale, commercial scale, etc.) may benefit from larger ring sizes. Accordingly, in some embodiments the outer diameter of the rings ranges from about 10 mm to about 50 mm for example from about 15 to about 40 mm or from about 18 mm to 25 mm. The inner diameter of the rings in such embodiments ranges from about 10 mm to about 25 mm, for example from about 10 mm to about 20 mm or from about 12 mm to about 18 mm.

In further embodiments of the above described rings, the rings have an outer diameter ranging from about 17 mm to about 19 mm and an inner diameter ranging from about 11 mm to about 13 mm. In other embodiments, the rings have an outer diameter ranging from about 18 mm to about 20 mm and an inner diameter ranging from about 12 mm to about 14 mm. In some other embodiments, the rings have an outer diameter ranging from about 19 mm to about 21 mm and an inner diameter ranging from about 13 mm to about 15 mm. In some more embodiments, the rings have an outer diameter ranging from about 21 mm to about 23 mm and an inner diameter ranging from about 14 mm to about 16 mm. In even more embodiments, the rings have an outer diameter ranging from about 21 mm to about 23 mm and an inner diameter ranging from about 15 mm to about 17 mm. In yet more embodiments, the rings have an outer diameter ranging from about 24 mm to about 26 mm and an inner diameter ranging from about 16 mm to about 18 mm. Other embodiments include rings having an outer diameter ranging from about 21 mm to about 26 mm and an inner diameter ranging from about 17 mm to about 19 mm.

In more specific embodiments of the foregoing, the rings have an outer diameter of about 18 mm and an inner diameter of about 12 mm. In other embodiments, the rings have an outer diameter of about 20 mm and an inner diameter of about 13 mm. In more embodiments, the rings have an outer diameter of about 20 mm and an inner diameter of about 14 mm. In other embodiments, the rings have an outer diameter of about 22 mm and an inner diameter of about 15 mm. In more embodiments, the rings have an outer diameter of about 22 mm and an inner diameter of about 16 mm. In more embodiments, the rings have an outer diameter of about 25 mm and an inner diameter of about 17 mm. In yet more embodiments, the rings have an outer diameter of about 25 mm and an inner diameter of about 18 mm.

In further embodiments of the above described rings, the rings have an outer diameter ranging from about 13 mm to about 15 mm and an inner diameter ranging from about 9 mm to about 11 mm. For example, in some embodiments, the rings have an outer diameter of about 14 mm and an inner diameter of about 10 mm.

In various embodiments of any of the foregoing formed catalytic materials the catalytic material has a C2+ selectivity of greater than 50% when the catalytic material is employed as a catalytic material in a method for the oxidative coupling of methane to C2+ hydrocarbons, wherein the method comprises passing a feed gas comprising methane though the catalytic material at linear velocities ranging from about 1 m/s to about 10 m/s. In other embodiments of the foregoing formed catalytic materials, the active catalyst is a nanowire catalyst.

Other exemplary shapes for catalytic materials described herein include "miniliths." Miniliths are small monolithic materials having void volumes therein. The miniliths can be provided in any number of various shapes and sizes. For example, in certain embodiments minilith shapes range from cubic to cylindrical and include non-regular shapes thereof. The void volume within the miniliths can also vary in size and shape. In some embodiments, the void volume is cylindrical. The number of void spaces in a typical minilith will also vary from about 1 to about 10 per minilith, for example from about 3 to about 7 per minilith.

With respect to size of the disclosed miniliths, various embodiments are directed to miniliths having an outside dimension ranging from about 10 mm to about 50 mm for example from about 15 to about 40 mm or from about 18 mm to 25 mm. With respect to "largest outside dimension" for a minilith, this value is determined based on the smallest diameter pipe that the minilith will fit in. For example, the largest outside dimension of a cylindrical minilith will be its diameter while for a cubic minilith this dimension will be a diagonal of one of the cubic faces.

In certain embodiments, the minliths have a non-tessellating shape. Non-tessellating shapes are advantageous in certain embodiments since the formed catalytic materials cannot tightly pack together and void spaces remains between the individual formed pieces. Accordingly, in some embodiments a formed catalytic material comprising a catalyst and a binder or diluent is provided, the catalytic material comprising:
 a) a non-tessellating shape;
 c) an effective diameter ranging from 1 mm to 20 mm; and
 d) a void fraction of greater than 0.3.

In some embodiments, the catalyst is an OCM active catalyst. In some embodiments, the effective diameter ranges from about 5 to about 50 mm, from about 15 mm to about 30 mm or from about 20 to about 28 mm.

The void fraction is optimized to result in optimal pressure drop and contact of the active catalyst with the reactant gases. In some embodiments, the void fraction ranges from about 0.4 to about 0.8, for example from about 0.5 to about 0.7 or from about 0.6 to about 0.7. In more specific embodiments, the void fraction ranges from about 0.64 to about 0.67 or from about 0.54 to about 0.58.

The density is also optimized for such factors as crush strength and porosity. For example, in certain embodiments the formed catalytic materials have a total density ranging from about 0.5 g/cm$^3$ to about 2.0 g/cm$^3$, for example from about 0.8 g/cm$^3$ to about 1.5 g/cm$^3$ or from about 0.9 g/cm$^3$ to 1.2 g/cm$^3$. As used herein, the term "total density" refers to the density of the entire formed catalytic materials (i.e., including the total volume occupied by any void volume and porosity). With respect to a catalyst bed (i.e., a plurality of formed or extruded catalytic materials) the "total density" also includes inter-catalyst void volume (void volume between individual extrudates or tablets, etc.).

Experiments performed in support of the present invention, and described in more detail in the examples, have determined that sharp (i.e., 90 degree) edges on formed catalytic materials are a source of attrition for the formed catalytic materials. Under the weight of the catalyst bed and/or during various operations, including loading the catalytic materials into the reactor, the sharp edges break down and produce fine materials. The fine materials can interfere with the process in any number of ways, including increasing the pressure drop through the catalyst bed (e.g., clogging the void volume). Based on this finding, the present inventors have arrived at formed catalytic materials which comprise rounded or chamfered edges (FIG. 1). Such catalytic materials solve the previously unrecognized problem associated with sharp-edged catalytic materials.

Further, since pressure drop across a catalytic bed is an important factor to consider, some of the formed catalytic materials comprise convex surfaces, instead of the traditional flat surfaces. The convex surfaces allow for more void volume in the packed catalyst bed (i.e., the formed catalytic materials do not pack as tightly).

Figure 2B:
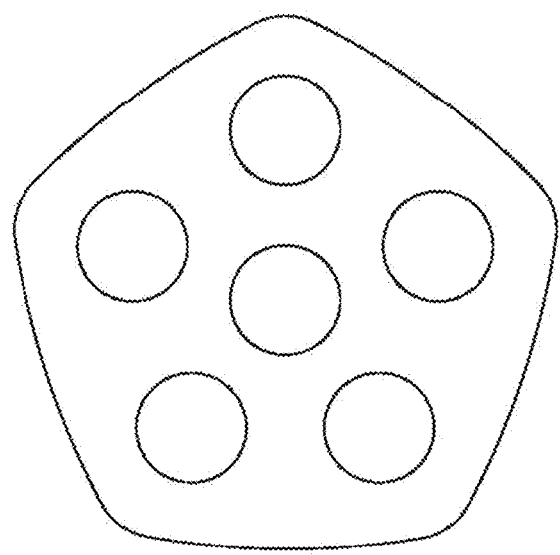

In some of the foregoing embodiments, the non-tessellating shape is a pentagon (e.g., FIG. 2B). The pentagon may be an irregular or a regular pentagon. The size of the pentagon shaped catalytic materials is typically selected based on the scale of the reaction. Larger scale reaction will typically utilize larger formed catalytic materials. In some embodiments the pentagon has an effective diameter ranging from about 5 mm to about 50 mm, for example from about 10 mm to about 30 mm or from about 20 to 30 mm. In some more specific embodiments, the effective diameter ranges from about 22 to 26 mm.

In other embodiments, the non-tessellating shape is an ellipse (e.g., FIG. 2A). Again, the size of the ellipse will generally be selected based on the scale of the desired reaction. In some embodiments, the ellipse has a major diameter ranging from about 10 mm to 30 mm and a minor diameter ranging from about 5 mm to about 20 mm. In other embodiments, the major diameter ranges from about 20 mm to about 30 mm and the minor diameter ranges from about 6 mm to about 18 mm. For example, in some more specific embodiments the major diameter ranges from about 22 mm to about 26 mm and the minor diameter ranges from about 10 mm to about 14 mm.

Figure 2C:
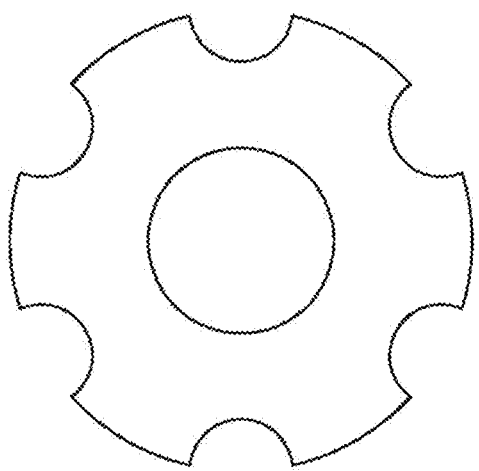
Figure 2D:
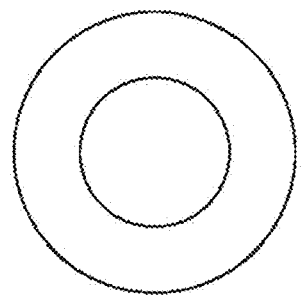
Figure 2E:
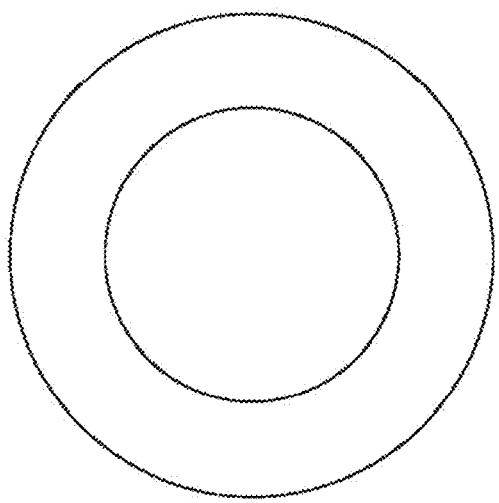
Figure 2F:
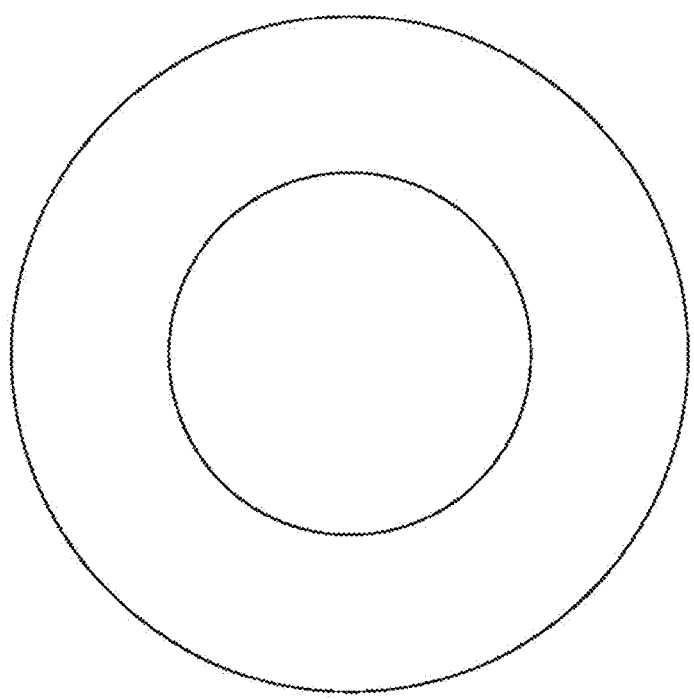

In various embodiments the void space of a catalyst bed is controlled by including grooves and/or flutes on the edges of the formed catalytic materials (e.g., FIG. 2C). The flutes are typically a convex shape (circular) cut into the outer edge of the formed catalytic materials. In some embodiments, the catalytic materials comprise one or more fluted edge. In some other embodiments, the one or more flutes have a diameter ranging from about 2 to about 10 mm, for example about 6 mm.

In any of the foregoing embodiments, the OCM catalyst comprises a rare earth oxide. In some embodiments, the catalyst is a nanowire catalyst, and in other embodiments the catalyst is a bulk catalyst.

The void volume in a minilith ranges (e.g., ring or non-tessellating shape) from about 10% to about 50% or from about 25% to about 35% of the total volume of minilith. The aspect ratio of the disclosed miniliths (length divided by outside dimension) ranges from about 0.5 to about 2 or from about 0.6 to about 1.2.

In certain embodiments, the miniliths (e.g., rings, pentagons, ellipses) comprise 3 void spaces. In other embodiments the miniliths comprise 4 void spaces. In more embodiments, the miniliths comprise 5 void spaces. In some other embodiments, the miniliths comprise 6 void spaces. In yet other embodiments, the miniliths comprise 7 void spaces. In certain embodiments, the void spaces are cylindrical.

The dimension of a void space will vary and is determined based on the largest cross-sectional dimension of the void space. The void space dimension will typically range from about 2 to about 10 mm, for example from about 3 to about 8 mm or from about 3 to about 5 mm or about 5 mm.

In various other embodiments, the miniliths comprise an outer dimension ranging from about 15 mm to about 17 mm and void space dimensions ranging from about 4 to about 6 mm. In other embodiments, the miniliths comprise an outer dimension ranging from about 17 mm to about 19 mm and void space dimensions ranging from about 4 to about 6 mm. In more embodiments, the miniliths comprise an outer dimension ranging from about 15 mm to about 17 mm and void space dimensions ranging from about 3 to about 5 mm. In other embodiments, the miniliths comprise an outer dimension ranging from about 21 mm to about 23 mm and void space dimensions ranging from about 4 to about 6 mm. In still more embodiments, the miniliths comprise an outer dimension ranging from about 17 mm to about 19 mm and void space dimensions ranging from about 3 to about 5 mm.

In yet more embodiments, the miniliths comprise an outer dimension ranging from about 19 mm to about 21 mm and void space dimensions ranging from about 3 to about 5 mm. In other embodiments, the miniliths comprise an outer dimension ranging from about 21 mm to about 23 mm and void space dimensions ranging from about 4 to about 6 mm. In more embodiments, the miniliths comprise an outer dimension ranging from about 17 mm to about 19 mm and void space dimensions ranging from about 3 to about 4 mm. In still more embodiments, the miniliths comprise an outer dimension ranging from about 19 mm to about 21 mm and void space dimensions ranging from about 4 to about 5 mm. In more embodiments, the miniliths comprise an outer dimension ranging from about 21 mm to about 23 mm and void space dimensions ranging from about 4 to about 5 mm.

In various embodiments of the foregoing, the miniliths comprise from 3 to 7 void spaces. For example, in some embodiments the miniliths comprise 3 void spaces. In other embodiments the miniliths comprise 4 void spaces. In more embodiments, the miniliths comprise 5 void spaces. In some other embodiments, the miniliths comprise 6 void spaces. In yet other embodiments, the miniliths comprise 7 void spaces. In some embodiments, the catalytic material is in the form of a straight long shape (i.e., rod or cylinder), which may be formed in a manner similar to other extrudates or cast, molded or pressed particles. In some embodiments, these catalytic materials are assembled as a stack of parallel cylinders to create an area of channels similar to the area of channels through a monolith with a larger solid to void ratio. Reducing the void ratio can be advantageous in increasing the gas linear velocity through these channels and potentially provide a better reactor volume utilization.

Other forms that have a much longer length than their other dimensions can also be used to form self-assembled monolith like structures. In some embodiments, catalytic materials in the shape of straight non-nesting helicoidal ribbons are used to form a monolith type structure with hybrid properties between a monolith and a foam (interconnected void and radial mixing, but lower pressure drop and preferential heat flux direction).

In a variant of certain embodiments of the invention, shaped catalytic materials having a defined porosity in the range of large mesopores or small macropores are used. These catalytic materials have a porosity of >10%, >30%, >40%, >50% or even >60% for pore diameters greater than 5 nm.

Active catalyst loading in the above catalytic forms ranges from 1 to 500 mg per cm$^3$ of support component, for example from 5 to 100 mg per cm$^3$ of catalytic material.

In still other embodiments, the invention provides a formed catalytic material for performing oxidative coupling of methane at linear velocities ranging from about 0.1 m/s to about 10 m/s, the catalytic material comprising:
  a) a catalyst
  b) a non-tessellating shape;
  c) a binder or diluent;
  d) a crush strength of greater than about 2 N/mm after exposure to air comprising water at temperatures between about 20° C. and 30° C. for greater than 50 hours; and
  d) a bed void fraction of greater than 0.3.

The formed catalytic material for performing OCM may have any of the shapes, sizes and other properties described above. Specific embodiments are also provided below. For example, in some embodiments, the catalytic material has an effective diameter ranging from 1 mm to 30 mm, for example, from about 15 mm to about 30 mm.

In other embodiments, the void fraction of the catalytic material ranges from about 0.5 to about 0.7 or from about 0.6 to about 0.7.

In other embodiments, the catalytic material has a density ranging from about 0.8 g/cm$^3$ to about 3.0 g/cm$^3$.

With regard to the physical shape of the foregoing catalytic material, in some embodiments the catalytic materials have at least one rounded or chamfered edge, for example all rounded or chamfered edges.

In other embodiments, the non-tessellating shape is a pentagon, for example a regular pentagon. In some embodiments, the pentagon has an effective diameter ranging from about 10 mm to about 30 mm, for example from about 20 to 30 mm or from about 22 to 26 mm.

In other embodiments, the non-tessellating shape is an ellipse. In some of these embodiments, the ellipse has a major diameter ranging from about 10 mm to 30 mm, and a minor diameter ranging from about 5 mm to about 20 mm. In other embodiments, the major diameter ranges from about 20 mm to about 30 mm, and the minor diameter ranges from about 6 mm to about 18 mm. in still more embodiments, the major diameter ranges from about 22 mm to about 26 mm, and the minor diameter ranges from about 10 mm to about 14 mm.

In some different embodiments, the catalytic materials further comprise one or more fluted edge. For example, in some embodiments the one or more flute has a diameter ranging from about 2 to about 10 mm.

In other embodiments, the catalytic material further comprises void spaces. For example, in some embodiments the void spaces are circular and have a diameter ranging from about 2 to about 10 mm.

In other embodiments of the foregoing catalytic material, the catalyst comprises a rare earth oxide. In some different embodiments, the catalyst is a nanostructured catalyst, for example a nanowire catalyst.

Other embodiments provide a formed catalytic material comprising a plurality of nanostructured catalysts (e.g., nanowires) tableted or extruded into a form, the catalytic material having a density ranging from about 2.0 g/mL to about 5.0 g/mL, a porosity ranging from about 0.7 to about 0.2 and a surface area ranging from about 30 m$^2$/g to about 0.2 m$^2$/g. In some embodiments, the formed catalytic material further comprises a crush strength ranging from about 3 N/mm to about 30 N/mm. In other embodiments, the formed catalytic material is an extrudate. In still different embodiments, the formed catalytic material is a tableted catalytic material.

Still other embodiments provide a formed catalytic material comprising an OCM active catalyst, wherein the catalytic material comprises a non-tessellating shape having a plurality of penetrating holes therethrough. In some of these embodiments, the OCM catalyst is a nanostructured catalyst, such as a nanowire.

In some embodiments of the any of the foregoing catalytic materials, the catalytic material has a C2+ selectivity of greater than 50% when the catalytic material is employed as a catalytic material in a method for the oxidative coupling of methane to C2+ hydrocarbons, wherein the method comprises passing a feed gas comprising methane through the catalytic material at linear velocities ranging from about 0.1 m/s to about 10 m/s.

In still other embodiments is provided a formed catalytic material comprising a plurality of OCM active catalysts, wherein the catalytic material has a C2+ selectivity of greater than 50% when the catalytic material is employed as a catalytic material in a method for the oxidative coupling of methane to C2+ hydrocarbons, wherein the method comprises passing a feed gas comprising methane though the catalytic material at linear velocities ranging from about 0.1 m/s to about 10 m/s. Catalytic materials useful in various embodiments are as defined herein.

In some other embodiments of the foregoing catalytic material, the linear velocity ranges from about 2 m/s to about 10 m/s, or from about 2 m/s to about 4 m/s.

In other embodiments, the C2+ selectivity is greater than about 55% or greater than about 60%.

In another embodiments, a formed catalytic material for performing oxidative coupling of methane at linear velocities ranging from about 0.1 m/s to about 10 m/s is provided, the catalytic material comprising (a) a catalyst and a binder or diluent; (b) a non-tessellating shape; and (c) at least one rounded or chamfered edge, at least one convex surface or both, wherein the catalytic material comprises a methane conversion of greater than 20% and a C2 selectivity of greater than 50% when the catalytic material is employed as a heterogeneous catalyst in the oxidative coupling of methane at a temperatures ranging from about 550° C. to about 750° C.

In some embodiments, the formed catalytic material has an effective diameter ranging from 1 mm to 30 mm.

In other embodiments, the formed catalytic material has a void fraction of greater than 0.3.

In still more embodiments, the catalytic material has a density ranging from about 0.8 g/cm$^3$ to about 3.0 g/cm$^3$.

In still other embodiments, the catalytic material has at least one rounded or chamfered edge, for example all chamfered edges.

In still more embodiments, the catalytic material has at least one convex surface, for example all convex surfaces.

In some embodiments, the non-tessellating shape is a pentagon. Or an ellipse.

In still different embodiments, the catalytic material comprises plurality of penetrating holes therein.

In other embodiments of the foregoing catalytic material, the catalyst comprise a rare earth oxide. In other embodiments, the catalyst is a nanostructured catalyst, such as a nanowire catalyst.

In other embodiments, the exotherm of the OCM reaction may be at least partially controlled by blending the active catalytic material with catalytically inert material, and forming (e.g., by pressing or extruding) the mixture into the desired shape, for example shaped pellets or extrudates as discussed above. In some embodiments, these mixed particles may then be loaded into a pack-bed reactor. The formed aggregates comprise from about 30% to 70% pore volume and from about 1% (or lower) to 99% active catalyst (by weight). In some embodiments, the formed aggregates comprise from about 5-95% active catalyst, from about 5-90% active catalyst, from about 5-75% active catalyst or from about 5-50% active catalyst. Useful inert materials in this regard include, but are not limited to those described herein above. In certain specific embodiments the inert materials are selected from SiC and cordierite.

In addition to reducing the potential for hot spots within the catalytic reactor, another advantage of using a structured ceramic with large pore volume as a catalytic support is reduced flow resistance at the same gas hourly space velocity versus a pack-bed containing the same amount of catalyst.

Nanowire shaped catalysts are particularly well suited for incorporation into formed aggregates, such as pellets or extrudates, or deposition onto structured supports, for example structured supports having a thickness ranging from about 1 to about 100 microns. Nanowire aggregates forming a mesh type structure can have good adhesion onto rough surfaces. Accordingly, various embodiments of the foregoing formed catalytic materials comprise nanowire catalyst as described herein and incorporated by reference.

The mesh like structure can also provide improved cohesion in composite ceramic improving the mechanical properties of pellets or extrudates containing the nanowire shaped catalyst particles.

Alternatively, such nanowire on support or in pellet form approaches can be used for other reactions besides OCM, such as ODH, dry methane reforming, Fischer-Tropsch, and all other catalytic reactions.

In yet another embodiment, the catalysts are packed in bands forming a layered reactor bed. Each layer is composed by either a catalyst of a particular type, morphology or size or a particular blend of catalysts. In one embodiment, the catalysts blend may have better sintering properties, i.e. lower tendency to sinter, than a material in its pure form. Better sintering resistance is expected to increase the catalyst's lifetime and improve the mechanical properties of the reactor bed.

In yet other embodiments, the disclosure provides a catalytic material comprising one or more different catalysts. The catalysts may be a nanowire as disclosed herein and a different catalyst for example a bulk catalysts. Mixtures of two or more nanowire catalysts are also contemplated. The catalytic material may comprise a catalyst, for example a nanowire catalyst, having good OCM activity and a catalyst having good activity in the ODH reaction. Either one or both of these catalysts may be nanowires as disclosed herein.

In various embodiments of any of the foregoing catalytic materials, the catalytic materials is a catalytic material comprising a plurality of OCM active catalysts, wherein the catalytic material has a C2+ selectivity of greater than 50% when the catalytic material is employed as a catalytic material in a method for the oxidative coupling of methane to C2+ hydrocarbons, wherein the method comprises passing a feed gas comprising methane though the catalytic material at linear velocities ranging from about 1 m/s to about 10 m/s. In some embodiments, the linear velocity ranges from about 2 m/s to about 10 m/s, for example from about 2 m/s to about 4 m/s. In various other embodiments of the foregoing, the C2+ selectivity is greater than about 55%, for example greater than about 60%. In still more embodiments, the catalytic material is a ring, pentagon or ellipse-shaped catalytic material as described above (e.g., a catalytic material comprising a plurality of OCM active catalysts, wherein the catalytic material is in the shape of a ring, pentagon or ellipse having an effective diameter ranging from about 3 mm to about 50 mm and an inner diameter ranging from about 1 mm to about 25 mm, wherein the outer diameter is larger than the inner diameter, and sub-embodiments thereof). In the case of pentagon and ovals, the effective inner diameter refers to the diameter of any void spaces.

Catalyst beds comprising a plurality of any of the foregoing formed catalytic materials are also provided. In some embodiments, such catalytic beds comprise an aspect ratio ranging from about 0.3 to about 1.0 and a pressure drop ranging from about 0.05 bar/m to about 0.50 bar/m for gas head space velocities of 15,000 to 30,000 hr$^{-1}$ at STP. In some embodiments, the catalyst bed comprises an aspect ratio ranging from about 0.3 to about 0.75 and a pressure drop ranging from about 0.05 bar/m to about 0.50 bar/m for gas head space velocities of 15,000 to 45,000 hr$^{-1}$ at STP.

A method for the oxidative coupling of methane is also provided, the method comprising contacting a mixture comprising methane and oxygen with the any of the foregoing catalyst beds at gas linear velocities ranging from about 0.1 m/s to about 10 m/s.

4. Physical Properties

Embodiments of the present invention are directed to catalysts in combination with diluents or binders and/or catalysts in discreet forms such as extrudates or monoliths and the like. In this regard, the physical properties of the catalyst employed for preparation of the final catalyst formulation or form can be important to impart the desired properties of the catalyst formulation or form. The physical properties of the catalyst may also contribute to improved methods for preparation of the catalyst forms and formulations.

Uniformity in formed catalyst compositions is a highly desirable characteristic. This uniformity includes uniformity as between manufactured lots of formed catalysts, uniformity as between different formed catalyst structures or particles within a given manufacturing lot, and uniformity within a particular formed catalyst particle. As will be clear, uniformity in manufacturing over time is a critical component to ensuring predictability as to catalyst performance for customers. Such uniformity is highly dependent upon having well characterized and uniform catalyst precursors.

While the processes described herein contribute to uniformity in manufacturing processes, certain embodiments are directed to improving uniformity within a given manufacturing lot, e.g., uniformity as between different formed catalyst particles and uniformity within and across an individual formed catalyst particle. In particular, it is highly desirable to provide formed catalysts having uniform compositional and structural characteristics in order to ensure optimal catalyst performance. Such optimal performance includes both uniformity in catalyst activity, e.g., providing consistent and uniform access of reactants to catalytic surfaces within formed catalyst particles, as well as providing uniform structural characteristics within individual formed catalyst particles, as well as among populations of formed catalyst particles, e.g., crush strength, porosity, size, density, thermal capacity and conductivity, and the like.

Formed catalysts are typically prepared from catalyst powders that are formulated and formed into the desired larger forms, e.g., through extrusion, pelleting, or the like. Ensuring uniformity within powdered compositions that is transferred to the formed catalyst can present a number of challenges. These challenges are further accentuated when the formed catalyst is prepared from mixed powders of two or more different powdered materials. In particular, catalyst materials are typically blended with a number of other non-catalytic materials, or differently catalytic materials, to be co-formed into a unified formed catalyst. These additional materials include binders, diluents, supports, co-catalysts, and the like.

It is generally desirable to provide a consistent and uniform structure and composition across a formed catalyst, whether that structure and formulation is prepared from a single powdered composition or a mixture of different powdered compositions. In particular, mixtures of different materials will desirably be relatively evenly and uniformly distributed throughout a given formed catalyst. Likewise, other aspects of the formed catalyst would desirably be uniform throughout the formed catalyst. For example, the relative density and porosity of the formed catalyst should be substantially uniform throughout a given catalyst particle, in order to provide efficient use of the catalytic material in the formed catalyst, to provide consistent performance of the formed catalyst, and to provide uniform performance between formed catalyst components, whether derived from the same or different manufacturing process lots.

Non-uniformity may be desirable in some embodiments by keeping the OCM reaction confined to certain regions comprising a higher concentration of active catalyst. For example, in some embodiments the active catalyst is classified to larger particles sizes and formed within a matrix of another material that acts as a support. In this approach there are "pockets" of catalyst dispersed within the formed catalyst, which minimize interaction of catalyst and support material.

Catalyst materials used in hydrocarbon processing are generally provided as powdered or particulate/granular formulations of dried materials. Examples of such formulations include simple dry powder compositions, as well as specially configured dry formulations. In certain examples, catalyst materials are specially configured as structured nanoparticle materials, and particularly as nanowire catalyst materials as described above. These catalyst materials include catalysts that are particularly useful in hydrocarbon processing, generally, and in OCM or ODH processes in particular. For ease of discussion, these dry granular or particulate catalyst materials are generally referred to herein as powders, while catalyst materials formed into larger robust forms are referred to as "formed catalysts". Although discussed with reference to the foregoing catalyst examples, it will be appreciated that a wide variety of different known and future developed catalyst compositions will benefit from the processes and compositions of the invention.

In providing formed catalysts, these catalyst powder materials are generally subjected to additional processes to form them into the ultimately desired shape, size and structure. A number of processes may be used to create the formed catalysts, including, for example, extrusion processes, aggregation processes, coating processes, and pelleting processes. In a number of these processes, the catalyst powders are combined with liquids and other components of the desired formed catalyst, in order to extrude, press or aggregate catalyst powders into formed catalysts. Despite the introduction of liquids, e.g., water or other solvents, the catalyst powders are typically processed as substantially dry mixtures, e.g., as powders or pastes, which are then further processed.

As will be appreciated, there are a number of challenges associated with ensuring uniformity of formed catalyst particles prepared from initial powdered compositions. For example, unlike fluid compositions, it is more challenging to provide homogeneous powdered compositions that will yield the uniform formed catalyst particle structure that is desired. Likewise, process elements may additionally introduce non-uniformity into a formed catalyst particle, through the formation or creation of fine particles or unintended aggregates.

Homogeneity of powders will depend upon a number of characteristics of the powder, or in the case of combined materials, powders being combined, including, for example, the relative particle size of the powder, the relative density of the different powder's component particles, as well as the surface properties of the particles within a powder. These attributes are likewise of significant consequence when combining two or more different powders into a desired homogeneous powder formulation that is to be formed into a formed catalyst particle.

In accordance with the present invention, one or more of these characteristics are selected to provide a desired level of uniformity within a finished formed catalyst. Furthermore, these characteristics may be likewise selected to afford improved manufacturing processes.

A. Particle Size

In certain aspects, the processes used to produce formed catalysts provide for powders that have relatively well defined and relatively narrow particle size distributions. In particular, the defined and narrow nature of the particle size distribution applies to both single powder compositions as well as to discrete powder compositions that are to be mixed or blended in preparing formed catalysts. Providing narrow particle size distributions within a powdered composition ensures greater homogeneity for that powdered composition, by ensuring that larger and smaller particle sizes to not become stratified within a composition or otherwise segregated based upon particle size. Likewise, by selecting optimal particle sizes along with narrow size distributions, one can improve overall processing of powders during the formulation and forming processes. For example, powdered compositions that include higher concentrations of very fine particles may be disposed to forming uncontrolled aggregates, packing, or otherwise interfering with powder flowability, making processing more difficult, and potentially impacting overall compositional uniformity.

In some embodiments, at least 50% of the particles in a given powder composition for preparation of a tableted or extruded catalytic material are within about a 20%, a 10%, a 5%, a 2% or even a 1% deviation from the average particle size of particles in the composition. In other embodiments, at least 80% of the particles in a given powder composition for preparation of a tableted or extruded catalytic material are within a 20%, a 10%, a 5%, a 2% or even a 1% deviation from the average particle size of particles in the composition. In some more embodiments, at least 90% of the particles in a given powder composition for preparation of a tableted or extruded catalytic material are within about a 20%, a 10%, a 5%, a 2% or even a 1% deviation from the average particle size of particles in the composition. In still other embodiments, at least 95% of the particles in a powder composition for preparation of a tableted or extruded catalytic material are within a 20%, 10%, a 5%, a 2% or even a 1% deviation of the average particle size of particles in the composition, for example in some cases, at least 99% of the particles are within about a 20%, 10%, a 5%, a 2% or even a 1% deviation of the average particle size of particles in the composition.

In addition to size distribution, in preferred aspects, the powdered compositions used in preparing the formed catalysts described herein will typically range from about 1 μm in average particle diameter to about 1,000 μm or to about 500 μm in average particle diameter. As will be appreciated, average diameter refers to an average cross-sectional dimension of particles, but does not require a particle that is necessarily spherical or substantially spherical.

In many cases, the parameters of particle size and particle size distribution may refer both to singular powder compositions, as well as to separate powdered compositions that are to be combined in order to produce the formed catalysts described herein. In particular, where two or more powdered compositions are to be combined into a combined powder composition to be used in producing a formed catalyst material, and those two or more powdered compositions are of approximately equivalent density, it will generally be desirable to have the above described particle size and particle size distributions apply to each of the separate powders, in order to ensure homogeneity within the final combined powder composition.

B. Flowability

In addition to providing greater homogeneity of the powdered compositions, both the particle size and size distribution are generally selected to ensure sufficient flowability of the powders for ease of handling in the forming process. In particular, by selecting particle sizes and distributions as described above, the powdered compositions used in the forming processes of the invention will generally have better flow characteristics. Improved flowability is provided, at least in part, by providing narrow size distributions around preferred particle size ranges. The particle size can be obtained in the granulation process can be controlled by varying several factors, e.g. amount of water or other liquids added to the formulation, granulation time, granulator blades speed, the particle size distribution of the components, i.e. catalysts (e.g., nanowires), dopants, diluents, binders.

In particular, by providing uniform size distributions around a selected particle size range, one can ensure more uniform flow characteristics of the flowing particles. For example, if a powdered composition includes a large population of fine particles or dust, it can present adherence points in a flow stream, in turn resulting in blockage, aggregate formation, or the like. Likewise, the presence of larger particles may lead to abrasions within a flow process, which can in turn, lead to generation of finer particulates and powders, leading to the above noted issues.

In addition to providing narrow particle size distributions and particle size ranges as described above, flowability may also be enhanced through the provision of flow enhancing materials to the particulate compositions. These flow enhancing material additives, also referred to as "lubricants" may be provided as dry, liquid or powder admixtures to the overall powder or particulate composition or they may be added into the formulation of one or more of the other powdered constituents to the overall composition, e.g., provided in the original creation and formulation of a catalyst or diluent powder.

A number of lubricants for powdered compositions can be used, and include, e.g., stearate-based moieties and polymers, specific examples of which are provided herein. In the context of the present invention, preferred lubricants will be selected so as not to negatively impact the performance, lifetime, structure, etc. of a resulting formed catalyst. In particular, such lubricants will typically be selected so as to not introduce any catalytic poisons into the finished catalyst compositions, as such material can be detrimental to catalyst performance.

C. Porosity

It is also desirable to provide formed catalysts having a uniform porosity. In particular, the porosity of the formed catalyst can directly impact the efficiency of the catalyst by providing accessibility of the reactants to the catalysts surfaces where the reaction of interest is catalyzed. Where the porosity of the formed catalyst varies, either within a single formed catalyst particle, or as between different catalyst particles, it can impact the overall efficiency of the catalyst material, e.g., by providing regions of low activity and regions of high activity, which in turn can lead to additional issues, such as thermal non-uniformity in catalyst particles or catalyst beds. Likewise, relative porosity of a catalyst particle can also directly impact its structural characteristics, e.g., crush strength, leading to catalyst particles that have relatively lower crush strength in one portion of the particle or in one particle relative to another. This difference in structural properties may again, impact catalytic processes by altering handling and processing ability, generation of fines, etc., which can again lead to additional problems.

In accordance with the present invention, formed catalytic materials having uniform porosity may generally be provided, at least in part, through the use of powdered compositions having uniform particle size distributions and/or uniform porosity used to prepare the formed catalyst.

D. Crush Strength

The crush strength is an important physical property of catalysts for commercial applications. In general, the crush strengths of the presently described catalysts and catalytic materials formed therefrom will vary from about 1 N/mm to about 30 N/mm or more as determined by ASTM D4179 for 6 mm cylinders formed at 1 ton pressure using a manual hydraulic pellet press. In other embodiments, the crush strengths of the presently described catalysts and catalytic materials formed therefrom will vary from about 1 N/mm to about 50 N/mm as determined by ASTM D4179 for 13 mm tablets formed at pressures ranging from about 2 tons to about 10 tons pressure using a manual hydraulic pellet press. In other embodiments, the crush strengths of the presently described catalysts and catalytic materials formed therefrom exceed 30 N/mm for 2 mm extrudates. Certain methods described herein result in catalytic materials (e.g., formed catalytic materials having improved crush strengths relative to other catalytic materials. For example, as described in more detail below, use of carbonate salts during the doping process allows for lower calcination temperatures and thus catalytic materials which are more stable at ambient conditions. While not wishing to be bound by theory, it is believed this stronger catalytic formed results from the absence of metal oxides (e.g., rare earth oxides) which are formed at the higher calcination temperatures, and which revert to the hydroxide at ambient temperatures.

Accordingly, in one embodiment the disclosure herein provides a catalyst comprising a base catalyst material and a dopant, wherein the catalyst has a crush strength of greater than about 2 N/mm, greater than about 6 N/mm or even greater than about 10 N/mm after exposure to air at temperatures between about 20 C and 30 C for greater than 50 hours, for example between about 50 and 100 hours.

For example, in some embodiments is provided a formed catalyst comprising a nanostructured catalyst base material and a dopant, wherein the catalyst has a crush strength of greater than about 2 N/mm after exposure to air comprising water at temperatures between about 20° C. and 30° C. for greater than 50 hours. In exemplary embodiments of the foregoing, the catalyst comprises a methane conversion of greater than 20% and a C2 selectivity of greater than 50% when the catalyst is employed as a heterogeneous catalyst in the oxidative coupling of methane at a temperatures ranging from about 550° C. to about 750° C.

In certain embodiments of the foregoing, the base catalyst comprises a rare earth oxide. In some embodiments, the rare earth oxide comprises lanthanum, cerium, praseodymium, neodymium, samarium, europium, gadolinium, terbium, dysprosium, holmium, erbium, thulium, ytterbium, lutetium or combinations thereof.

The catalyst in this regard is not limited by morphology, but in some embodiments the catalyst is a nanowire catalyst. In other embodiments, the dopant is an alkaline earth metal dopant, such as magnesium, calcium, strontium or barium.

4. Preparation

The catalysts and catalytic materials can be prepared according to any number of methods. Exemplary procedures for preparing nanowire based catalysts are provided in co-pending U.S. application Ser. No. 13/115,082 (U.S. Pub. No. 2012/0041246); Ser. No. 13/479,767 (U.S. Pub. No. 2013/0023709); Ser. No. 13/689,611 (U.S. Pub. No. 2013/0165728); Ser. No. 13/689,514 (U.S. Pub. No. 2013/0158322) and U.S. Provisional Application Nos. 61/794,486; 61/909,840; and 61/988,063. Briefly, some embodiments of nanowire catalysts can be prepared using a bacteriophage template. A phage solution is first prepared, to which metal salt precursor comprising metal ions is added. Thereafter, an anion precursor is added. Under appropriate conditions (e.g., pH, molar ratio of the phage and metal salt, molar ratio of the metal ions and anions, addition rate, etc.), the metal ions and anions become bound to the phage, nucleate and grow into a nanowire. Following calcinations, nanowires are optionally calcined to form a metal oxide. An optional step of doping incorporates a dopant in the nanowires. Template other than phage may also be employed.

Non-template directed methods for preparation of nanowire catalysts may also be employed. For example, hydrothermal or sol gel methods described in the foregoing co-pending applications may be used. Other methods, such as those described in U.S. Pub. No. 2013/0270180, the full disclosure of which is incorporated herein by reference, may also be employed. For example, a slurry of a metal isopropoxide in ethanol is first prepared and filtered. The wet cake is then treated with aqueous hydroxide at temperatures of about 230 C for 24 hours, thus resulting in nanowires.

The catalytic materials can be prepared after preparation of the individual components (i.e., catalyst, diluent, binder, support, etc.) by mixing the individual components in their dry form, e.g. blend of powders, and optionally, milling, such as ball milling, grinding, granulating, or other similar size reduction processes can be used to reduce particle size and/or increase mixing. Each component can be added together or one after the other to form layered particles. The individual components can be mixed prior to calcination, after calcination or by mixing already calcined components with uncalcined components. The catalytic materials may also be prepared by mixing the individual components in their dry form and optionally pressing them together into a "pressed pellet" or extrudate followed by calcination to above 400° C.

In other examples, the catalytic materials are prepared by mixing the individual components with one or more solvents into a suspension or slurry, and optional mixing and/or milling can be used to maximize uniformity and reduce particle size. Examples of slurry solvents useful in this context include, but are not limited to: water, alcohols, ethers, carboxylic acids, ketones, esters, amides, aldehydes, amines, alkanes, alkenes, alkynes, aromatics, etc. In other embodiments, the individual components are deposited on a supporting material such as silica, alumina, magnesia, activated carbon, and the like, or by mixing the individual components using a fluidized bed granulator. Combinations of any of the above methods may also be used.

Other methods for preparation of catalytic materials include use of a wet filter cake isolated via the method described in copending U.S. application Ser. No. 13/757,036 (U.S. Pub. No. 2013/0253248), which application is hereby incorporated by reference in its entirety for all purposes. For example, a wet filter cake (i.e., still containing some solvent and/or wash solution) can be extruded to form extrudates directly. An optional binder may be included in the wet cake prior to extrudation. Further, the wet cake may also optionally be washed with a solution containing a dopant or a solid dopant may be added to the wet cake, and the resulting wet cake can be extruded to prepare doped catalytic materials.

The solvent content of the wet cake can be controlled to control the rheology of the wet cake to obtain desirable extrudate properties.

In some embodiments, methods for preparation of extruded catalytic materials comprise predation of a solution(s) comprising the desired dopants (e.g., as a soluble salt such as nitrate or carbonate). This solution is then combined with a composition comprising the base catalyst material or a precursor thereof. For example, in some embodiments the dopant solution is combined with a metal hydroxide. This mixture is then dried in an oven to approximately 1-20% (e.g., about 2%) moisture content, and the dried composition is milled and passed through a sieve (e.g., 1.0 mm). Optional binders, diluents, lubricants, peptizing agents and/or extruding agents and DI water are added to reach the desired water content (e.g., 10-40%). This paste is then extruded in the desired shape, dried to remove water and then calcined.

In some embodiments for preparation of pressed catalysts (e.g., tablets and other shapes), the base catalyst material and optional binders, diluents, lubricants, peptizing agents and/or extruding agents are mixed and pressed into the desired form using a tablet press (e.g., Specac® hydraulic pellet press) or other similar instrument. Pressure applied during tableting typically ranges from about 1 ton to about 20 tons, for example from about 2 tons to about 10 tons. Dopants may be included in the pre-formed composition (before tableting) or incorporated via any other means.

As noted above, various processing aids may be employed for the extrusion or tableting process. For example, in some embodiments the method for preparation of pressed catalytic materials comprises forming a composition comprising the base catalyst material (which may be optionally doped before, after or during the tableting process) and a processing agent (the "pre-formed composition"). In some embodiments, the processing aid is an organic acid, water or a carbohydrate-based polymer, such as a polymer comprising methylcellulose. Combinations of these processing aids may also be used. In various embodiments, the organic acid is acetic acid. In other embodiments, the carbohydrate based polymer is methylcellulose and/or hydroxypropyl methyl cellulose. The concentration of processing aid can vary from about 0% to about 10%. For example, in some embodiments the processing aid is present in the pre-formed composition at concentration ranging from about 0% to about 5%, for example about 5%. In some more specific embodiments, the processing aid is a carboxylic acid, such as citric acid, acetic acid, succinic acid, or stearic acid, which is present at about 5% by weight of the pre-formed composition. In other embodiments, the processing aid comprises both citric acid and methylcellulose and/or hydroxypropyl methyl cellulose.

In some other embodiments, the tableting processes include use of a lubricant in the pre-formed composition. When present, the lubricant may be present in amount ranging from about 1% to about 5%, for example about 1% to about 3%. In some embodiments, the lubricant is a stearate-based moiety or a polymer. Exemplary stearate based moieties include, but are not limited to: magnesium stearate, calcium stearate, strontium stearate, methyl stearate, stearic acid and Acrawax®. In some different embodiments, the polymer is polyethylene glycol having a molecular weight of about 2,000 or about 20,000, polyvinyl alcohol having a molecular weight of about 23,000 or about 146,000 or carboxymethyl cellulose.

The particle size distribution of the base catalyst material and/or preformed composition can have an effect on the final properties, such as crush strength and density, of the tableted catalysts. In general, finer particles (such as those produced by milling) result in catalytic materials having higher density and crush strength relative to larger particles (such as those produced by oscillating granulation).

Particle size distributions can be controlled using specific size reduction operations and/or classification of the powders using mechanical separation. Size reduction operations include crushers (jaw crushers, gyratory crushers, crushing rolls), grinders (hammer mills, impactors, rolling-compression mills, attrition mills, tumbling mills), ultrafine grinders (hammer mills with classification, fluid energy mills, agitated mills), and cutting machines (knife cutters, dicers, slitters). The type of size reduction operation depends on the desired particle size. The particles can be separated and classified using sieve trays.

The catalytic materials may optionally comprise a dopant. In this respect, doping material(s) may be added during preparation of the individual components, after preparation of the individual components but before drying of the same, after the drying step but before calcinations or after calcination. Dopants may also be impregnated into, or adhered onto formed aggregates, or as layers applied upon supports for formed aggregates, prior to addition of one or more different materials, e.g., catalyst materials, diluents, binders, other dopants, etc. If more than one doping material is used, each dopant can be added together or one after the other to form layers of dopants.

Doping material(s) may also be added as dry components and optionally ball milling can be used to increase mixing. In other embodiments, doping material(s) are added as a liquid (e.g. solution, suspension, slurry, etc.) to the dry individual catalyst components or to the blended catalytic material. The amount of liquid may optionally be adjusted for optimum wetting of the catalyst, which can result in optimum coverage of catalyst particles by doping material. Mixing, grinding and/or milling can also be used to maximize doping coverage and uniform distribution. Alternatively, doping material(s) are added as a liquid (e.g. solution, suspension, slurry, etc.) to a suspension or slurry of the catalyst in a solvent. Mixing and/or milling can be used to maximize doping coverage and uniform distribution. Incorporation of dopants can also be achieved using any of the methods described elsewhere herein.

Because nitrate salts are typically soluble, dopants have previously been incorporated into catalyst base materials by contacting the catalyst base material with a solution of a metal nitrate salt (e.g., an alkaline earth metal nitrate such as strontium nitrate). Once the catalyst base material has been impregnated with the nitrate salt it is formed (e.g., into extrudate, pellet, etc.) and then calcined at temperatures of about 800° C. The calcination results in decomposition of the nitrate leading to a loss in mass, leaving voids in the catalyst form and, hence, a loss of density and strength. The calcination of nitrate containing catalysts results in a number of problems:

1. A loss of strength of the catalyst form.
2. The decomposition of nitrates is formation of NOx which must be dealt with by scrubbing, adding both complexity and cost to the catalyst manufacturing process.
3. Catalysts may be rendered highly susceptible to moisture uptake due to the formation of highly hygroscopic metal oxides. This uptake of water has the effect of significantly reducing the strength of the catalyst form. In some cases, the reduction in strength is so severe that the forms must be stored under nitrogen to prevent them from picking up atmospheric moisture, failure to do so results in the forms disintegrating in a matter of days under ambient conditions.

The present inventors have unexpectedly found that these problems may be averted if the nitrate salt is replaced with a salt that doesn't require a high temperature calcination or significant loss of mass resulting in large void formation upon calcination. This replacement precursor must also provide the excellent OCM performance achieved when nitrate salts are used as the precursor. Experiments performed in support of certain embodiments of the invention show that carbonate salts alleviate the concerns outlined in points 1-3 above and also produces a catalyst with comparable OCM performance.

Accordingly, in certain embodiments, a method for preparing a catalyst comprising a dopant is provided, the method comprising preparing a mixture comprising a catalyst base material and a carbonate, sulfate, phosphate or halide salt of the dopant, and calcining the mixture at temperatures below about 400° C. or even as low as 350° C.

In other embodiments, an alternative method for preparing a catalyst comprising a dopant is provided, the method comprising: (a) preparing a mixture comprising a nanostructured catalyst base material and a salt of the dopant, wherein the salt comprises at least 95% w/w of a carbonate salt of the dopant; and (b) calcining the mixture above about 300° C., and (c) forming the formed catalyst by tableting or extrusion, wherein the catalyst has a crush strength of greater than about 2 N/mm after exposure to air comprising water at temperatures between about 20° C. and 30° C. for greater than 50 hours.

In some embodiments, the catalyst prepared according to the foregoing methods comprises a methane conversion of greater than 20% and a C2 selectivity of greater than 50% when the catalyst is employed as a heterogeneous catalyst in the oxidative coupling of methane at a temperatures ranging from about 550° C. to about 750° C.

In some embodiments of the foregoing methods, the catalyst base material comprises a rare earth oxide or hydroxide. For example, in some embodiments the rare earth oxide comprises lanthanum, cerium, praseodymium, neodymium, samarium, europium, gadolinium, terbium, dysprosium, holmium, erbium, thulium, ytterbium, lutetium or combinations thereof.

In other embodiments, the carbonate, sulfate, phosphate or halide salt is an alkaline earth metal carbonate, sulfate, phosphate or halide. For example, in some embodiments the alkaline earth metal is magnesium, calcium, strontium or barium. In some specific embodiments, the salt is a carbonate salt, for example an alkaline earth metal carbonate salt such as calcium carbonate, strontium carbonate, barium carbonate or a combination thereof.

In various embodiments of the foregoing methods, the catalyst base material is a nanostructured catalyst, such as a nanowire.

In still other embodiments of the foregoing methods, the mixture further comprises a nitrate salt.

Different embodiments for preparation of a formed catalytic material for the oxidative coupling of methane, comprise:
 a) admixing a nanostructured catalytic base material;
 b) extruding or tableting the mixture of (a) to prepare a formed catalytic material; and
 c) calcining the formed catalytic material at temperatures ranging from about 600° C. to about 1200° C.

In some embodiments, the calcining temperature ranges from about 800° C. to about 1200° C.

In other embodiments, the nanostructured catalytic base material further comprises a porogen, for example a cellulosic fiber, an organic polymer or combinations thereof.

In some embodiments, the nanostructured catalytic base material comprises nanowires.

In some further embodiments of the foregoing, the catalytic base material is formed by: (a) admixing a nanostructured catalyst with a dopant; (b) drying the doped nanostructured catalyst of (a); (c) milling the dried nanostructured catalyst of (b); and (d) calcining the milled nanostructured catalyst of (c) at temperatures ranging from about 600° C. to about 1200° C. to produce the catalytic base material.

In different embodiments, the nanostructured catalyst is crushed into a fine powder prior to step (a).

In still other embodiments, the formed catalytic material is calcined in an atmosphere comprising at least about 1% carbon dioxide ($CO_2$), for example, in some embodiments the formed catalytic material is calcined in an atmosphere comprising at least about 5%, at least about 10%, at least about 15%, at least about 20%, at least about 25%, at least about 30%, at least about 35%, at least about 40%, at least about 45%, or at least about 50% carbon dioxide ($CO_2$).

Still other embodiments for preparation of a formed catalytic material for the oxidative coupling of methane comprise:
 a) forming a nanostructured catalytic base material by: (i) admixing a nanostructured catalyst with a dopant; (ii) drying the doped nanostructured catalyst of (i); (iii) milling the dried nanostructured catalyst of (ii); and (iv) calcining the milled nanostructured catalyst of (iii) at temperatures ranging from about 600° C. to about 1200° C. to produce the nanostructured catalytic base material;
 b) extruding or tableting the mixture of (a) to prepare a formed catalytic material; and
 c) calcining the formed catalytic material at temperatures ranging from about 600° C. to about 1200° C., for example from about 800° C. to about 1200° C. In some embodiments, the method further comprises admixing a porogen with the nanostructured catalytic base material before (b), for example the porogen may comprise a cellulosic fiber, an organic polymer or combinations thereof. In other embodiments, the nanostructured catalytic base material comprises nanowires.

In the methods described herein, an optional calcination step may follow an optional drying step at T<200° C. (typically 60-120° C.) in a regular oven or in a vacuum oven. Calcination may be performed on the individual components of the catalytic material or on the blended catalytic material. In some embodiments, calcination is performed in an oven/furnace at a temperature higher than the minimum temperature at which at least one of the components decomposes or undergoes a phase transformation and can be performed in inert atmosphere (e.g. $N_2$, Ar, He, etc.), oxidizing atmosphere (air, $O_2$, etc.) or reducing atmosphere ($H_2$, $H_2/N_2$, $H_2/Ar$, etc.). The atmosphere may be a static atmosphere or a gas flow and may be performed at ambient pressure, at p<1 atm, in vacuum or at p>1 atm. High pressure treatment (at any temperature) may also be used to induce phase transformation including amorphous to crystalline. Calcinations may also be performed using microwave heating.

Calcination is generally performed in any combination of steps comprising ramp up, dwell and ramp down. For example, ramp to 500° C., dwell at 500° C. for 5 h, ramp down to RT. Another example includes ramp to 100° C., dwell at 100° C. for 2 h, ramp to 300° C., dwell at 300° C. for 4 h, ramp to 550° C., dwell at 550° C. for 4 h, ramp down to RT. Calcination conditions (pressure, atmosphere type, etc.) can be changed during the calcination. In some embodiments, calcination is performed before preparation of the blended catalytic material (i.e., individual components are calcined), after preparation of the blended catalytic material but before doping, after doping of the individual components or blended catalytic material. Calcination may also be performed multiple times, e.g. after catalyst preparation, after aggregate formation, and/or after doping, as well as upon any or all of the individual components that are added to the formed aggregate, e.g., dopants, catalysts, diluents, supports, etc.

In some embodiments of the foregoing methods calcining is performed at temperatures below about 350° C.

The calcination conditions can have an effect on the mechanical properties of the final catalytic materials. Experiments performed in support of embodiments of the present invention having shown that the calcination hold temperature, the final calcination cool-down temperature, the calcination atmosphere and storage conditions of the calcined material can have an impact on the mechanical properties of the final catalytic materials. Accordingly, in some embodiments the catalytic materials are calcined at temperatures ranging from about 600 C to about 900 C in a substantially dry atmosphere. In some embodiments, the calcination temperature is about 650 C. After holding at the calcination temperature, the catalytic materials are cooled down and stored in a sealed container. In various embodiments, the cooled down temperature is about 250 C to 350 C, for example about 300 C. In other embodiments, the structural integrity of the catalytic materials does not substantially degrade upon storage in dew point air at around room temperature (about 20 F to 40 F) for up to 16 hours or more.

Metal oxides, particularly those used in OCM, are sensitive to water, both at room temperature and at OCM reaction conditions (500-1000° C.). At room temperature, an increased concentration of water in the atmosphere can cause rehydroxylation, promoting cracking and weakening in the formed catalyst pellets. At process conditions, having water in the atmosphere can promote sintering and densification of the catalyst tablets. This increased sintering reduces the active surface area of the catalyst, negatively impacting the activity, and also reduces the size of the catalyst, which has a negative effect on pressure drop and creates bed shrinkage and flow deviations. The catalyst shrinkage will result in volume/height changes of the catalyst bed during operation. Gas mixing at the top of the bed and autoignition can be impacted by the distance between the top of the bed and the gas mixer. Thus, it is desirable to prevent volume changes of the catalyst bed.

A typical industrial strategy for a material that sinters under reaction conditions would be to adhere this material to an inert support. However, for the OCM reaction, this strategy would also cause the coating to break down due to the high concentration of water present and the sensitivity of the material to water. Another strategy would be to minimize the concentration of water present in the OCM reactor. However, the OCM reaction creates water (at a concentration of about 8 mol %), and there is also water in the OCM feed (at a concentration of about 3 mol %) that would be impractical and costly to remove. Carbon dioxide appears to preferentially adsorb to the surface of the formed catalyst and thereby inhibit this sintering. Carbon dioxide can also stabilize carbonates and oxycarbonate phases within the catalyst, improving catalytic activity.

Accordingly, in some embodiments, the invention provides a method comprising introducing carbon dioxide into the environment surrounding an OCM catalyst in order to inhibit sintering and water uptake. The carbon dioxide can be contacted with the catalytic material at any point, for example during calcination, after calcination (e.g., during storage), in a reactor or even during the OCM reaction.

Accordingly, in some embodiments carbon dioxide is introduced into the OCM reaction mixture at the reactor inlet. Introduction of carbon dioxide in this manner improves the durability of the catalyst surface area at the front of the bed, inhibits bed shrinkage, and/or improves catalytic performance. Embodiments of this method serve to improve the lifetime of the OCM catalyst and increase the amount of time that a plant can be operated between shutting down and switching out the catalyst.

In other embodiments, the catalytic materials are aged in carbon dioxide. Aging the catalytic materials in carbon dioxide allows the catalyst to be aged at a higher temperature with less densification. This allows accelerated catalyst aging at higher temperatures without a major loss of catalyst stability, facilitating pilot-scale research.

In still other embodiments, after forming the catalyst, the catalyst is calcined in an atmosphere containing an increased concentration of carbon dioxide (e.g., about 10% carbon dioxide). As with the OCM reaction, aging the catalyst in a carbon dioxide atmosphere can reduce sintering and surface area loss. This can produce catalysts with lower light-off temperatures and higher activity. Incorporating dopants in the form of metal carbonates as discussed above, rather than metal nitrates or metal oxides, into the formed catalyst can also produce this effect to an extent.

Calcination conditions have also been found to affect the porosity, density, crush strength and/or surface area of the catalytic materials. Thus, in addition to the pressure applied during the tableting process (e.g., from about 1 to about 20 tons, about 1 to about 10 tons or about 1 to about 5 tons), the calcination temperature can be varied to control physical properties of the catalytic materials. In general, the crush strength increases, while the porosity and surface area both decrease as the calcination temperature increases. In some embodiments the calcination temperature ranges from about 600 C to about 1200 C. In other embodiments, the calcination temperature does not exceed about 800 C. Catalytic materials (e.g., tableted or pressed catalytic materials) formed under these calcination conditions generally have a crush strength ranging from about 5 N/mm to about 30 N/mm, a porosity ranging from about 0.7 to about 0.4 and/or a surface area ranging from about 30 $m^2/g$ to about 0.5 $m^2/g$.

Furthermore, in other embodiments the density and/or porosity of the catalytic materials can be controlled by varying the compression applied during tableting. For example, the density can range from about 2 g/ml to about 3 g/ml or about 5 g/ml or more by applying compression forces ranging from about 2 ton to about 10 ton during the tableting process using a manual hydraulic pellet press. The porosity can range from about 0.7 to about 0.2 or less and the surface area can range from about 25 $m^2/g$ to about 1 $m^2/g$ or less when these same ranges of compression are used. These same densities and porosities may be obtained by calcining at various temperatures, for example temperatures ranging from about 600 C to about 1200 C, for example about 800 C. Both tableting compression and calcining temperature may be varied within the above ranges to obtain the desired density, surface area and/or porosity.

In other embodiments, the porosity, density and/or surface area of the catalytic materials can be controlled, and optimized, by use of a porogen in the pre-formed composition. Specifically, certain embodiments comprise including a porogen into the composition before formation of the extrudate or pressed tablet. In this regard, a porogen is a material which is removed upon heating, typically during the calcination process. Exemplary porogens include organic material, such as organic polymers and cellulose, which decompose upon heating at high temperatures. Upon decomposing the porogen, the catalytic materials comprise increased porosity since pores are formed in the volume formerly occupied by the porogen.

Accordingly, in some embodiments the methods for preparation of the catalytic materials include preparing a composition comprising the base catalyst material and at least one porogen; forming a catalytic material by extrusion or pressing (e.g., tableting); and calcining the catalytic material at temperatures above the decomposition temperature of the porogen. In some embodiments, the base catalyst material comprises nanowires. In some embodiments, the calcination temperature is at or exceeds 800 C. For example, about 600 C to about 1200 C or about 800 C to about 1200 C. The higher calcination temperature increase the crush strength of the formed catalytic material (e.g., because of sintering of the components), but because of the presence of the porogen the porosity is increased relative to other catalytic materials calcined at similar temperatures.

The catalytic materials may be incorporated into a reactor bed for performing any number of catalytic reactions (e.g., OCM, ODH and the like). Accordingly, in one embodiment the present disclosure provides a catalytic material as disclosed herein in contact with a reactor and/or in a reactor bed. For example, the reactor may be for performing an OCM reaction (i.e., an OCM reactor), may be a fixed bed reactor and may have a diameter greater than 1 inch. In this regard, the catalytic material may be packed neat (without diluents) or diluted with an inert material (e.g., sand, silica, alumina, etc.) The catalyst components may be packed uniformly forming a homogeneous reactor bed.

The particle size of the individual components within a catalytic material may also alter the catalytic activity, and other properties, of the same. Accordingly, in one embodiment, the catalyst is milled to a target average particle size and may be optionally sieved to select a particular particle size range. In some aspects, the catalyst powder is further processed into extrudates or pellets and the extrudates or pellets are optionally milled and/or sieved to obtain the desired particle size distribution.

In some embodiments, the catalyst materials, alone or with binders and/or diluents, can be configured into larger aggregate forms, such as pellets, extrudates, or other aggregations of catalyst particles. Such larger aggregate forms may optionally include a binder and/or support material; however, the present inventors have surprisingly found that certain nanowire catalysts are particularly suited to use in the form of a pellet without a binder and/or support material. Accordingly, one embodiment of the disclosure provides a catalytic material in the absence of a binder. In this regard, the morphology of certain catalytic nanowires (either bent or straight, etc.) is believed to contribute to the nanowires' ability to be pressed into extrudates without the need for a binder. Catalytic materials without binders are simpler, less complex and may be cheaper than corresponding materials with binders and thus offer certain advantages such as the ability to load the catalyst in pack-beds with a low pressure drop under operating conditions.

In some instances, catalytic materials may be prepared using a binder or support to maintain the catalyst formulation as a cohesive structure. A variety of materials may be employed as a binder. For example, in some embodiments catalytic materials in the form of extrudates comprising catalytic nanowires can be prepared without the use of a separate binder. In other words, because of their unique properties, nanowire materials, including the nanowire catalysts described elsewhere herein, can function to provide the requisite structural cohesion of a binder material. Certain bulk catalysts are also useful in this regard.

In some cases, a sacrificial binder (also referred to herein as a porogen) may be used. A sacrificial binder can be used in order to create unique microporosity in formed aggregates (e.g., pellets or extrudates). After removing the sacrificial binder, the structural integrity of the catalyst is ensured by the special binding properties of the catalyst (e.g., nanowires). For example, in some embodiments a catalytic material may be prepared with a binder and then the binder removed by any number of techniques (e.g., combustion, calcinations, acid erosion, etc.). This method allows for design and preparation of catalytic materials having unique microporosity (i.e., the microporosity is a function of size, etc. of the sacrificial binder). The ability to prepare different form aggregates (e.g., pellets) of catalysts, such as nanowires, without the use of a binder is not only useful for preparation of catalytic materials from nanowires, but also allows the nanowires to be used as support materials (or both catalytic and support material). Sacrificial binders and techniques useful in this regard include sacrificial cellulosic fibers or other organic polymers that can be easily removed by calcination. In some embodiments, sacrificial binders are added to increase macro-porosity (pores larger than 20 nm diameter) of the catalytic materials. Accordingly, in some embodiments the catalytic materials comprise pores greater than 20 nm in diameter, greater than 50 nm in diameter, greater than 75 nm in diameter, greater than 100 nm in diameter or greater than 150 nm in diameter.

The methods described herein for preparation of various catalytic forms may optionally include use of processing aids such as lubricants, binders, peptizing agents and/or extrusion aids.

The catalytic forms in the form of formed aggregates can be obtained, for example, by kneading or pan-milling of the starting compounds with the binder, for example any of the binders described herein, forming (e.g., extruding, casting, molding and the like) and subsequently calcining. The binder can be pretreated prior to extrusion. This is preferably carried out by means of acid, for example formic acid or nitric acid. Other auxiliaries, for example pore formers such as carboxymethylcellulose, potato starch or stearic acid, can be additionally added prior to or during extrusion.

Generally, the role of the peptizing agent is to enable the formation of a stable colloidal solution/suspension by charging the surface of the particles, thus providing repulsive force. Accordingly, in some embodiments a peptizing agent is included in a suspension/solution of a catalyst (e.g., nanowires) and/or dopant to form a more uniform paste or a paste with the desirable rheology for preparing an extruded catalytic material. The peptizing agent used for preparation of the catalytic materials may also affect the strength of the final material (e.g., higher crush strengths). Exemplary peptizing agents include salts, such as sodium chloride and the like, and acids, such as nitric acid, acetic acid, citric acid, hydrochloric acid and the like.

Other processes for preparing catalytic forms include drying a composite wet "cake" obtained by filtration or centrifugation before fragmenting such dry cake into mm size pieces, e.g., through grinding, milling or the like. The composite wet cake generally comprises the active catalyst and a binder and/or diluents/carrier material. Casting of a catalyst containing paste is also be used to create complex forms prior to drying and calcination. The catalytic materials may also be isolated and/or doped according to the procedures described in co-pending U.S. application Ser. No. 13/757,036 (U.S. Pub. No. 2013/02532), which application is hereby incorporated by reference in its entirety for all purposes.

In another embodiment, formed aggregates are prepared by sequential addition of the components of the final catalytic form. In this case forming or pelletizing the diluent or carrier component with inactive binders as needed is performed first. The inactive form is then calcined at elevated temperature to provide a mechanically strong object. The active catalyst is then contacted with the form. In certain embodiments, soluble salt precursors of the catalyst are used in this step with a high surface area carrier (or diluent or support) to promote the formation of dispersed catalyst on the support.

In embodiments wherein the catalyst is a nanowire, the catalyst is typically synthesized separately through controlled precipitation or crystallization, and in some further embodiments the support does not need to have a high surface area. However, if a homogeneous distribution of the catalytic solids is to be obtained, large pores within the form are needed to enable diffusion of the nanowire shape solid into the form. Pores on the order a few microns (e.g., about 1-10, or 1-100 microns) are desirable in this case. Dispersed nanowire suspensions in a liquid that easily wets the diluent (or carrier) are used to deposit the active component into the pores of the pre-calcined form. For example, the nanowire catalyst is coated on the inactive form by conventional methods such as dip-coating, spray-coating, and related methods. In certain embodiments, nanowire or nano-colloids may be advantageous compared to traditional bulk catalyst in this post impregnation process by enabling the addition of a large amount of catalyst by impregnation iteration onto a form with micron size pores.

In other embodiments, catalytic materials comprising nanowire catalysts can also be formed within a porous form by adding the selected form to the nanowire synthesis solution.

In yet other embodiments, separate calcinations of the catalytic material can be used at different stage of the synthesis. In this manner, strong bonds between carrier grains and/or carrier grains and binder can be formed in a first calcination step without degrading the active catalyst component.

In other examples, wet impregnation of the form containing an active catalyst (e.g., OCM catalyst) component can also be used to further promote activity or selectivity of the formed material. For example, in some embodiments the catalyst form is impregnated with a soluble salt comprising a dopant, thus producing a doped catalytic material. Methods for impregnating or coating a dopant on or in a catalytic form include dip-coating or immersion coating, and/or spray coating as described above. In certain embodiments, a low surface area carrier (or diluent) is used and most of the surface area within the catalytic form comes from the active catalyst itself. This high surface area ratio between catalytic and non-catalytic components within the form favors interaction between the active catalyst component and the doping element added to the form.

After shaping, the formed aggregates are typically dried and if appropriate calcined. The usual calcination temperatures for the catalytic materials are from 300 to 1000° C., from 400 to 800 C, from 500 to 700° C. or from 550 to 650° C., at calcination times of from 5 minutes to 5 hours, for example from 10 minutes to 5 hours or about 4 hours.

Deposition of the catalyst on a support, such as a monolith, can be performed by wash-coating which is contacting a slurry containing the catalyst with the monolith walls and removing the excess slurry prior to drying and calcination of the monolith.

Deposition of the catalyst on supports can also be performed by growing the nanowire within the monolith channel by immersing the monolith into the solution used to grow the catalyst (e.g., nanowires). In this case the wire mesh is likely to be filling all the volume of the channel with low density mesh prior to drying. During drying the gel can contract leaving mostly open channels or dry without pulling the solid mesh toward the walls (depending on surface tension of liquid and adhesion to the walls) leaving an inorganic aerogel in the channel.

In some other embodiments, the catalytic material is in the form of a monolith and the active catalyst comprises a nanowire. In such embodiments, the monoliths may be prepared from a nanowire containing composite mixture by extrusion or casting.

For ease of illustration, the above description of catalytic materials often refers to OCM; however, such catalytic materials find utility in other catalytic reactions including but not limited to: oxidative dehydrogenation (ODH) of alkanes to their corresponding alkenes, selective oxidation of alkanes and alkenes and alkynes, oxidation of CO, dry reforming of methane, selective oxidation of aromatics, Fischer-Tropsch, combustion of hydrocarbons, etc. as discussed in more detail below.

One skilled in the art will recognize that various combinations or alternatives of the above methods are possible, and such variations are also included within the scope of the present disclosure.

Catalytic Reactions and Methods

The present disclosure provides for the use of the disclosed catalytic materials in catalytic reactions and related methods. In some embodiments, the catalytic reaction is any of the reactions described herein. The morphology and composition of the catalysts in the catalytic materials is not limited. For example the catalysts may be a nanowire having a bent morphology or a straight morphology and may have any molecular composition or the catalyst may be a bulk catalyst, or any combination thereof.

The disclosed catalytic materials may be useful in any number of reactions catalyzed by a heterogeneous catalyst. Examples of reactions wherein the disclosed catalytic materials may be employed are disclosed in in co-pending U.S. application Ser. No. 13/115,082 (U.S. Pub. No. 2012/0041246); Ser. No. 13/479,767 (U.S. Pub. No. 2013/0023709); Ser. No. 13/689,611 (U.S. Pub. No. 2013/0165728); Ser. No. 13/689,514 (U.S. Pub. No. 2013/0158322) and U.S. Provisional Application Nos. 61/794,486; 61/909,840; and 61/988,063, and in Farrauto and Bartholomew, "Fundamentals of Industrial Catalytic Processes" Blackie Academic and Professional, first edition, 1997, which is hereby incorporated in its entirety. Non-limiting examples of reactions wherein the disclosed catalytic materials may be employed include: the oxidative coupling of methane (OCM) to ethane and ethylene; oxidative dehydrogenation (ODH) of alkanes to the corresponding alkenes, for example oxidative dehydrogenation of ethane or propane to ethylene or propylene, respectively; selective oxidation of alkanes, alkenes, and alkynes; oxidation of CO, dry reforming of methane, selective oxidation of aromatics;

Fischer-Tropsch, hydrocarbon cracking; combustion of hydrocarbons and the like. Some of the reactions catalyzed by the disclosed catalytic materials are discussed in more detail below.

The disclosed catalytic materials are generally useful in methods for converting a first carbon-containing compound (e.g., a hydrocarbon, CO or $CO_2$) to a second carbon-containing compound. In some embodiments the methods comprise contacting a catalytic material disclosed herein with a gas comprising a first carbon-containing compound and an oxidant to produce a carbon-containing compound. In some embodiments, the first carbon-containing compound is a hydrocarbon, CO, $CO_2$, methane, ethane, propane, hexane, cyclohexane, octane or combinations thereof. In other embodiments, the second carbon-containing compound is a hydrocarbon, CO, $CO_2$, ethane, ethylene, propane, propylene, hexane, hexene, cyclohexane, cyclohexene, bicyclohexane, octane, octene or hexadecane. In some embodiments, the oxidant is oxygen, ozone, nitrous oxide, nitric oxide, carbon dioxide, water or combinations thereof.

In other embodiments of the foregoing, the method for conversion of a first carbon-containing compound to a second carbon-containing compound is performed at a temperature below 100° C., below 200° C., below 300° C., below 400° C., below 500° C., below 550° C., below 600° C., below 700° C., below 800° C., below 900° C. or below 1000° C. In other embodiments, the method for conversion of a first carbon-containing compound to a second carbon-containing compound is performed at a pressure above 0.5 ATM, above 1 ATM, above 2 ATM, above 5 ATM, above 10 ATM, above 25 ATM or above 50 ATM.

In certain embodiments of the foregoing method, the catalytic materials comprise a catalytic nanowire. In other embodiments, the catalytic materials comprise a bulk catalyst.

The catalytic reactions described herein can be performed using standard laboratory equipment, for example as described in U.S. Pat. No. 6,350,716, which is incorporated herein by reference in its entirety.

Many catalyzed chemical transformations involve triphase reactions with a liquid, a gas and a solid heterogeneous catalyst. These reactions typically operate at moderate temperatures. Experiments performed in support of various embodiments of the invention show that molten salt can be used as a liquid media to enable increased temperature operation for triphase catalyzed reaction. The liquid carrier or solvent also has benefits for thermal management of the heat generated or removed by the reaction by allowing fast heat transport in or out of the reactor. These embodiments, also allow for introduction of feed gases at lower temperatures.

Accordingly, in various embodiments, the invention is directed to a method for performing a catalytic reaction, the method comprising contacting a composition comprising a molten salt and a catalyst with a reactant gas, thereby converting the reactant gas to a product gas. In some embodiments, the catalytic reaction is any of the reactions described herein or known in the art. In other embodiments, the reaction is a partial oxidation of a hydrocarbon. In more specific examples, the reaction is oxidative coupling of methane or oxidative dehydrogenation of ethane.

In different embodiments of the foregoing method, the catalyst is suspended in the molten salt.

In some different embodiments of the foregoing molten salt method, the catalyst comprises a transition metal oxide or a rare earth oxide. In some embodiments the rare earth oxide is a lanthanide oxide. In other embodiments, the rare earth oxide is an actinide oxide. In still other embodiments, the rare earth oxide is a scandium or yttrium oxide.

In some embodiments the catalyst is a bulk catalyst. In other embodiments, the catalyst is a nanostructured catalyst, such as a nanowire. In some even more embodiments, the catalyst is any one of the catalyst disclosed herein or in U.S. application Ser. No. 13/115,082 (U.S. Pub. No. 2012/0041246); Ser. No. 13/479,767 (U.S. Pub. No. 2013/0023709); Ser. No. 13/689,611 (U.S. Pub. No. 2013/0165728); Ser. No. 13/689,514 (U.S. Pub. No. 2013/0158322) and U.S. Provisional Application Nos. 61/794,486; 61/909,840; and 61/988,063, the disclosures of which are hereby incorporated by reference in their entireties. Advantageously, the present inventors have discovered that nanostructured (e.g., nanowire) catalysts remain suspended, and substantially evenly dispersed, in the molten salt, even in the absence of stirring.

In some different embodiments of the foregoing, the reactant gas is methane and the product gas comprises a C2 hydrocarbon. In some other different embodiments, the reactant gas is ethane and the product gas comprises ethylene.

The molten salt may also serve as a co-catalyst in the reaction. In these embodiments, the molten salt serves as an intermediate carrier of oxidative or reducing potential (is redox reactive). In these embodiments, it is also possible to feed reactant gas and oxidant gas separately (since the salt carries some of the oxidative potential). Accordingly, in some embodiments the method further comprises contacting the composition with the reactant gas in a first zone of a reactor, and contacting the composition with an oxidant gas in a second zone of the reactor In certain embodiments the molten salt comprises an oxygen-containing anion. In other embodiments, the molten salt comprises an alkali metal cation. In still more embodiments, the molten salt comprises nitrates or nitrites of sodium or potassium, or combinations thereof. In other embodiments, the anion is a sulfate or phosphate. In some other embodiments, the molten salt is redox active with respect to the catalyst.

In some different embodiments, the molten salt composition is maintained at temperatures ranging from about 400 C to About 700 C. In some other embodiments, the reactant gas is added to the composition at an inlet temperature ranging from about 20 C to about 500 C.

Compositions comprising a molten salt and a catalyst suspended therein are also provided. For example, the catalyst may be any of the catalyst described herein or incorporated by reference. In some embodiments, the catalyst comprises a transition metal oxide or a lanthanide oxide. In other embodiments, the catalyst is a bulk catalyst. In different embodiments, the catalyst is a nanostructured catalyst, such as a nanowire.

1. Oxidative Coupling of Methane (OCM)

The present disclosure provides catalytic materials for improving the yield, selectivity and/or conversion of any number of catalyzed reactions, including the OCM reaction. Reactors useful in practice of the OCM methods described herein are described in U.S. application Ser. No. 13/900,898, which application is hereby incorporated by reference in its entirety. As mentioned above, there exists a tremendous need for catalyst technology capable of addressing the conversion of methane into high value chemicals (e.g., ethylene and products prepared therefrom) using a direct route that does not go through syngas. Accomplishing this task will dramatically impact and redefine a non-petroleum based pathway for feedstock manufacturing and liquid fuel production yielding reductions in GHG emissions, as well as providing new fuel sources.

Ethylene has the largest carbon footprint compared to all industrial chemical products in part due to the large total volume consumed into a wide range of downstream important industrial products including plastics, surfactants and pharmaceuticals. In 2008, worldwide ethylene production exceeded 120 M metric tons while growing at a robust rate of 4% per year. The United States represents the largest single producer at 28% of the world capacity. Ethylene is primarily manufactured from high temperature cracking of naphtha (e.g., oil) or ethane that is separated from natural gas. The true measurement of the carbon footprint can be difficult as it depends on factors such as the feedstock and the allocation as several products are made and separated during the same process. However, some general estimates can be made based on published data.

Cracking consumes a significant portion (about 65%) of the total energy used in ethylene production and the remainder is for separations using low temperature distillation and compression. The total tons of $CO_2$ emission per ton of ethylene are estimated at between 0.9 to 1.2 from ethane cracking and 1 to 2 from naphtha cracking. Roughly, 60% of ethylene produced is from naphtha, 35% from ethane and 5% from others sources (Ren, T.; Patel, M. *Res. Conserv. Recycl.* 53:513, 2009). Therefore, based on median averages, an estimated amount of $CO_2$ emissions from the cracking process is 114M tons per year (based on 120M tons produced). Separations would then account for an additional 61M tons $CO_2$ per year.

The disclosed catalytic materials provide an alternative to the need for the energy intensive cracking step. Additionally, because of the high selectivity of the catalytic materials, downstream separations are dramatically simplified, as compared to cracking which yields a wide range of hydrocarbon products. The reaction is also exothermic so it can proceed via an autothermal process mechanism. Overall, it is estimated that up to a potential 75% reduction in $CO_2$ emission compared to conventional methods could be achieved. This would equate to a reduction of one billion tons of $CO_2$ over a ten-year period and would save over 1M barrels of oil per day.

The catalytic materials also permit converting ethylene into liquid fuels such as gasoline or diesel, given ethylene's high reactivity and numerous publications demonstrating high yield reactions, in the lab setting, from ethylene to gasoline and diesel. On a life cycle basis from well to wheel, recent analysis of methane to liquid (MTL) using F-T process derived gasoline and diesel fuels has shown an emission profile approximately 20% greater to that of petroleum based production (based on a worst case scenario) (Jaramillo, P., Griffin, M., Matthews, S., *Env. Sci. Tech* 42:7559, 2008). In the model, the $CO_2$ contribution from plant energy was a dominating factor at 60%. Thus, replacement of the cracking and F-T process would be expected to provide a notable reduction in net emissions, and could be produced at lower $CO_2$ emissions than petroleum based production.

Furthermore, a considerable portion of natural gas is found in regions that are remote from markets or pipelines. Most of this gas is flared, re-circulated back into oil reservoirs, or vented given its low economic value. The World Bank estimates flaring adds 400M metric tons of $CO_2$ to the atmosphere each year as well as contributing to methane emissions. The nanowires of this disclosure also provide economic and environmental incentive to stop flaring. Also, the conversion of methane to fuel has several environmental advantages over petroleum-derived fuel. Natural gas is the cleanest of all fossil fuels, and it does not contain a number of impurities such as mercury and other heavy metals found in oil. Additionally, contaminants including sulfur are also easily separated from the initial natural gas stream. The resulting fuels burn much cleaner with no measurable toxic pollutants and provide lower emissions than conventional diesel and gasoline in use today.

In view of its wide range of applications, the catalytic materials of this disclosure can be used to not only selectively activate alkanes, but also to activate other classes of inert unreactive bonds, such as C—F, C—Cl or C—O bonds. This has importance, for example, in the destruction of man-made environmental toxins such as CFCs, PCBs, dioxins and other pollutants. Accordingly, while the invention is described in greater detail below in the context of the OCM reaction and other the other reactions described herein, the catalytic materials are not in any way limited to these particular reactions.

The selective, catalytic oxidative coupling of methane to ethylene (i.e. the OCM reaction) is shown by the following reaction (1):

$$2CH_4 + O_2 \rightarrow CH_2CH_2 + 2H_2O \tag{1}$$

Figure 3:
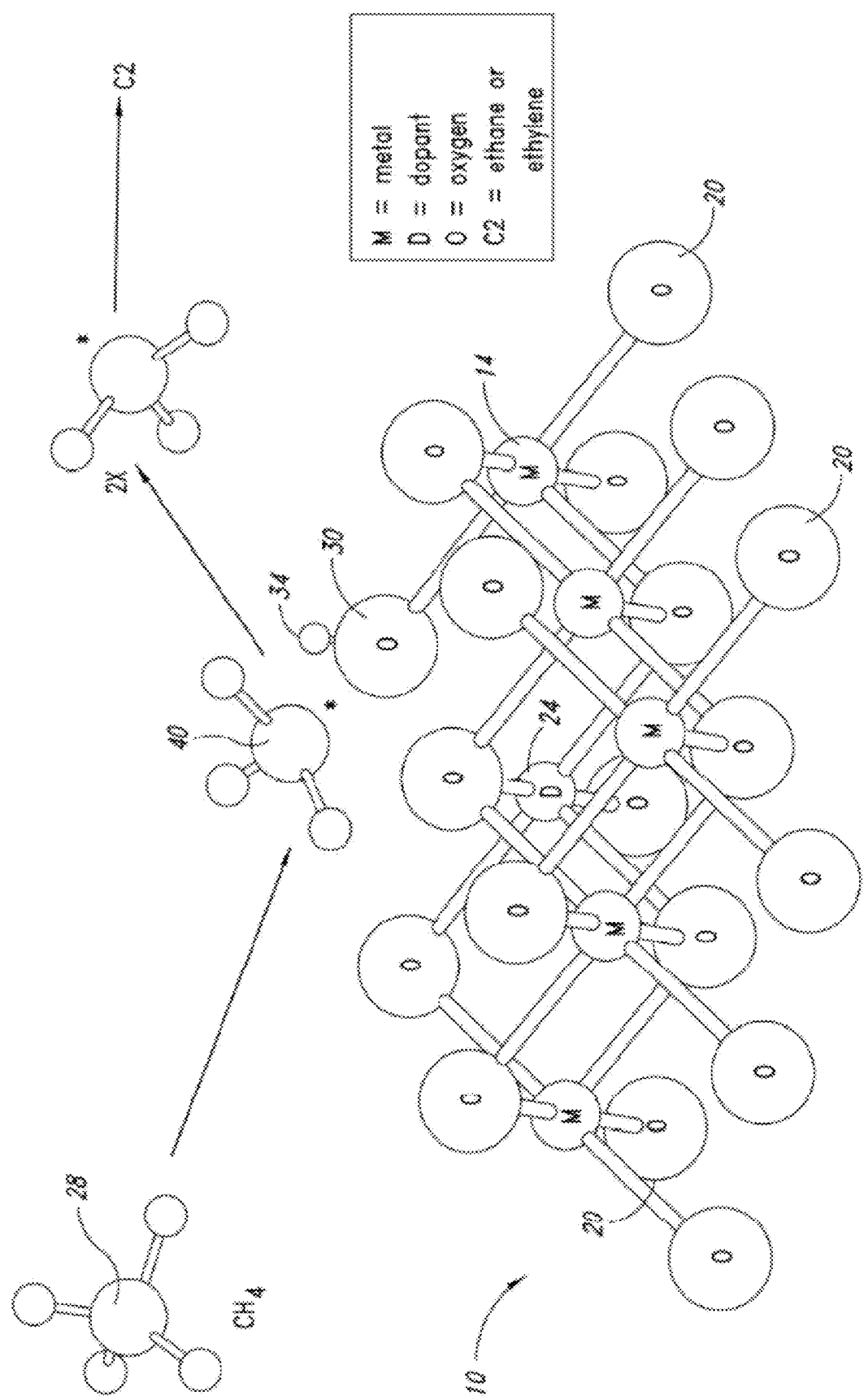
FIG. 3 schematically depicts the oxidative coupling of methane (OCM) reaction.

The OCM reaction on the surface of a heterogeneous catalyst is schematically depicted in FIG. 3. This reaction is exothermic (Heat of Reaction −67 kcals/mole) and usually occurs at very high temperatures (>700° C.). During this reaction, it is believed that the methane ($CH_4$) is first oxidatively coupled into ethane ($C_2H_6$), and subsequently the ethane ($C_2H_6$) is oxidatively dehydrogenated into ethylene ($C_2H_4$). Because of the high temperatures used in the reaction, it has been suggested that the ethane is produced mainly by the coupling in the gas phase of the surface-generated methyl ($CH_3$) radicals. Reactive metal oxides (oxygen type ions) are apparently required for the activation of $CH_4$ to produce the $CH_3$ radicals. The yield of $C_2H_4$ and $C_2H_6$ is limited by further reactions in the gas phase and to some extent on the catalyst surface. A few of the possible reactions that occur during the oxidation of methane are shown below as reactions (2) through (8):

$$CH_4 \rightarrow CH_3 \text{ radical} \tag{2}$$

$$CH_3 \text{ radical} \rightarrow C_2H_6 \tag{3}$$

$$CH_3 \text{ radical} + 2.5\ O_2 \rightarrow CO_2 + 1.5\ H_2O \tag{4}$$

$$C_2H_6 \rightarrow C_2H_4 + H_2 \tag{5}$$

$$C_2H_6 + 0.5\ O_2 \rightarrow C_2H_4 + H_2O \tag{6}$$

$$C_2H_4 + 3\ O_2 \rightarrow 2CO_2 + 2H_2O \tag{7}$$

$$CH_3 \text{ radical} + C_xH_y + O_2 \rightarrow \text{Higher HC's-Oxidation/}$$
$$CO_2 + H_2O \tag{8}$$

With conventional heterogeneous catalysts and reactor systems, the reported performance is generally limited to <25% $CH_4$ conversion at <80% combined C2+ selectivity, with the performance characteristics of high selectivity at low conversion, or the low selectivity at high conversion. In contrast, the catalytic materials of this disclosure are highly active and can optionally operate at a much lower temperature. In one embodiment, the catalytic materials disclosed herein enable efficient conversion (i.e., high yield, conversion, and/or selectivity) of methane to ethylene at temperatures of less than 900° C., less than 800° C., less than 700°

C., less than 600° C., less than 550° C., or less than 500° C. In other embodiments, the use of staged oxygen addition, designed heat management, rapid quench and/or advanced separations may also be employed.

Accordingly, one embodiment of the present disclosure is a method for the preparation of ethane and/or ethylene, the method comprising converting methane to ethane and/or ethylene in the presence of a catalytic material as disclosed herein. In certain embodiments of the foregoing method, the catalytic materials comprise a catalytic nanowire. In other embodiments, the catalytic materials comprise a bulk catalyst.

The exothermic heats of reaction (free energy) follow the order of reactions depicted above and, because of the proximity of the active sites, will mechanistically favor ethylene formation while minimizing complete oxidation reactions that form CO and $CO_2$. Representative catalyst compositions useful for the OCM reaction include, but are not limited to: highly basic oxides selected from the early members of the Lanthanide oxide series; Group 1 or 2 ions supported on basic oxides, such as Li/MgO, Ba/MgO and $Sr/La_2O_3$; and single or mixed transition metal oxides, such as $VO_x$ and Re/Ru that may also contain Group 1 ions. Other compositions useful for the OCM reaction comprise any of the compositions disclosed herein, for example MgO, $La_2O_3$, $Na_2WO_4$, $Mn_2O_3$, $Mn_3O_4$, $Mg_6MnO_8$, $Zr_2Mo_2O_8$, $NaMnO_4$, $Mn_2O_3/Na_2WO_4$, $Mn_3O_4/Na_2WO_4$ or $Na/MnO_4/MgO$, $Mn/WO_4$, $Nd_2O_3$, $Sm_2O_3$, $Eu_2O_3$ or combinations thereof. Specific examples of OCM catalysts, including nanowire catalysts are described in co-pending U.S. application Ser. No. 13/115,082 (U.S. Pub. No. 2012/0041246); Ser. No. 13/479,767 (U.S. Pub. No. 2013/0023709); Ser. No. 13/689,611 (U.S. Pub. No. 2013/0165728); Ser. No. 13/689,514 (U.S. Pub. No. 2013/0158322) and U.S. Provisional Application Nos. 61/794,486; 61/909,840; and 61/988,063. Activating promoters (i.e., dopants), such as chlorides, nitrates and sulfates, or any of the dopants described above may also be employed.

Important performance parameters used to measure the catalytic materials' performance in the OCM reaction are selected from single pass methane conversion percentage (i.e., the percent of methane converted on a single pass over the catalyst or catalytic bed, etc.), reaction inlet gas temperature, reaction operating temperature, total reaction pressure, methane partial pressure, gas-hour space velocity (GHSV), $O_2$ source, catalyst stability and ethylene to ethane ratio.

Typical temperatures for operating an OCM reaction according to the present disclosure are 800° C. or lower, 750° C. or lower, 700° C. or lower, 650° C. or lower, 600° C. or lower and 550° C. or lower. As used herein, the operation temperatures presented typically refer to the temperature immediately adjacent to the reactor inlet. As will be appreciated, with no integrated temperature control system, the exothermic nature of the OCM reaction can result in a temperature gradient across the reactor indicative of the progress of the reaction, where the inlet temperature can range from about 400° C. to about 600° C., while the outlet temperature ranges from about 700° C. to about 900° C. Typically, such temperature gradients can range from about 100° C. to about 500° C. By staging adiabatic reactors, with interstage cooling systems, one can step through a more complete catalytic reaction without generating extreme temperatures, e.g., in excess of 900° C.

In certain embodiments, the inlet gas temperature in an OCM reaction catalyzed by the disclosed catalytic materials is <700° C., <675° C., <650° C., <625° C., <600° C., <593° C., <580° C., <570° C., <560° C., <550° C., <540° C., <530° C., <520° C., <510° C., <500° C., <490° C., <480° C. or even <470° C. In certain embodiments, the reaction operating temperature (i.e., outlet temperature) in an OCM reaction catalyzed by the disclosed catalytic materials is <950° C., <925° C., <900° C., <875° C., <850° C., <825° C., <800° C., <775° C., <750° C., <725° C., <700° C., <675° C., <650° C., <625° C., <600° C., <593° C., <580° C., <570° C., <560° C., <550° C., <540° C., <530° C., <520° C., <510° C., <500° C., <490° C., <480° C., <470° C.

The single pass methane conversion in an OCM reaction catalyzed by the catalytic materials is generally >5%, >10%, >15%, >20%, >25%, >30%, >35%, >40%, >45%, >50%, >55%, >60%, >65%, >70%, >75% or even >80%.

In certain embodiments, the inlet reaction pressure in an OCM reaction catalyzed by the catalytic materials is >1 atm, >1.1 atm, >1.2 atm, >1.3 atm, >1.4 atm, >1.5 atm, >1.6 atm, >1.7 atm, >1.8 atm, >1.9 atm, >2 atm, >2.1 atm, >2.1 atm, >2.2 atm, >2.3 atm, >2.4 atm, >2.5 atm, >2.6 atm, >2.7 atm, >2.8 atm, >2.9 atm, >3.0 atm, >3.5 atm, >4.0 atm, >4.5 atm, >5.0 atm, >5.5 atm, >6.0 atm, >6.5 atm, >7.0 atm, >7.5 atm, >8.0 atm, >8.5 atm, >9.0 atm, >10.0 atm, >11.0 atm, >12.0 atm, >13.0 atm, >14.0 atm, >15.0 atm, >16.0 atm, >17.0 atm, >18.0 atm, >19.0 atm or >20.0 atm.

In some embodiments, the methane partial pressure in an OCM reaction catalyzed by the catalytic materials is >0.3 atm, >0.4 atm, >0.5 atm, >0.6 atm, >0.7 atm, >0.8 atm, >0.9 atm, >1 atm, >1.1 atm, >1.2 atm, >1.3 atm, >1.4 atm, >1.5 atm, >1.6 atm, >1.7 atm, >1.8 atm, >1.9 atm, >2.0 atm, >2.1 atm, >2.2 atm, >2.3 atm, >2.4 atm, >2.5 atm, >2.6 atm, >2.7 atm, >2.8 atm, >2.9 atm, >3.0 atm, >3.5 atm, >4.0 atm, >4.5 atm, >5.0 atm, >5.5 atm, >6.0 atm, >6.5 atm, >7.0 atm, >7.5 atm, >8.0 atm, >8.5 atm, >9.0 atm, >10.0 atm, >11.0 atm, >12.0 atm, >13.0 atm, >14.0 atm, >15.0 atm, >16.0 atm, >17.0 atm, >18.0 atm, >19.0 atm or >20.0 atm.

In some embodiments, the GSHV in an OCM reaction catalyzed by the catalytic materials is >5,000/hr, >10,000/hr, >15,000/hr, >20,000/hr, >50,000/hr, >75,000/hr, >100,000/hr, >120,000/hr, >130,000/hr, >150,000/hr, >200,000/hr, >250,000/hr, >300,000/hr, >350,000/hr, >400,000/hr, >450,000/hr, >500,000/hr, >750,000/hr, >1,000,000/hr, >2,000,000/hr, >3,000,000/hr, >4,000,000/hr.

The present inventors have discovered that OCM reactions catalyzed by the disclosed catalytic materials can be performed (and still maintain high C2 yield, C2+ selectivity, conversion, etc.) using $O_2$ sources other than pure $O_2$. For example, in some embodiments the $O_2$ source in an OCM reaction catalyzed by the disclosed catalytic materials is air, oxygen enriched air, pure oxygen, oxygen diluted with nitrogen (or another inert gas) or oxygen diluted with $CO_2$. In certain embodiments, the $O_2$ source is $O_2$ diluted by >99%, >98%, >97%, >96%, >95%, >94%, >93%, >92%, >91%, >90%, >85%, >80%, >75%, >70%, >65%, >60%, >55%, >50%, >45%, >40%, >35%, >30%, >20%, >15%, >10%, >9%, >8%, >7%, >6%, >5%, >4%, >3%, >2% or >1% with $CO_2$ or an inert gas, for example nitrogen.

The disclosed catalytic materials are also very stable under conditions required to perform any number of catalytic reactions, for example the OCM reaction. The stability of the catalytic materials is defined as the length of time a catalyst will maintain its catalytic performance without a significant decrease in performance (e.g., a decrease >20%, >15%, >10%, >5%, or greater than 1% in C2 yield, C2+ selectivity or conversion, etc.). In some embodiments, the catalytic materials have stability under conditions required for the OCM reaction of >1 hr, >5 hrs, >10 hrs, >20 hrs, >50 hrs, >80 hrs, >90 hrs, >100 hrs, >150 hrs, >200 hrs, >250 hrs, >300 hrs, >350 hrs, >400 hrs, >450 hrs, >500 hrs, >550 hrs, >600 hrs, >650 hrs, >700 hrs, >750 hrs, >800 hrs, >850 hrs, >900 hrs, >950 hrs, >1,000 hrs, >2,000 hrs, >3,000 hrs, >4,000 hrs, >5,000 hrs, >6,000 hrs, >7,000 hrs, >8,000 hrs, >9,000 hrs, >10,000 hrs, >11,000 hrs, >12,000 hrs, >13,000 hrs, >14,000 hrs, >15,000 hrs, >16,000 hrs, >17,000 hrs, >18,000 hrs, >19,000 hrs, >20,000 hrs, >1 yrs, >2 yrs, >3 yrs, >4 yrs or >5 yrs.

In some embodiments, the ratio of ethylene to ethane in an OCM reaction catalyzed by the catalytic materials is >0.3, >0.4, >0.5, >0.6, >0.7, >0.8, >0.9, >1, >1.1, >1.2, >1.3, >1.4, >1.5, >1.6, >1.7, >1.8, >1.9, >2.0, >2.1, >2.2, >2.3, >2.4, >2.5, >2.6, >2.7, >2.8, >2.9, >3.0, >3.5, >4.0, >4.5, >5.0, >5.5, >6.0, >6.5, >7.0, >7.5, >8.0, >8.5, >9.0, >9.5, >10.0.

In other embodiments, the conversion of methane in an OCM reaction catalyzed by the catalytic materials is greater than 5%, greater than 10%, greater than 20%, greater than 30%, greater than 50%, greater than 75%, or greater than 90%. In other embodiments, the conversion of methane to ethylene in an OCM reaction catalyzed by the catalytic materials is greater than 5%, greater than 10%, greater than 20%, greater than 30%, greater than 50%, greater than 75%, or greater than 90%. In some other embodiments the yield of ethylene in an OCM reaction catalyzed by the catalytic materials is greater than 10%, greater than 20%, greater than 30%, greater than 50%, greater than 75%, or greater than 90%. In some other embodiments the C2 yield in an OCM reaction catalyzed by the catalytic materials is greater than 5%, greater than 10%, greater than 20%, greater than 30%, greater than 50%, greater than 75%, or greater than 90%.

In some other embodiments, a method for converting methane into ethane and/or ethylene comprising use of catalytic material comprising two or more catalysts is provided. For example, the catalyst mixture may be a mixture of a catalyst having good OCM activity and a catalyst having good ODH activity. Such catalyst mixtures are described in more detail above.

Typically, the OCM reaction is run in a mixture of oxygen and nitrogen or other inert gas. Such gasses are expensive and increase the overall production costs associated with preparation of ethylene or ethane from methane. However, the present inventors have now discovered that such expensive gases are not required and high yield, conversion, selectivity, etc. can be obtained when air is used as the gas mixture instead of pre-packaged and purified sources of oxygen and other gases. Accordingly, in one embodiment the disclosure provides a method for performing the OCM reaction in air by contacting the disclosed catalytic materials with methane and air.

In various embodiments of the foregoing methods for the oxidative coupling of methane, a method for the oxidative coupling of methane to C2+ hydrocarbons under adiabatic conditions is provided, the method comprising passing a feed gas comprising methane at a linear velocity of 1 m/s or higher through a packed catalyst bed, the packed catalyst bed comprising any of the catalytic materials described herein. In some of these embodiments, the catalytic material is in the shape of a ring having an outer diameter ranging from about 3 mm to about 50 mm and an inner diameter ranging from about 1 mm to about 25 mm, wherein the outer diameter is larger than the inner diameter.

In any of the embodiments described herein, the linear velocity in an OCM method ranges from about 0.1 m/s to about 10 m/s, for example about 1 m/s to about 10 m/s or about 1 to about 5 m/s. In some embodiments, the linear velocity ranges from about 2 m/s to about 10 m/s, for examples from about 2 m/s to about 4 m/s.

In other embodiments, a C2+ selectivity for the conversion of methane to C2+ hydrocarbons is greater than about 50%, for example greater than about 55% or even greater than about 60%. In even other embodiments, the catalytic material employed in such methods is a ring-shaped catalytic material as described herein (e.g., a catalytic material comprising a plurality of OCM active catalysts, wherein the catalytic material is in the shape of a ring having an outer diameter ranging from about 3 mm to about 50 mm and an inner diameter ranging from about 1 mm to about 25 mm, wherein the outer diameter is larger than the inner diameter, and sub-embodiments thereof.

Methods for conducting OCM in the presence of catalyst blends comprising at least a first catalyst which is an OCM active catalyst and at least a second catalyst which is selective for oxidation of carbon monoxide are also provided. Such catalyst blends are described in more detail above. In some embodiments the method for oxidative coupling of methane comprises:

a) contacting methane and oxygen with the foregoing catalyst blend at temperatures ranging from about 525° C. to about 825° C. to form a product gas comprising C2's, carbon dioxide and substantially no carbon monoxide.

In certain embodiments, the ratio of carbon monoxide in the product gas relative to the concentration of carbon dioxide in the product gas ranges from about 0.1 to 10 to about 0.2 to 1.0.

In other embodiments, the method further comprises converting the carbon dioxide into methane. For example the carbon dioxide may be converted into methane via a methanation reaction.

In other embodiments, the method for OCM comprises:

a) contacting methane and oxygen with an OCM active catalyst to form a product gas; and b) contacting the product gas in a downstream reactor with a second catalyst that has activity for oxidation of carbon monoxide. In some specific embodiments the second catalyst the second catalyst is an oxide of a transition metal. For example, in some embodiments the transition metal is titanium, chromium, manganese, iron, cobalt, nickel, copper, zinc, zirconium, molybdenum, palladium, silver, tungsten, platinum, gold, or any combination thereof.

In other embodiments, the invention is directed to an OCM process comprising two stages. While not wishing to be bound by theory, it is believed that conducting the OCM reaction in two stages can result in a higher methane conversion, and thus higher yield of desired products (e.g., ethane and/or ethylene). For example, in some embodiments the method comprises use of an OCM process unit process comprising a two-stage adiabatic, catalytic, axial fixed bed reactor. In exemplary processes oxygen and methane, from natural gas and a downstream supplement from a methanation reactor, are pre-heated to achieve the OCM reactor inlet temperature of about 400 C to 600 C (e.g., about 450-550 C) and from 6 bar to 20 bar (e.g., about 8-12 bar). It is then fed to the first stage of the OCM reactor to undergo OCM conversion to ethylene. Catalysts useful for this first stage include, but are not limited to, any of the catalysts or catalytic materials describe herein, including those incorporated by reference. In some embodiments, the mixed feed flows over the OCM catalytic bed, and leaves the first stage at a temperature of approximately from 800 C to 900 C (e.g., about 850° C.). The reaction heat generated in the $1^{st}$ stage is typically recovered in a steam generator by generating high pressure steam. In various embodiments, the effluent from the first stage is then again mixed with oxygen and fed to the $2^{nd}$ stage of the OCM reactor at temperatures ranging from about 450 C to about 700 C (e.g., about 450-550 C) and pressures ranging from about 4 bar to about 8 bar (e.g., about 6 bar). The lower pressure in the second stage results from pressure drop generated in first stage of the OCM reactor. Further embodiments comprise a postbed-cracking step of the hot OCM effluent after the second stage and separations.

Figure 8:
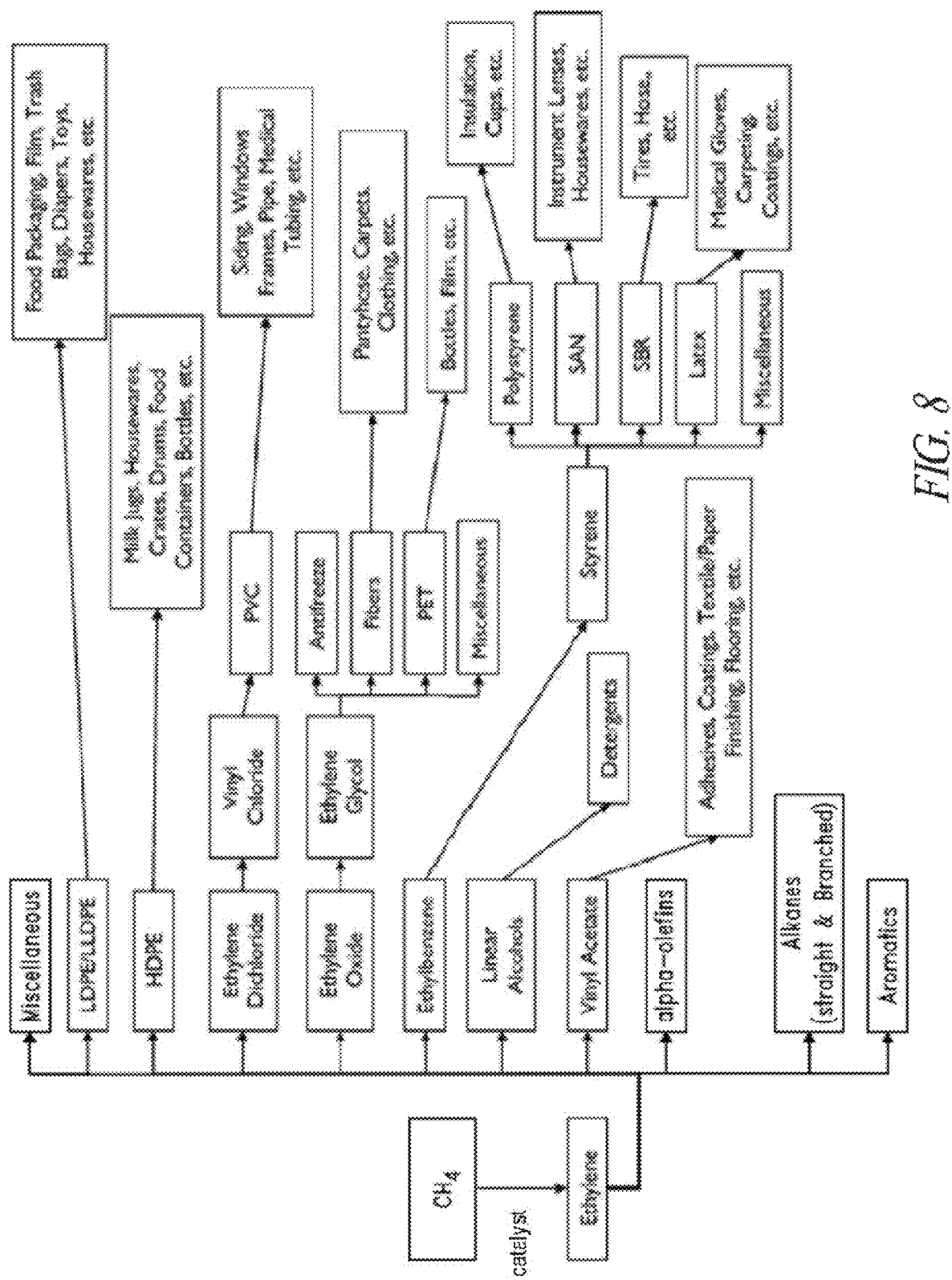
FIG. 8 shows representative downstream products of ethylene.

In some embodiments of the foregoing, the method produces ethylene which is employed as starting material to make downstream products of ethylene, for example one or more of the products illustrated in FIG. 8. In other embodiments of the foregoing method, the final product is polymer-grade ethylene product (greater than 99 wt % ethylene, e.g. 99.96 wt % or greater).

A challenge in the OCM process can be the reactivity of methane relative to its products. The products ethane and ethylene may undergo efficient partial or full oxidation, which may or may not be catalytic. At high temperature and pressure, both homogeneous and heterogeneous reactions may occur during oxidative coupling of methane, and some undesired side products may be produced in the gas phase. Accordingly, some embodiments of the present invention include catalysts, catalyst forms and catalytic materials which perform optimally even with a higher concentration of ethylene and ethane in the feed stream (a second stage catalyst, catalyst form or catalytic material), and which for example may be used in the above described two-stage process.

For second stage catalyst screening purposes, the product composition of a typical first OCM stage was simulated by employing a gas mix ("first stage gas mix") based on the gas composition resulting from a typical OCM reaction performed with an OCM catalyst as described or incorporated by reference herein with air as the oxidant. Typical first stage gas mixes comprise various concentrations of one or more of: hydrogen; nitrogen; methane; CO; $CO_2$; ethylene; ethane; and propylene. Water is a by-product of the OCM process, and may be added accordingly.

Several hundred catalyst formulations were tested as second stage catalysts first in an isothermal reactor (primary screening second stage), followed by testing of selected catalysts in a more adiabatic bench top reactor (secondary screening second stage). A simplified methodology was developed that allowed to draw correlations between the isothermal high through put bench top reactor and larger scaled more adiabatic reactors. With this methodology it was possible to predict performance ranking in between the different reactor types; even though gas phase chemistry—significant in OCM—may be different in both different reactor types.

Based on the above studies, the present inventors have identified OCM catalysts useful in the second stage of a two-stage OCM process (referred to herein collectively as "second stage OCM catalysts) which result in an overall performance of about 40%-60% overall selectivity at 10%-30% overall conversion (over both: the hypothetical first stage of optimal performance and a measured second stage). In some embodiments, the second stage OCM catalyst is the same as the catalyst used for the first stage (e.g., any of the OCM catalysts described herein and as described in co-pending U.S. application Ser. No. 13/115,082 (U.S. Pub. No. 2012/0041246); Ser. No. 13/479,767 (U.S. Pub. No. 2013/0023709); Ser. No. 13/689,611 (U.S. Pub. No. 2013/0165728); Ser. No. 13/689,514 (U.S. Pub. No. 2013/0158322) and U.S. Provisional Application Nos. 61/794,486; 61/909,840; and 61/988,063, the full disclosures of which are hereby incorporated by reference in their entirety for their disclosure of catalysts, and methods for use of the same, disclosed therein. In some other embodiments, the second stage catalyst is different than the catalyst used for the first stage and it comprises any OCM catalyst described herein and in co-pending U.S. application Ser. No. 13/115,082 (U.S. Pub. No. 2012/0041246); Ser. No. 13/479,767 (U.S. Pub. No. 2013/0023709); Ser. No. 13/689,611 (U.S. Pub. No. 2013/0165728); Ser. No. 13/689,514 (U.S. Pub. No. 2013/0158322) and U.S. Provisional Application Nos. 61/794,486; 61/909,840; and 61/988,063.

In other embodiments, the second stage OCM catalyst comprises NaMnW supported in $SiO_2$. Catalysts of this type generally have an extremely high light-off temperature (>800 C), but due to its unique set-up the light-off temperature in a second reactor according to the above two-stage method can be higher than in a one-stage process, this making this catalyst an attractive choice for the novel two-stage method. In various embodiments, the $SiO_2$ support is fully or partially replaced with $Al_2O_3$ and/or $TiO_2$ support. In particular embodiments, the NaMnW catalyst comprises a support comprising $SiO_2$ and $TiO_2$. While not wishing to be bound by theory, it is believed that the presence of such controlled impurities in the $SiO_2$ support stabilizes the OCM-active cristobalite phase of $SiO_2$. The presence of alkali in NaMnW—$SiO_2$ is believed to inhibit the gas phase oxidation of ethylene. In other embodiments, similar effects were observed when comparing pure perovskite catalysts and perovskite catalysts treated with $Na_2CO_3$ in the second stage, where the treatment with the alkali carbonate resulted in a better second stage performance.

In still other embodiments, the second stage OCM catalyst comprises a perovskite compound or perovskite-like oxide, for example as described herein. In some embodiments, the perovskite or perovskite-like oxide comprises the following formula:

$$ABO_3$$

wherein:

A is an element from the lanthanides or group 2, 3, 4, 6 or 13;

B is a metal; and

O is an oxygen anion that bonds.

The perovskite or perovskite-like oxide optionally contain additional elements (e.g., dopants). In some embodiments, the perovskite or perovskite-like oxide comprise a metal from group 4 and an element from group 2. For example, in some embodiments the metal from group 4 is Ti, Zr or Hf and the element from group 2 is Ba, Sr or Ca, for example Sr.

In some embodiments, the perovskite or perovskite-like oxide comprise a metal from group 13 and an element from group 2. For example, in some embodiments the metal from group 13 is Al and the element from group 2 is Ba, Sr or Ca, for example Sr.

In some embodiments, the perovskite or perovskite-like oxide comprise a metal from the lanthanides and an element from group 2. For example, in some embodiments the metal from the lanthanides is Ce, Sm or Tb and the element from group 2 is Ba, Sr or Ca, for example Sr. In some embodiments, the lanthanide is Sm and the element from group 2 is Ca. In other embodiments, the element from the lanthanides is Ce or Tb and the element from group 2 is Sr or Ba.

In some embodiments, the perovskite or perovskite-like oxide comprise a metal from the lanthanides and an element from group 13. For example, in some embodiments the metal from the lanthanides is Pr and the element from group 13 is Ga.

In certain other embodiments, the perovskite or perovskite-like oxide is $BaZrO_3$, $SrZrO_3$, $SrAlO_3$, $SrCeO_3$, $SrHfO_3$, $CaHfO_3$, $SrTbO_3$ or $BaTiO_3$.

In certain embodiments, the perovskite or perovskite-like oxide is doped with a dopant from any one of groups 2, 3 or the lanthanides. For example, in some embodiments the dopant is selected from Sr, Y, La, Nd, Ca, Mg, Ce and combinations thereof. In certain embodiments, the perovskite or perovskite-like oxide is doped with a dopant from group 2, for example Sr, Mg, Ca or combinations thereof. In other embodiments the perovskite or perovskite-like oxide is doped with an element from group 3, for example Y. In yet other embodiments the perovskite or perovskite-like oxide is doped with an element from the lanthanides, for example La, Nd, Ce or combinations thereof.

In still different embodiments, the second stage OCM catalyst is a mixed perovskite having the following formula:

$$A^1_\alpha A^2_\beta A^3_\chi B^1_x B^2_y B^3_z O_3$$

wherein:
$A^1$, $A^2$ and $A^3$ are each independently an element from the lanthanides or group 2, 3, 4, 6 or 13;
$B^1$, $B^2$ and $B^3$ are each independently a metal;
O is an oxygen anion;
$\alpha$, $\beta$ and $\chi$ are each independently numbers ranging from 0 to 1, wherein the sum of $\alpha$, $\beta$ and $\chi$ does not exceed 1; and
x, y and z are each independently numbers ranging from 0 to 1, wherein the sum of x, y and z does not exceed 1.

In some embodiments, the sum of $\alpha$, $\beta$ and $\chi$ is 1. In other embodiments, the sum of x, y and z is 1.

In still different embodiments, the second stage OCM catalyst is a mixed perovskite having the following formula:

$$A^1_{(1-\lambda)} A^2_\lambda B^1_{(1-\delta)} B^2_\delta O_3$$

wherein:
$A^1$ and $A^2$ are each independently an element from the lanthanides or group 2, 3, 4, 6 or 13;
$B^1$ and $B^2$ are each independently a metal;
O is an oxygen anion; and
$\delta$ and $\lambda$ are each independently numbers ranging from 0 to 1.

In some embodiments, $\delta$ and $\lambda$ are each independently numbers ranging from greater than 0 to less than 1.

The mixed perovskites can optionally contain dopants selected from metal and non-metal elements, for example lanthanide and/or alkaline earth metal dopants. In some embodiments, $A^1$ and $A^2$ are each independently an alkaline earth metal, for example Ca or Sr. In other embodiments, $B^1$ and $B^2$ are each independently a group 3 or group 4 element, for example Y or Zr.

In some embodiments, the perovskite or perovskite-like catalyst comprises Er/Ca/$BaZrO_3$, Nd/Ca/$BaZrO_3$, Eu/Ca/$BaZrO_3$, $Ca_{(1-\lambda)}Sr_\lambda Y_{(1-\delta)}Zr_\delta O_3$, $Sr_\lambda Y_{(1-\delta)}Zr_\delta O_3$, Ca/Nd/$Ca_{(1-\lambda)}Sr_\lambda Y_{(1-\delta)}Zr_\delta O_3$, Ca/Nd/$SrY_{(1-\delta)}Zr_\delta O_3$, Ca/$Nd_2O_3$/$Ca_{(1-\lambda)}Sr_\lambda Y_{(1-\delta)}Zr_\delta O_3$, $La_{0.9}Sr_{0.1}Ga_{0.8}Mg_{0.2}O_3$, $BaCe_{0.7}Y_{0.2}Pr_{0.1}O_3$, Ca/$BaZrO_3$, $BaZrO_3$, Ca/Sr/$BaZrO_3$, $SrCeO_3$, $Sr_\lambda Y_{(1-\delta)}Zr_\delta O_3$, $SrZrO_3$, $SrHfO_3$, Mg/$SrHfO_3$, $CaHfO_3$, $SrTbO_3$, $BaTiO_3$, Y/$SrZrO_3$, Ce/$GaPrO_3$, $SrCeO_3$/$SrCe_2O_4$, $Ce_{0.5}La_{0.4}Sr_{0.1}O_3$, $BaCeO_3$, $BaY_xCe_yO_3$, $BaY_xZr_yCe_zO_3$, $BaY_xLn_yCe_zO_3$, $BaZr_wY_xLn_yCe_zO_3$, wherein $\delta$, $\lambda$, w, x, y and z are numbers ranging from greater than 0 to 1, and Ln is a lanthanide element such as Gd or Nd. In some embodiments the sum of x and y is 1, or the sum of x, y and z is 1, or the sum of w, x, y and z is 1. Other perovskite compounds are useful in various different embodiments.

2. Oxidative Dehydrogenation

Worldwide demand for alkenes, especially ethylene and propylene, is high. The main sources for alkenes include steam cracking, fluid-catalytic-cracking and catalytic dehydrogenation. The current industrial processes for producing alkenes, including ethylene and propylene, suffer from some of the same disadvantages described above for the OCM reaction. Accordingly, a process for the preparation of alkenes, which is more energy efficient and has higher yield, selectivity, and conversion than current processes is needed. Applicants have now found that the presently disclosed catalytic materials fulfill this need and provide related advantages.

In one embodiment, the catalytic materials are useful for catalyzing the oxidative dehydrogenation (ODH) of hydrocarbons (e.g. alkanes and alkenes). For example, in one embodiment the catalytic materials are useful for catalysis of an ODH reaction for the conversion of ethane or propane to ethylene or propylene, respectively. Reaction scheme (9) depicts the oxidative dehydrogenation of hydrocarbons:

$$C_xH_y + \tfrac{1}{2}O_2 \rightarrow C_xH_{y-2} + H_2O \qquad (9)$$

Representative catalysts useful for the ODH reaction include, but are not limited to catalysts (e.g., nanowires) comprising Zr, V, Mo, Ba, Nd, Ce, Ti, Mg, Nb, La, Sr, Sm, Cr, W, Y or Ca or oxides or combinations thereof. Activating promoters (i.e. dopants) comprising P, K, Ca, Ni, Cr, Nb, Mg, Au, Zn, or Mo, or combinations thereof, may also be employed.

In some embodiments, the conversion of hydrocarbon to alkene in an ODH reaction catalyzed by the catalytic materials is greater than 10%, greater than 20%, greater than 30%, greater than 50%, greater than 75%, or greater than 90%. In some other embodiments the yield of alkene in an ODH reaction catalyzed by the catalytic materials is greater than 10%, greater than 20%, greater than 30%, greater than 50%, greater than 75%, or greater than 90%. In other embodiments, the selectivity for alkenes in an ODH reaction catalyzed by the catalytic materials is greater than 50%, greater than 60%, greater than 70%, greater than 80%, greater than 90%, or greater than 95%. In another embodiment, the catalytic materials disclosed herein enable efficient conversion (i.e. high yield, conversion, and/or selectivity) of hydrocarbon to alkene at temperatures of less than 800° C., less than 700° C., less than 600° C., less than 500° C., less than 400° C., or less than 300° C.

The stability of the catalytic materials is defined as the length of time the catalytic materials will maintain its catalytic performance without a significant decrease in performance (e.g., a decrease >20%, >15%, >10%, >5%, or greater than 1% in ODH activity or alkene selectivity, etc.). In some embodiments, the catalytic materials have stability under conditions required for the ODH reaction of >1 hr, >5 hrs, >10 hrs, >20 hrs, >50 hrs, >80 hrs, >90 hrs, >100 hrs, >150 hrs, >200 hrs, >250 hrs, >300 hrs, >350 hrs, >400 hrs, >450 hrs, >500 hrs, >550 hrs, >600 hrs, >650 hrs, >700 hrs, >750 hrs, >800 hrs, >850 hrs, >900 hrs, >950 hrs, >1,000 hrs, >2,000 hrs, >3,000 hrs, >4,000 hrs, >5,000 hrs, >6,000 hrs, >7,000 hrs, >8,000 hrs, >9,000 hrs, >10,000 hrs, >11,000 hrs, >12,000 hrs, >13,000 hrs, >14,000 hrs, >15,000 hrs, >16,000 hrs, >17,000 hrs, >18,000 hrs, >19,000 hrs, >20,000 hrs, >1 yrs, >2 yrs, >3 yrs, >4 yrs or >5 yrs.

Oxidative coupling of methane into ethane/ethylene is generally understood to comprise a number of elementary reactions taking place in series or in parallel. While not wishing to be bound by theory, a close look at the OCM mechanism suggests that auto-thermal cracking of the ethane produced during the OCM reaction may contribute to the formation of olefins from the higher alkanes produced through OCM. The importance of this mechanism has been verified for the OCM process fed by relatively dry natural gas (i.e. with limited amount of high hydrocarbons in the natural gas), but processing very wet natural gas (above 5% higher hydrocarbon content) with an OCM fixed bed reactor is problematic as preferential combustion of C2+ hydrocarbon at the inlet of the fixed bed competes with the OCM process leading to reduced olefin selectivity. However, by using a catalytic fluid bed reactor the present inventors have found that it is possible to avoid some of the limitations of fix bed reactors when feeding wet natural gas as well as enabling the use of OCM active catalysts for oxidative dehydrogenation of higher hydrocarbons (C2+ alkanes). This discovery allows for use of natural gas with high C2+ content feed gas to be used effectively in a OCM-ODH-steam cracking combined function fluid bed reactor. The fluidized catalyst bed performs the role of a heat exchanger for the inlet gas to enable feeding gas at temperatures below the light off temperature of the catalyst once the oxidation reaction is initiated and produce sufficient heat to maintain a fluid bed temperature above the light off temperature of the catalytic particles.

Accordingly, in one embodiment a method for the preparation of alkenes, such as ethylene, propene, butene, and the like, from alkanes is provided. In one embodiment the method is for preparation of ethylene from ethane, for example wherein the ethane is produced by oxidatively coupling a methane feed gas by OCM.

In some embodiments of the foregoing method for preparation of alkenes, the method comprises charging a feed gas comprising an alkane and oxygen through an inlet to a reactor comprising a fluidized catalyst bed, and contacting the feed gas with the fluidized catalyst bed for a period of time sufficient to convert the alkane to the alkene, wherein the temperature of the feed gas at the inlet is maintained at or below 550° C., and the fluidized catalyst bed is maintained at temperatures ranging from 650° C. to 950° C.

In some embodiments, the method is for preparation of ethylene and the alkane is ethane. When ethylene is the desired product, such embodiments typically include maintaining the fluidized catalyst bed at temperatures above about 800 C, for example above 820 C or above 850 C. In other embodiments of the method when ethylene is the desired product, the ethane is produced by oxidatively coupling methane present in the feed gas.

In some other embodiments, the method is for preparation of propylene and the alkane is propane. When propylene is the desired product, such embodiments typically include maintaining the fluidized catalyst bed at temperatures above about 700 C, for example above 740 C or above 780 C. In other embodiments of the method when propylene is the desired product, the propane is produced by oxidatively coupling methane present in the feed gas.

The catalyst may be any of the catalysts described herein or incorporated by reference. In some embodiments, the fluidized catalyst bed comprises a rare earth catalyst. In other embodiments, the catalyst is a nanostructured catalyst, such as a nanowire catalyst.

In other embodiments, it is advantageous to include methane in the feed gas, and thus the feed gas further comprises methane and in some embodiments the methane is oxidatively coupled to form the alkane. In some of these embodiments, the molar % of methane relative to ethane ranges from about 25% to about 90%. In some of these embodiments wherein methane is included, the alkene is produced by OCM reaction of the methane.

In some of the foregoing embodiments, the alkylene (e.g., ethylene) selectivity is 60% or higher, 65% or higher, 70% or higher or even 75% or higher.

In other embodiments, the alkane (e.g., ethane) conversion is 50% or higher, 55% or higher, 60% or higher, 65% or higher or even 70% or higher.

Figure 4:
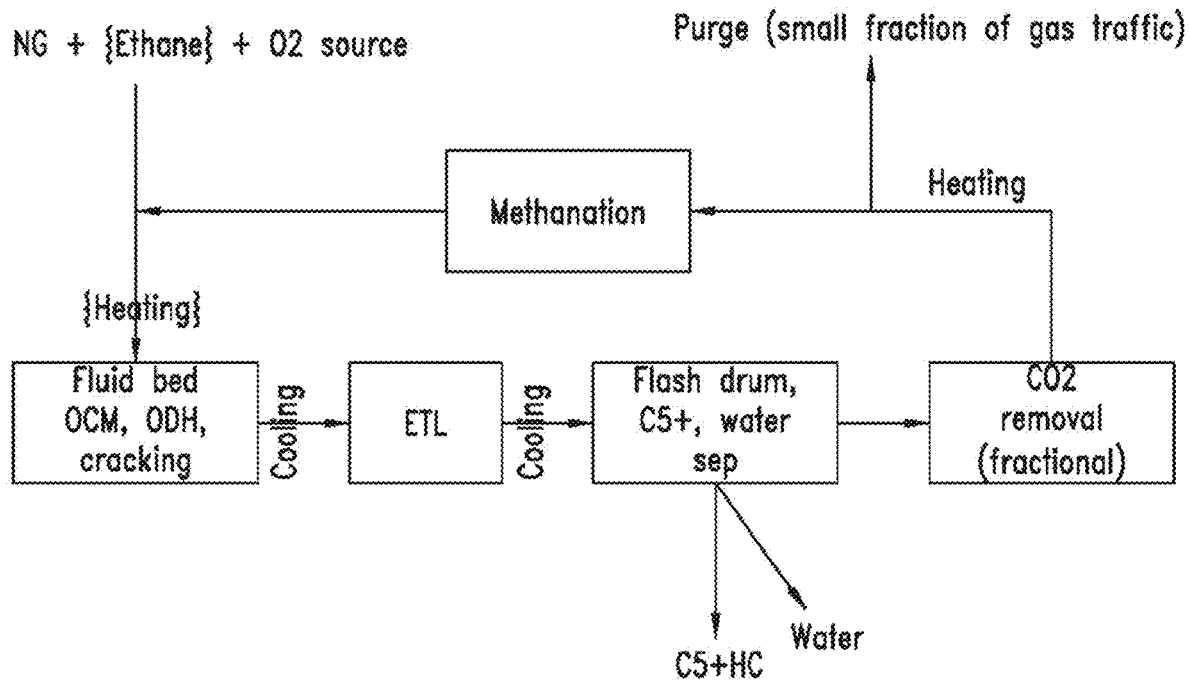
FIG. 4 is a block diagram illustrating an embodiment for integration of OCM and ODH cracking.
Figure 5:
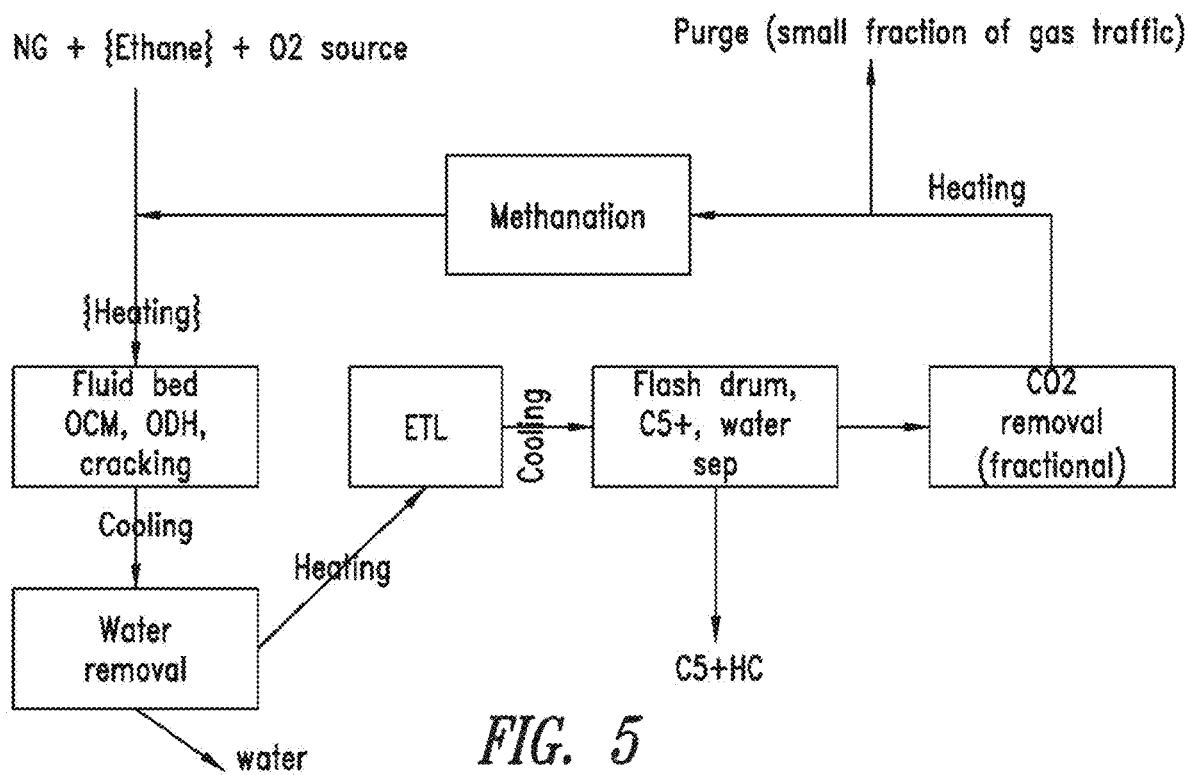
FIG. 5 is a block diagram illustrating an alternative embodiment for integration of OCM and ODH cracking.

The ODH methods described herein above is particularly well suited to integration with downstream process, and in some embodiments the method further comprises one or more steps of oligomerizing the ethylene. An embodiment for integration of the OCM+ODH+cracking catalytic fluidized bed reactor with separation of the olefin products is presented in FIGS. 4 and 5. In these embodiments, the high ethylene content of the natural gas processing reactor couples well with desirable ETL reactor inlet composition. Water may be removed before or after the ETL reactor (FIGS. 4 and 5, respectively). The light hydrocarbon gas after separation of the C5+ fraction can be then processed through a $CO_2$ removal unit and a methanation reactor to utilize the H2 and CO content in this gas stream before being recycled back to the fluid bed OCM+ODH+cracking reactor with additional OSBL natural gas and/or Ethane and $O_2$. In this embodiment, the ability to crack the light hydrocarbon byproduct of the ethylene to liquid reactor in the fluid bed reactor simplifies the handling of the product stream with only three output streams, a small purge for removing inert looping coming from the natural gas feed, a C5+ liquid stream and a waste water stream.

In some embodiments, ethane and the $O_2$ source may be fed together or separately in different sections of the fluid bed. If the $O_2$ and fuel source are fed separately, multiple exhaust may also be used to capture stream with different compositions in order to minimize downstream separation needed in some applications.

One benefit of using a fluid bed combined OCM-ODH—steam cracking reactor versus a traditional Ethane cracker is the reduced reactor complexity and the potential of enabling economical small scale deployment as well as some fuel flexibility. Another benefit of using fluid bed catalytic reactor versus fix bed catalytic reactor is the difference in catalyst temperature profile. The more isothermal profile in the fluid bed reactor may be advantageous in improving the catalytic material tolerance to feed impurity. For example water vapor in the feed may be detrimental at reduced temperature because of the formation of oxy-hydroxide phases. In a fluid bed catalytic reactor this temperature range may be entirely avoided. Similarly formation of stable sulfates or sulfites due to sulfur compound in the natural gas may be avoid in a similar fashion by keeping the entirety of the catalyst bed above 650° C. to 700° C. Continuous mixing of the catalyst solid also enables cycling of the aging atmosphere for individual particles within the bed. This can be advantageous when for example carbon deposits are formed in $O_2$ deprived zone of the reactor, carbon deposit carried back to the front end of the reactor would get removed through oxidative process. Undesirable minor species can also be preferentially removed from the product stream thanks to better temperature control of the bed. Oxidative potential carried by the solid may also contribute to the ability to oxidized highly reactive secondary products as acetylene and dienes.

Figure 6:
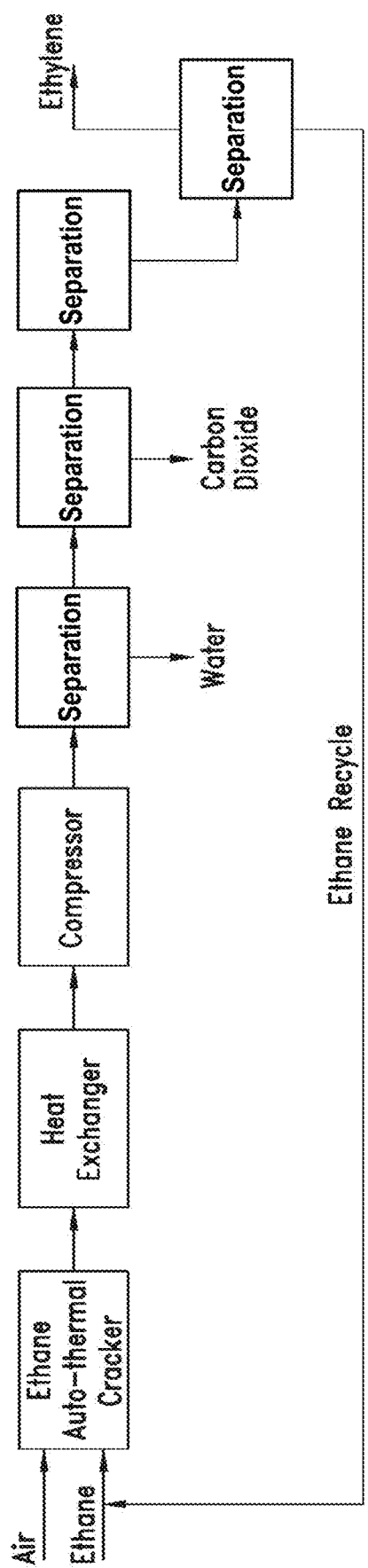
FIG. 6 is a block flow diagram of an embodiment for production of ethylene from ethane employing ethane auto-thermal cracking
Figure 7:
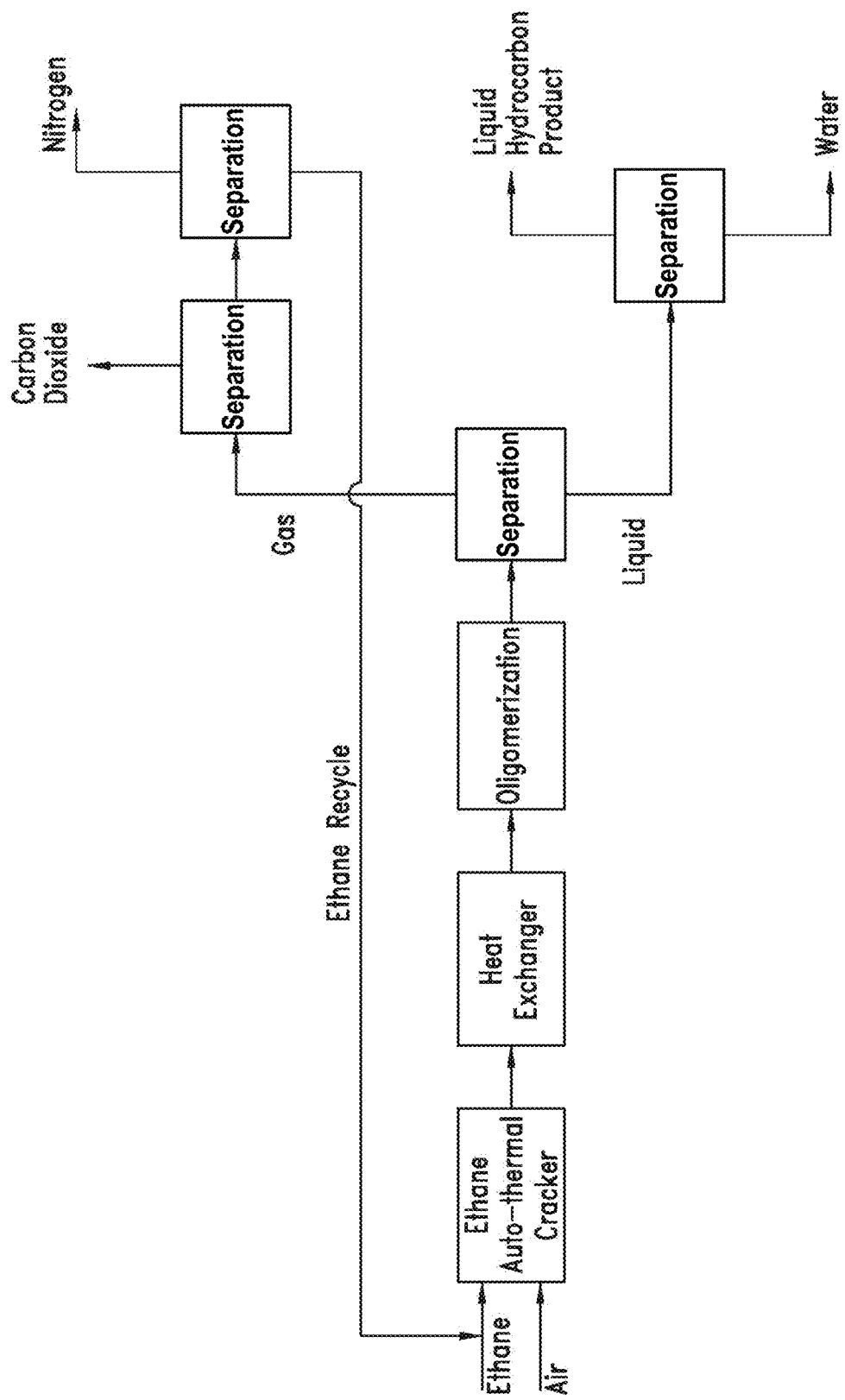
FIG. 7 is a block flow diagram of an embodiment for production of liquid hydrocarbons from ethane employing ethane auto-thermal cracking.

In various other embodiments, auto-thermal cracking of ethane as described above is integrated with downstream units (such as oligomerization reaction, compression and separation) for commercial production of either polymer grade ethylene or liquid hydrocarbon products (such as RBOB gasoline or aromatics). Block flow diagrams that illustrate different embodiments for the conversion of ethane into ethylene (FIG. 6) or liquid hydrocarbon products (FIG. 7) employing auto-thermal cracking of ethane are provided herein.

In support of various embodiments of the present invention, experiments were performed to evaluate the selectivity of the production of olefins from ethane using air as the oxidizer source as a function of carbon:oxygen (C/O) ratio in the feed. These experiments demonstrated that, as C/O ratio is reduced the heat generated by the reaction increases per unit of time resulting in an increase of the operating temperature of the fluid bed catalyst. The data indicate that above about 800° C. in the bed, some of the ethylene formed is obtained through steam cracking as illustrated by an increase of $H_2$ production measured at the reactor outlet. This synergetic ODH and steam cracking within a single reactor has the very desirable effect of increasing both selectivity and yield of ethylene through the process. Homogeneous feed reactivity of the mixture ethane+O2 was also avoided by running the feed gas at temperature under 550° C. while the catalyst bed temperature varied from 700° C. to 850° C.

Ethane conversion and ethylene selectivity as high as 65% and 70%, respectively, were obtained from the aforementioned experiment. The selectivity and yield can be further improved by increasing the residence time in the fluid bed or increasing the temperature of the reactor by reducing heat losses to the environment.

Methods for preparation of higher alkenes, such as propene or butane are analogous to the above described processes, except the corresponding alkane is used in place of ethane.

3. Evaluation of Catalytic Properties

To evaluate the catalytic properties of the catalytic materials in a given reaction, for example those reactions discussed above, various methods can be employed to collect and process data including measurements of the kinetics and amounts of reactants consumed and the products formed. In addition to allowing for the evaluation of the catalytic performances, the data can also aid in designing large scale reactors, experimentally validating models and optimizing the catalytic process.

As an example, in a laboratory setting, an Altamira Benchcat 200 can be employed using a 4 mm ID diameter quartz tube with a 0.5 mm ID capillary downstream. Quartz tubes with 2 mm, 6 mm or 8 mm ID, which optionally comprise a metal jacket for pressurized reactions (e.g., up to 12 barg or more) can also be used. Catalytic materials are tested under a number of different conditions.

In a typical procedure, 50 mg of catalytic material is charged to a 2 mm tube. On either side of the catalytic materials, a small plug of glass wool is loaded to keep the catalytic materials in place. A thermocouple is placed on the inlet side of the catalytic materials bed into the glass wool to get the temperature in the reaction zone. Another thermocouple can be placed on the downstream end into the catalyst bed itself to measure the exotherms, if any.

Once loaded into the reactor, the reactor is inserted into the Altamira instrument and furnace and then a temperature and flow program is started. In some embodiments, the total flow is 50 to 100 sccm of gases but this can be varied and programmed with time. In one embodiment, the temperatures range from 400° C. to 900° C. The reactant gases comprise air or oxygen (diluted with nitrogen or argon) and methane in the case of the OCM reaction and gas mixtures comprising ethane and/or propane with oxygen for oxidative dehydrogenation (ODH) reactions. Other gas mixtures can be used for other reactions.

The primary analysis of these oxidation catalysis runs is the Gas Chromatography (GC) analysis of the feed and effluent gases. From these analyses, the conversion of the oxygen and alkane feed gases can easily be attained and estimates of yields and selectivities of the products and by-products can be determined.

The GC method developed for these experiments employs 4 columns and 2 detectors and a complex valve switching system to optimize the analysis. Specifically, a flame ionization detector (FID) is used for the analysis of the hydrocarbons only. It is a highly sensitive detector that produces accurate and repeatable analysis of methane, ethane, ethylene, propane, propylene and all other simple alkanes and alkenes up to five carbons in length and down to ppm levels.

There are two columns in series to perform this analysis, the first is a stripper column (alumina) which traps polar materials (including the water by-product and any oxygenates generated) until back-flushed later in the cycle. The second column associated with the FID is a capillary alumina column known as a PLOT column, which performs the actual separation of the light hydrocarbons. The water and oxygenates are not analyzed in this method.

For the analysis of the light non-hydrocarbon gases, a Thermal Conductivity Detector (TCD) may be employed which also employs two columns to accomplish its analysis. The target molecules for this analysis are $CO_2$, ethylene, ethane, hydrogen, oxygen, nitrogen, methane and CO. The two columns used here are a porous polymer column known as the Hayes Sep N, which performs some of the separation for the $CO_2$, ethylene and ethane. The second column is a molecular sieve column, which uses size differentiation to perform the separation. It is responsible for the separation of $H_2$, $O_2$, $N_2$, methane and CO.

There is a sophisticated and timing sensitive switching between these two columns in the method. In the first 2 minutes or so, the two columns are operating in series but at about 2 minutes, the molecular sieve column is by-passed and the separation of the first 3 components is completed. At about 5-7 minutes, the columns are then placed back in series and the light gases come off of the sieve according to their molecular size.

The end result is an accurate analysis of all of the aforementioned components from these fixed-bed, gas phase reactions. Analysis of other reactions and gases not specifically described above is performed in a similar manner.

4. Downstream Products

As noted above, in one embodiment the present disclosure is directed to catalytic materials useful in reactions for the preparation of a number of valuable hydrocarbon compounds. For example, in one embodiment the catalytic materials are useful for the preparation of ethylene from methane via the OCM reaction. In another embodiment, the catalytic materials are useful for the preparation of ethylene or propylene via oxidative dehydrogenation of ethane or propane, respectively. Ethylene and propylene are valuable compounds, which can be converted into a variety of consumer products. For example, as shown in FIG. 8, ethylene can be converted into many various compounds including low density polyethylene, high density polyethylene, ethylene dichloride, ethylene oxide, ethylbenzene, linear alcohols, vinyl acetate, alkanes, alpha olefins, various hydrocarbon-based fuels, ethanol and the like. These compounds can then be further processed using methods to obtain other valuable chemicals and consumer products (e.g. the downstream products shown in FIG. 8). Propylene can be analogously converted into various compounds and consumer goods including polypropylenes, propylene oxides, propanol, and the like.

Accordingly, in one embodiment the invention is directed to a method for the preparation of C2 hydrocarbons via the OCM reaction, the method comprises contacting a catalyst as described herein with a gas comprising methane. In some embodiments the C2 hydrocarbons are selected from ethane and ethylene. In other embodiments the disclosure provides a method of preparing downstream products of ethylene. The method comprises converting ethylene into a downstream product of ethylene, wherein the ethylene has been prepared via a catalytic reaction employing a catalyst disclosed herein (e.g., OCM). In some embodiments, the downstream product of ethylene is low density polyethylene, high density polyethylene, ethylene dichloride, ethylene oxide, ethylbenzene, ethanol or vinyl acetate. In other embodiments, the downstream product of ethylene is natural gasoline. In still other embodiments, the downstream product of ethylene comprises 1-hexene, 1-octene, hexane, octane, benzene, toluene, xylene or combinations thereof.

In another embodiment, a process for the preparation of ethylene from methane comprising contacting a mixture comprising oxygen and methane at a temperature below 900° C., below 850° C., below 800° C., below 750° C., below 700° C. or below 650° C. with a catalytic material as disclosed herein is provided.

In another embodiment, the disclosure provides a method of preparing a product comprising low density polyethylene, high density polyethylene, ethylene dichloride, ethylene oxide, ethylbenzene, ethanol or vinyl acetate, alkenes, alkanes, aromatics, alcohols, or mixtures thereof. The method comprises converting ethylene into low density polyethylene, high density polyethylene, ethylene dichloride, ethylene oxide, ethylbenzene, ethanol or vinyl acetate, wherein the ethylene has been prepared via a catalytic reaction employing the catalytic materials disclosed herein.

In more specific embodiments of any of the above methods, the ethylene is produced via an OCM or ODH reaction or combinations thereof.

In one particular embodiment, the disclosure provides a method of preparing a downstream product of ethylene and/or ethane. For example, the downstream product of ethylene may be a hydrocarbon fuel such as natural gasoline or a $C_4$-$C_{14}$ hydrocarbon, including alkanes, alkenes and aromatics. Some specific examples include 1-butene, 1-hexene, 1-octene, hexane, octane, benzene, toluene, xylenes and the like. The method comprises converting methane into ethylene, ethane or combinations thereof by use of a catalytic material disclosed herein, and further oligomerizing the ethylene and/or ethane to prepare a downstream product of ethylene and/or ethane. For example, the methane may be converted to ethylene, ethane or combinations thereof via the OCM reaction as discussed above. The catalytic materials may comprise any catalyst, and the catalyst is not limited with respect to morphology or composition. The catalyst may be an inorganic catalytic polycrystalline nanowire, the nanowire having a ratio of effective length to actual length of less than one and an aspect ratio of greater than ten as measured by TEM in bright field mode at 5 keV, wherein the nanowire comprises one or more elements from any of Groups 1 through 7, lanthanides, actinides or combinations thereof. Alternatively, the catalyst may be an inorganic nanowire comprising one or more metal elements from any of Groups 1 through 7, lanthanides, actinides or combinations thereof and a dopant comprising a metal element, a semi-metal element, a non-metal element or combinations thereof. In other embodiments, the catalytic materials comprise a bulk catalyst. The catalysts may additionally comprise any number of doping elements as discussed above.

Figure 9:
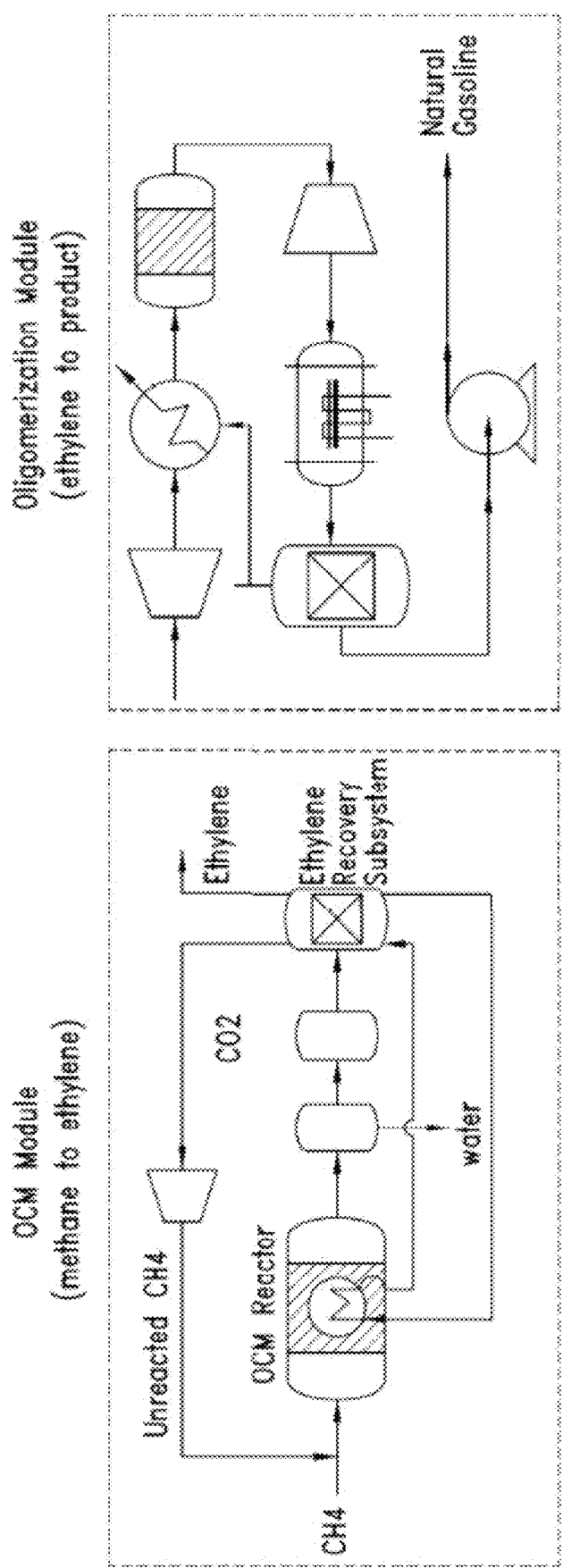
FIG. 9 is a flow chart showing preparation of ethylene-based products.
Figure 10:
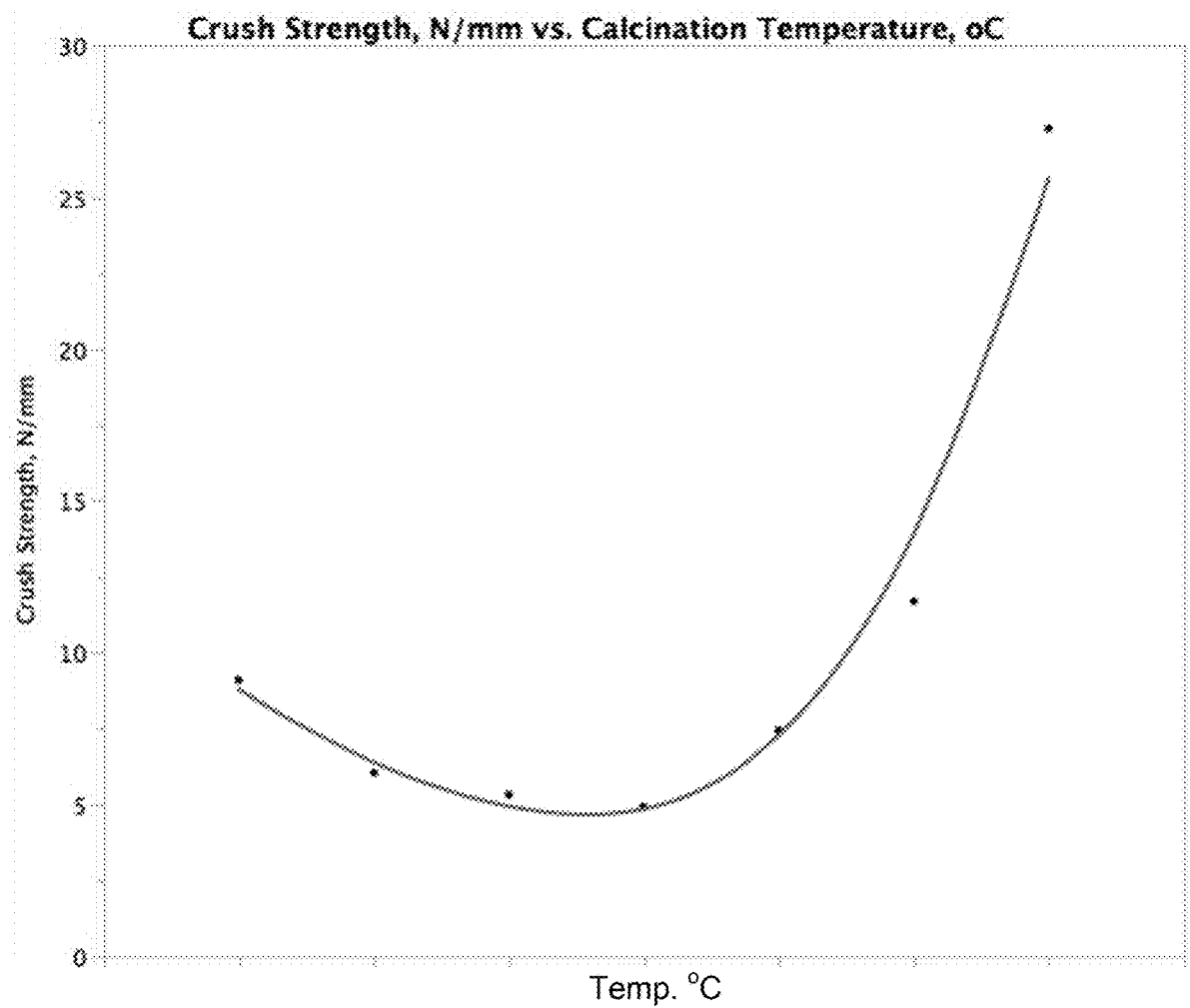
FIG. 10 is a graph of crush strength as a function of calcination temperature for representative catalytic materials.
Figure 11:
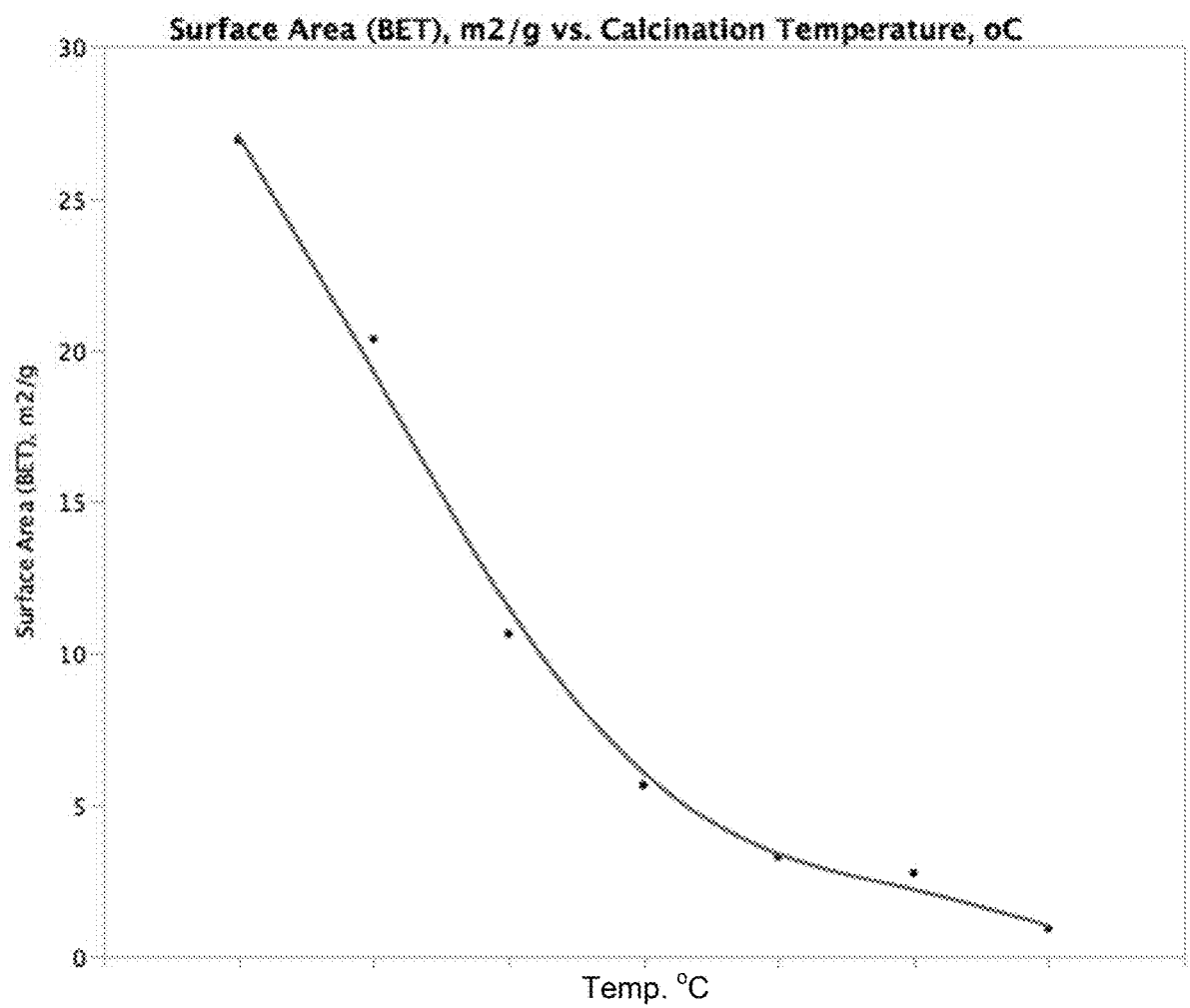
FIG. 11 is a graph of surface area as a function of calcination temperature for representative catalytic materials.
Figure 12:
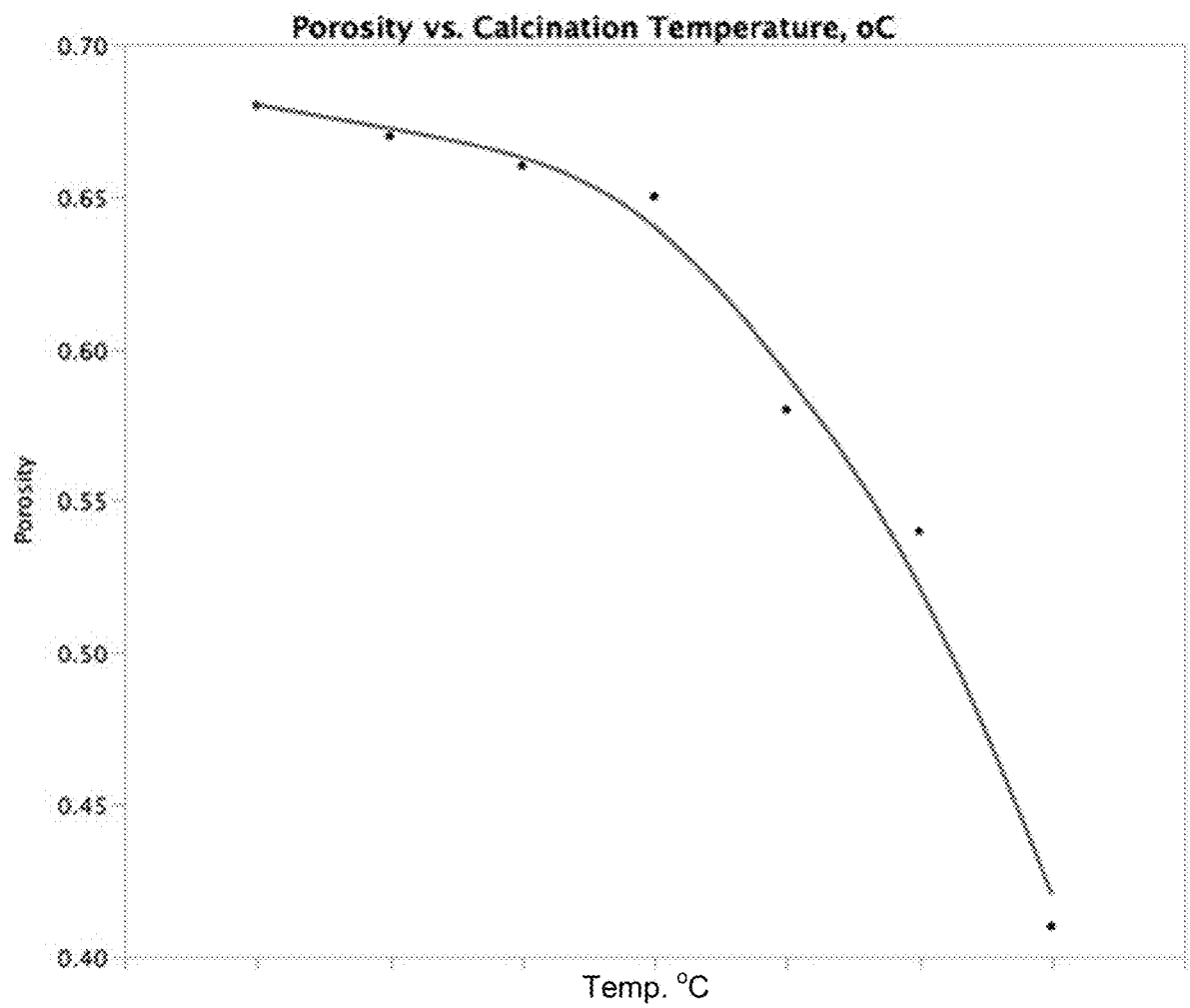
FIG. 12 is a graph of porosity as a function of calcination temperature for representative catalytic materials.
Figure 13:
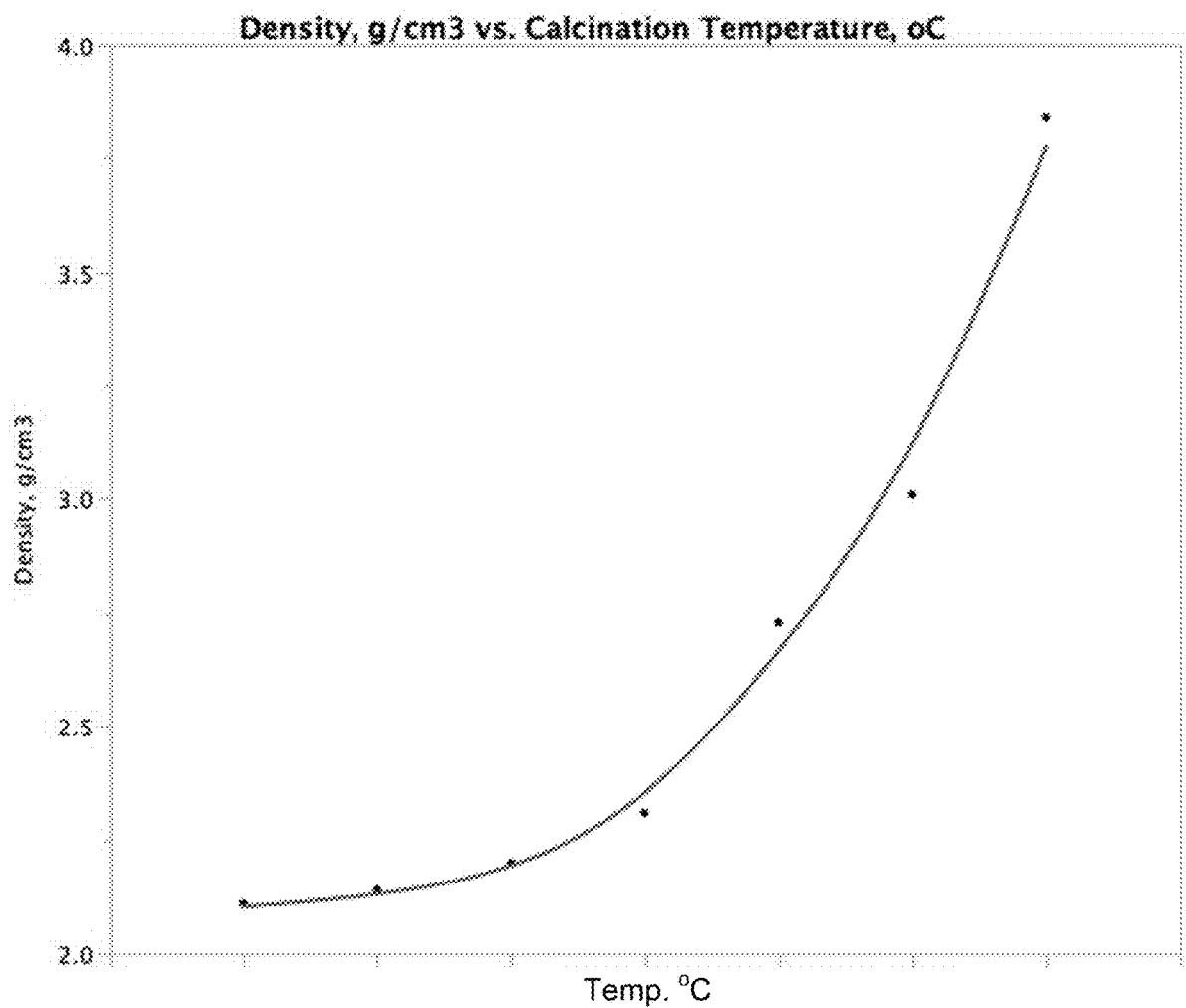
FIG. 13 is a graph of density as a function of calcination temperature for representative catalytic materials.

As depicted in FIG. 9, the method begins with charging methane (e.g., as a component in natural gas) into an OCM reactor. The OCM reaction may then be performed utilizing a catalytic material under any variety of conditions. Water and $CO_2$ are optionally removed from the effluent and unreacted methane is recirculated to the OCM reactor.

Ethylene is recovered and charged to an oligomerization reactor. Optionally the ethylene stream may contain $CO_2$, $H_2O$, $N_2$, ethane, C3's and/or higher hydrocarbons. Oligomerization to higher hydrocarbons (e.g., $C_4$-$C_{14}$) then proceeds under any number of conditions known to those of skill in the art. For example oligomerization may be effected by use of any number of catalysts known to those skilled in the art. Examples of such catalysts include catalytic zeolites, crystalline borosilicate molecular sieves, homogeneous metal halide catalysts, Cr catalysts with pyrrole ligands or other catalysts. Exemplary methods for the conversion of ethylene into higher hydrocarbon products are disclosed in the following references: Catalysis Science & Technology (2011), 1(1), 69-75; Coordination Chemistry Reviews (2011), 255(7-8), 861-880; Eur. Pat. Appl. (2011), EP 2287142 A1 20110223; Organometallics (2011), 30(5), 935-941; Designed Monomers and Polymers (2011), 14(1), 1-23; Journal of Organometallic Chemistry 689 (2004) 3641-3668; Chemistry—A European Journal (2010), 16(26), 7670-7676; Acc. Chem. Res. 2005, 38, 784-793; Journal of Organometallic Chemistry, 695 (10-11): 1541-1549 May 15, 2010; Catalysis Today Volume 6, Issue 3, January 1990, Pages 329-349; U.S. Pat. Nos. 5,968,866; 6,800,702; 6,521,806; 7,829,749; 7,867,938; 7,910,670; 7,414,006 and Chem. Commun., 2002, 858-859, each of which are hereby incorporated in their entirety by reference.

In certain embodiments, the exemplary OCM and oligomerization modules depicted in FIG. 9 may be adapted to be at the site of natural gas production, for example a natural gas field. Thus the natural gas can be efficiently converted to more valuable and readily transportable hydrocarbon commodities without the need for transport of the natural gas to a processing facility.

Referring to FIG. 9, "natural gasoline" refers to a mixture of oligomerized ethylene products. In this regard, natural gasoline comprises hydrocarbons containing 5 or more carbon atoms. Exemplary components of natural gasoline include linear, branched or cyclic alkanes, alkenes and alkynes, as well as aromatic hydrocarbons. For example, in some embodiments the natural gasoline comprises 1-pentene, 1-hexene, cyclohexene, 1-octene, benzene, toluene, dimethyl benzene, xylenes, naphthalene, or other oligomerized ethylene products or combinations thereof. In some embodiments, natural gasoline may also include C3 and C4 hydrocarbons dissolved within the liquid natural gasoline. This mixture finds particular utility in any number of industrial applications, for example natural gasoline is used as feedstock in oil refineries, as fuel blend stock by operators of fuel terminals, as diluents for heavy oils in oil pipelines and other applications. Other uses for natural gasoline are well-known to those of skill in the art.

Example 1

Oxidative Coupling of Methane in Molten Salt Media 0.4 g of catalytic nanowires comprising alkaline earth metals, transition metals and/or rare earth metals, which had been previously crushed to a fine powder, was suspended in 1.3 g of deionized water and 3.44 g of Hitec® Solar Salt (a mixture of sodium and potassium nitrite and nitrate salts, available from Coastal Chemical Co., LLC, Houston Tex.). The water was removed by heating on a hot plat at 240° C. followed by heating at 300° C. overnight.

The nanowire/salt suspension was heated to 500° C. No phase separation of the nanowires and salt was observed with or without stirring. Methane and air were bubbled through the suspension and the product gases were evaluated by gas chromatography.

Example 2

Preparation and Analysis of a Blended Catalytic Material

Perovskite powder (1-2 microns) was blended with nanowires comprising lanthanide oxide and water. The water was removed and the blended catalytic material was formed into 6 mm diameter cylinders by pressing with 1 tonne of pressure. As a comparison, the same process was used to form 6 mm cylinders of perovskite without the lanthanide oxide nanowires. The strength and catalytic properties of the blended catalytic material and the perovskite were tested using 8 mm reactor tube at temperatures between about 500° C. to 650° C. and 0-8 barg. The results are summarized in Table 1 below.

TABLE 1

Properties of Blended Catalytic Materials

|  | Perovskite | Lanthanide Nanowires | Perovskite with Lanthanide |
|---|---|---|---|
| Crush N/mm | 16.6 | 25.1 | 22.6 |
| C2+ selectivity at 600° C. | 40% | 55% | 59% |

Example 3

Blended Catalytic Materials Having Reduced Shrinkage

Perovskite powder (1-2 microns) was blended with nanowires comprising lanthanide oxide and water. The water was removed, and the blended catalytic material was formed into 6 mm diameter cylinders by pressing with 1 tonne of pressure. As a comparison, the same process was used to form 6 mm cylinders of lanthanide oxide nanowires without the perovskite. Catalytic performance in the OCM reaction was tested using an 8 mm reactor tube at temperatures between about 500 to 650 C and 0-8 barg. Shrinkage was determined based on volume lost for the 6 mm diameter cylinders upon exposure to 900° C. in static air for 48 hours. Volume was measure using digital calipers and averaged for 5 cylinders. The data is presented in Table 2.

TABLE 2

Properties of Catalytic Materials

|  | Lanthanide Nanowires | Perovskite | Perovskite with Lanthanide |
|---|---|---|---|
| Volume Loss (48 h @ 900 C.) | 6% | 0% | 0.5% |
| C2+ selectivity at 600° C. | 55% | 40% | 59% |

Example 4

Preparation of Doped Catalyst with Carbonate Precursor

A nanowire catalyst comprising alkaline earth metals, transition metals and/or rare earth metals was doped with either alkaline earth nitrate or alkaline earth carbonate and formed into 6 mm rings by pressing at 1 ton. The nitrate-doped catalyst was calcined at 800° C., while the carbonate-doped catalyst was calcined at 350° C. The crush strength was determined at different time points after storage at ambient conditions (exposure to air at temperatures ranging from about 20° C. to 30° C.). The carbonate-doped catalyst had a significantly better crush strength after storage in ambient conditions (e.g., a decrease in crush strength of no more than about 20% after 100 hours), while the nitrate-doped catalyst rapidly decomposed. The OCM performance (i.e., C2+ selectivity) of both catalysts is essentially the same.

Example 5

Preparation of Catalytic Materials with Grind and Fire (GNF) Method

Solutions of the desired dopants were prepared and combined with catalytic nanowires comprising alkaline earth metals, transition metals and/or rare earth metals, which had been previously crushed to a fine powder. This mixture was dried in an oven at 120° C. and then milled. The dried powder was calcined at 800° C.

For forming extrudates, the calcined powder was blended with a cellulosic porogen, an acidic peptizing agent, an inorganic binder, an extrusion aid and optionally an inorganic diluent. DI water was added until the moisture content reached about 15-25% (w/w). This paste was extruded to form rings and dried in an oven at 120° C. followed by calcination at 800° C.

For forming tablets, the calcined powder was blended with a cellulosic porogen, an acidic peptizing agent, a lubricant, an inorganic binder and optionally an inorganic diluent. The amount of water containing ingredients was controlled so that the final moisture content stayed below 5% (w/w). This mixture was tableted using a tablet press and dried in an oven at 120° C. followed by calcination at 800° C.

Example 6

Effect of Processing Parameters on Physical Properties of Catalytic Materials Many factors have been found to contribute to the final density, porosity, crush strength and surface area of the extruded or tableted catalytic materials. To determine the effect of calcination temperature on the crush strength, surface area and porosity of the catalytic materials, the following experiment was performed.

An extrudate comprising catalytic nanowires comprising alkaline earth metals, transition metals and/or rare earth metals was prepared according to the general procedures described herein. Samples of the extrudates were calcined at a range of temperatures. The crush strength, surface area, porosity and density of the catalytic materials as a function of calcination temperature are provided in FIGS. 10-13, respectively. As can be seen, the crush strength and the density generally increase as calcination temperature increases. While not being bound by theory, it is believed that this increase in crush strength is related to an increase in density owing to sintering of the catalyst material.

In contrast to the crush strength and density, the porosity and surface area of the catalytic materials both decrease with increasing calcination temperature. A significant decrease in porosity is observed at increasing temperatures. At higher temperatures, the catalytic materials become very dense and strong.

Example 7

Evaluation of Bifunctional Catalysts

Figure 14:
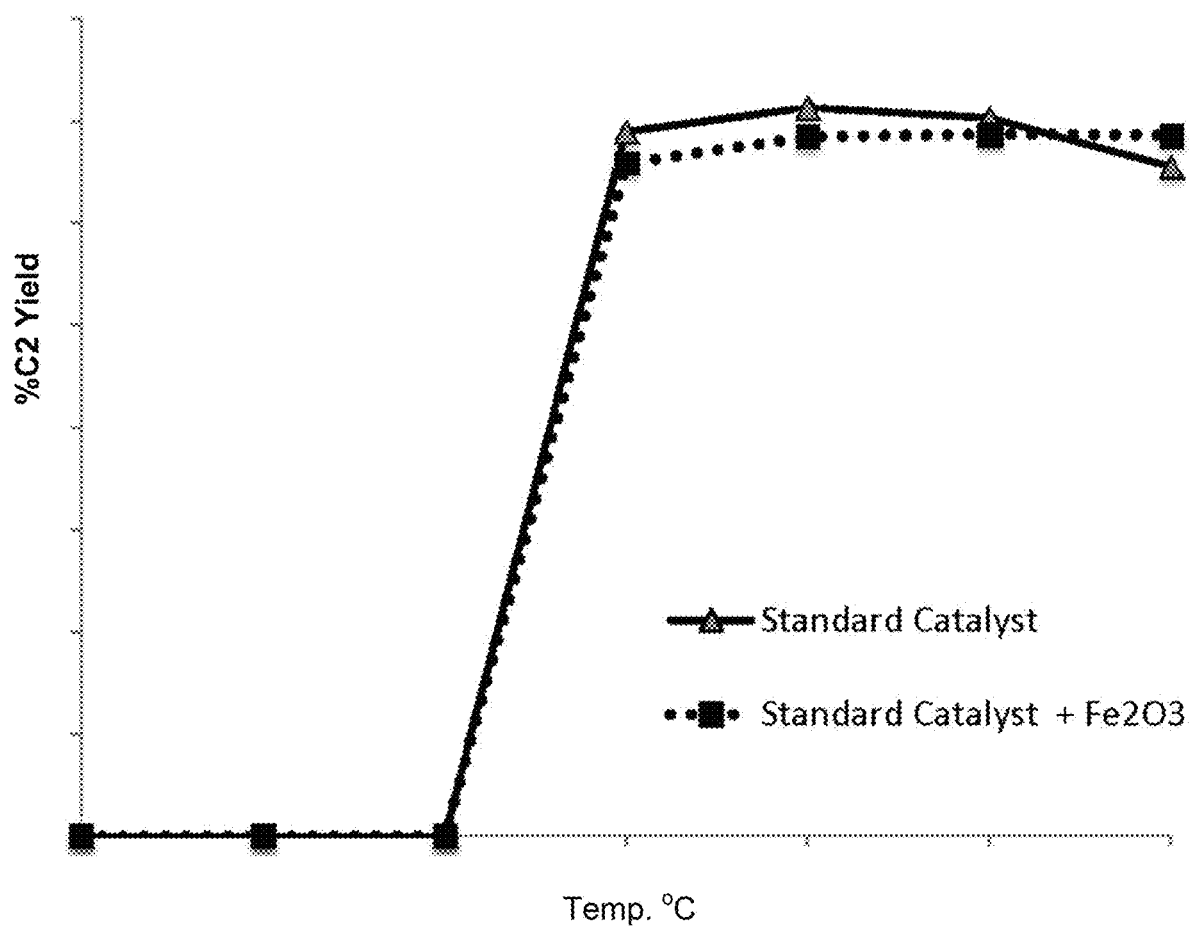
FIG. 14 provides data comparing the C2 yield of OCM reactions performed in the presence of either a standard catalyst or a bifunctional catalyst comprising the standard catalyst and $Fe_2O_3$.
Figure 15:
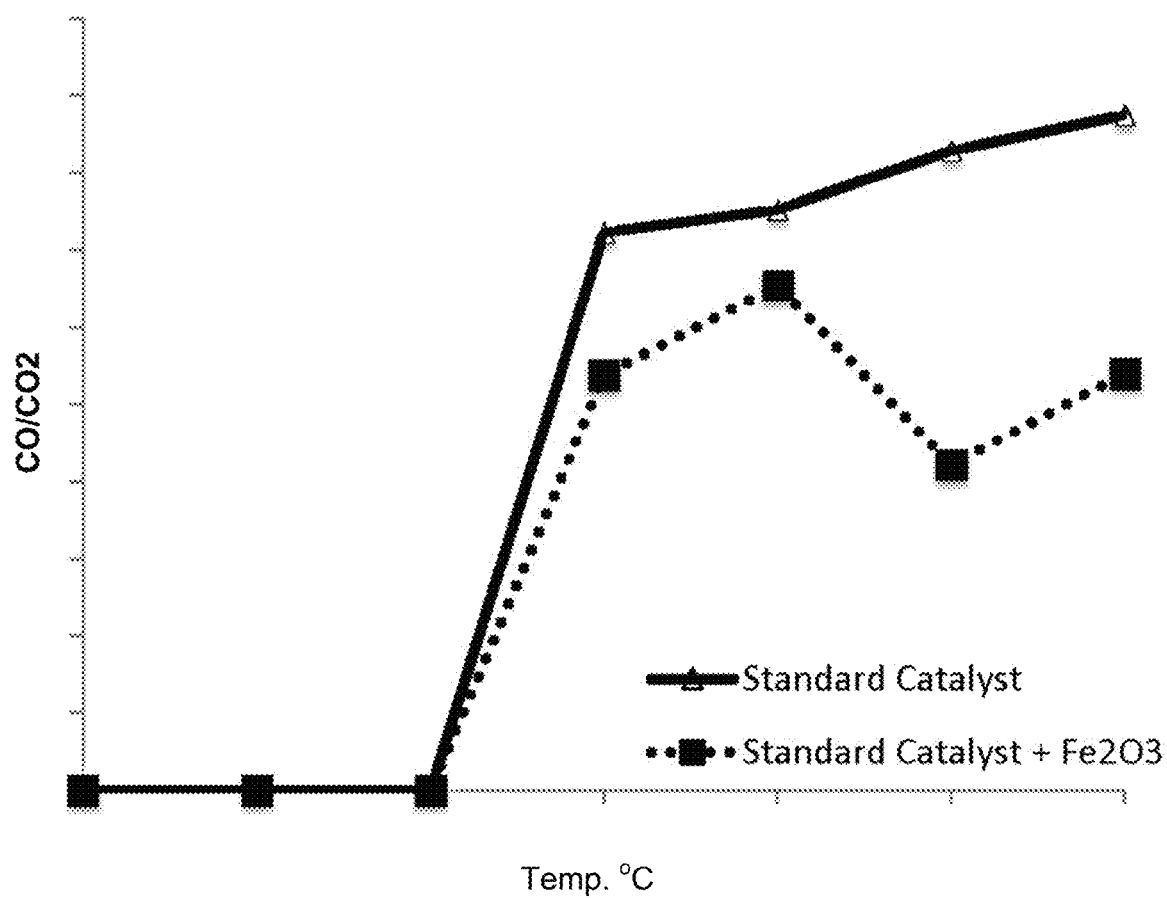
FIG. 15 is a graph comparing the $CO/CO_2$ concentration ratio in OCM reactions performed in the presence of either a standard catalyst or a bifunctional catalyst comprising the standard catalyst and $Fe_2O_3$.

A catalyst comprising nanowires comprising alkaline earth metals, transition metals and/or rare earth metals (a "standard catalyst") was prepared according to the procedures described herein. A bifunctional catalyst was prepared by physically blending the standard catalyst with $Fe_2O_3$. The standard catalyst and the bifunctional catalyst were used as catalysts for OCM at temperatures ranging from about 550° C. to about 800° C., and the product gases were analyzed. As can be seen in FIGS. 14 and 15, the bifunctional catalyst decreased the $CO/CO_2$ concentration ratio compared with the standard catalyst while maintaining the same C2 yield.

Example 8

Evaluation of Catalyst Compositions and Forms

Identical OCM catalyst material compositions were formed into tube shaped particles having cross sectional diameters of 5.3 mm and lengths of approximately 8 mm. Three different inside diameter extrudates were prepared so as to yield three different wall thicknesses for the tubes: 1.14 mm, 1.41 mm, and 1.8 mm. A control form of 2 mm extrudate pellets was also prepared. All of the extrudates were prepared by identical methods other than the resulting inside diameters. Each of the three forms and the control pellets was tested in an adiabatic pilot scale OCM reactor operating between 350° C. and 550° C. feed gas temperature.

Example 9

Exemplary OCM Reaction with Formed Catalytic Material

Figure 16:
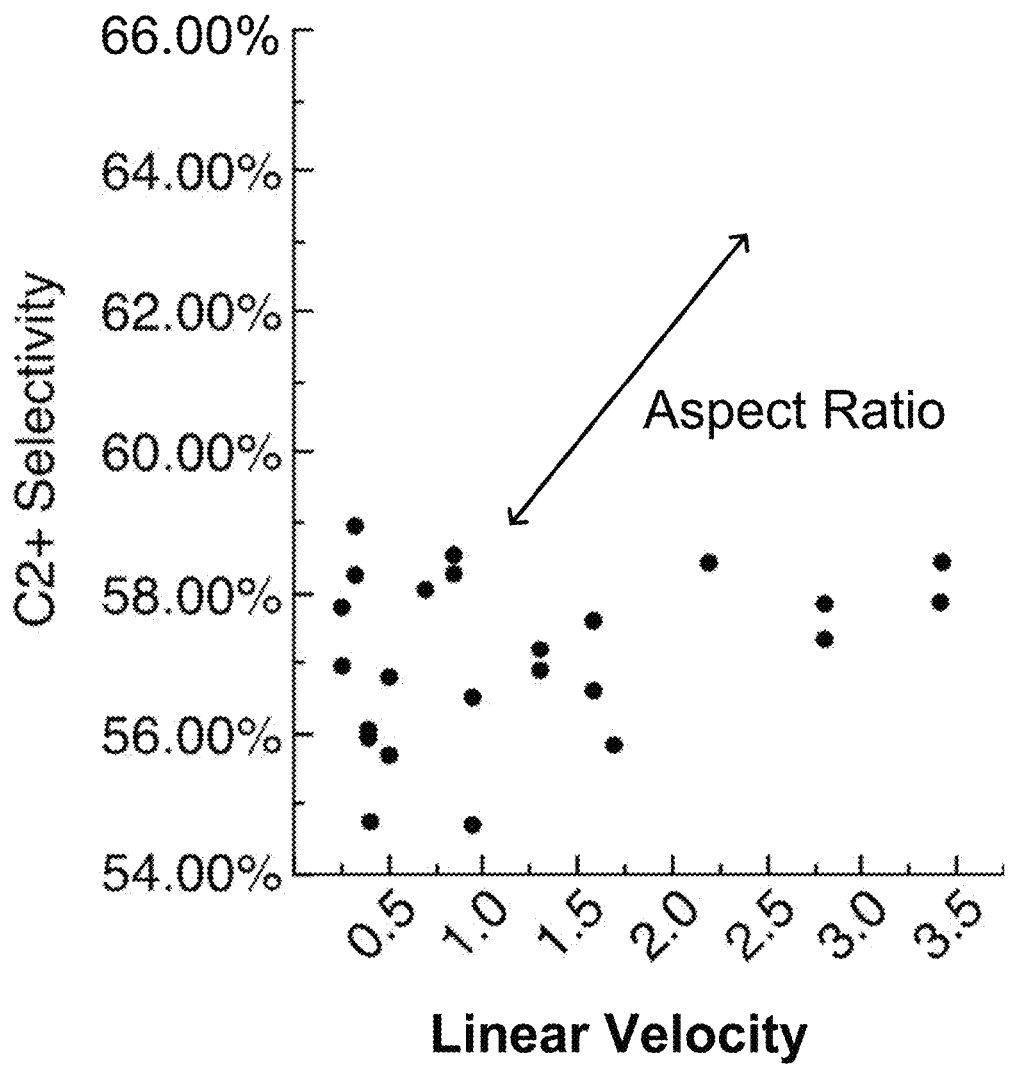
FIG. 16 presents data for C2+ selectivity as a function of gas linear velocity for an OCM reaction performed in the presence of a representative catalyst.

In an exemplary reaction, a catalytic nanowire described herein was formed into a ring-shaped catalytic material as described herein including addition of binders and diluents. The rings had outer diameters of about 6 mm and inner diameters of about 3 mm. The rings were packed into a catalytic bed and a mixture of air and methane was passed through the catalytic bed at linear velocities ranging from less than 1 m/s up to about 3.5 m/s. The C2+ selectivity was determined as a function of gas linear velocity. Data is presented in FIG. 16. From this data it is apparent that C2+ selectivities range from about 50% to about 60% for linear velocities of gas ranging from about 0.2 m/s to about 4 m/s.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A catalytic material comprising:
   (a) an OCM active catalyst; and
   (b) a second catalyst comprising the following formula:

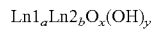
   $Ln1_aLn2_bO_x(OH)_y$ wherein:
   Ln1 and Ln2 are each independently different lanthanide elements;
   O is oxygen;
   OH is hydroxy;
   a is a number greater than 0; and
   b, x and y are each independently numbers of 0 or greater, provided that at least one of x or y is greater than 0, and
   wherein the catalytic material comprises a methane conversion of greater than 10% and a C2+selectivity of greater than 50% when the catalytic material is employed as a heterogeneous catalyst in the oxidative coupling of methane at a temperature ranging from about 550° C. to about 850° C.

2. The catalytic material of claim 1, wherein b and x are each independently numbers greater than 0, and y is 0.

3. The catalytic material of claim 1, wherein the OCM active catalyst is a bulk catalyst and the second catalyst is a nanostructured catalyst.

4. The catalytic material of claim 1, wherein the OCM active catalyst is a nanostructured catalyst.

5. The catalytic material of claim 4, wherein the OCM active catalyst is a nanowire catalyst.

6. The catalytic material of claim 1, wherein the second catalyst comprises a nanostructured catalyst comprising a lanthanum/neodymium oxide, a lanthanum/cerium oxide, a neodymium/cerium oxide, a lanthanum/samarium oxide, a neodymium/samarium oxide, a europium/neodymium oxide, a lanthanum/erbium oxide, a neodymium/erbium oxide, or a europium/lanthanum oxide.

7. The catalytic material of claim 1, wherein the second catalyst comprises a nanostructured catalyst, and Ln1 and Ln2 are each independently lanthanum, cerium, praseodymium, neodymium, samarium, europium, gadolinium, terbium, dysprosium, holmium, erbium, thulium, ytterbium or lutetium.

8. The catalytic material of claim 1, wherein the OCM active catalyst comprises titanium, zirconium, hafnium or combinations thereof.

9. The catalytic material of claim 1, wherein the catalytic material further comprises an alkaline earth metal and one or more lanthanide elements.

10. The catalytic material of claim 9, wherein the lanthanide elements are selected from Gd and Nd.

11. The catalytic material of claim 9, wherein the alkaline earth metal is magnesium, calcium, strontium or barium.

12. The catalytic material of claim 1, wherein the weight ratio of the OCM active catalyst to the second catalyst ranges from about 80% to about 60%.

13. The catalytic material of claim 1, wherein the crush strength of the catalytic material is greater than about 5 N/mm.

14. The catalytic material of claim 1, wherein the catalytic material has a volume loss of less than 5% when heated to 900° C. in air for 100 hours.

15. The catalytic material of claim 1, wherein the OCM activity of the catalytic material is greater than the OCM activity of either (a) or (b) alone.

16. The catalytic material of claim 1, wherein the OCM active catalyst comprises MgO, $La_2O_3$, $Na_2WO_4$, $Mn_2O_3$, $Mn_3O_4$, $Mg_6MnO_8$, $Zr_2Mo_2O_8$, $NaMnO_4$, $Mn_2O_3/Na_2WO_4$, $Mn_3O_4/Na_2WO_4$ or $Na/MnO_4/MgO$, $Mn/WO_4$, $Nd_2O_3$, $Sm_2O_3$, $Eu_2O_3$ or combinations thereof.

17. The catalytic material of claim 1, wherein the OCM active catalyst further comprises a dopant combination comprising sodium and at least one element from each of groups 2, 16, or combinations thereof.

18. The catalytic material of claim 1, wherein the catalytic material further comprises a methane conversion of greater than 20% and a C2+selectivity of greater than 50% when the catalytic material is employed as a heterogeneous catalyst in the oxidative coupling of methane at a temperature ranging from about 550° C. to about 850° C.

19. The catalytic material of claim 1, wherein the catalytic material further comprises a methane conversion of greater than 10% and a C2+selectivity of greater than 50% when the catalytic material is employed as a heterogeneous catalyst in the oxidative coupling of methane at a feedstock inlet temperature of less than 750° C. measured at an inlet of a reactor comprising the catalytic material.

20. The catalytic material of claim 19, wherein the C2+selectivity of the catalytic material in the OCM reaction is greater than about 65% when the OCM reaction is conducted at a feedstock inlet temperature of about 600° C. or lower measured at an inlet of a reactor comprising the catalytic material.

21. The catalytic material of claim 1, wherein the catalytic material further comprises a methane conversion of greater than 20% and a C2+selectivity of greater than 50% when the catalytic material is employed as a heterogeneous catalyst in the oxidative coupling of methane at a feedstock inlet temperature of less than 750° C. measured at an inlet of a reactor comprising the catalytic material.

22. The catalytic material of claim 21, wherein the C2+selectivity of the catalytic material in the OCM reaction is greater than about 65% when the OCM reaction is conducted at a feedstock inlet temperature of about 600° C. or lower measured at an inlet of a reactor comprising the catalytic material.

23. A formed catalytic material for performing oxidative coupling of methane at linear velocities ranging from about 0.1 m/s to about 10 m/s, the catalytic material comprising:
a) a catalyst;
b) a non-tessellating shape having a plurality of penetrating holes therethrough, the non-tessellating shape selected from the group consisting of an ellipse, a pentagon, and a ring shape;
c) a binder or diluent;
d) a crush strength of greater than about 2 N/mm after exposure to air comprising water at temperatures between about 20° C. and 30° C. for greater than 50 hours; and
d) a bed void fraction of greater than 0.3.

24. A formed catalytic material for performing oxidative coupling of methane at linear velocities ranging from about 0.1 m/s to about 10 m/s, the formed catalytic material comprising (a) a catalyst and a binder or diluent; (b) a non-tessellating shape having a plurality of penetrating holes therethrough, the non-tessellating shape selected from the group consisting of an ellipse, a pentagon, and a ring shape; and (c) at least one rounded or chamfered edge, at least one convex surface or combinations thereof, wherein the catalytic material comprises a methane conversion of greater than 20% and a C2+selectivity of greater than 50% when the catalytic material is employed as a heterogeneous catalyst in the oxidative coupling of methane at a temperature ranging from about 550° C. to about 850° C.

25. A formed catalytic material for performing oxidative coupling of methane at linear velocities ranging from about 0.1 m/s to about 10 m/s, the formed catalytic material comprising (a) a catalyst and a least one binder or diluent; (b) a non-tessellating shape having a plurality of penetrating holes therethrough, the non-tessellating shape selected from the group consisting of an ellipse, a pentagon, and a ring shape; and (c) at least one rounded or chamfered edge, at least one convex surface or combinations thereof, wherein the catalytic material comprises a methane conversion of greater than 10% and a C2+selectivity of greater than 50% when the catalytic material is employed as a heterogeneous catalyst in the oxidative coupling of methane at a temperature ranging from about 550° C. to about 850° C.

* * * * *